(12) United States Patent
Hassibi

(10) Patent No.: US 11,485,997 B2
(45) Date of Patent: Nov. 1, 2022

(54) NUCLEIC ACID SEQUENCE IDENTIFICATION USING SOLID-PHASE CYCLIC SINGLE BASE EXTENSION

(71) Applicant: InSilixa, Inc., Sunnyvale, CA (US)

(72) Inventor: Arjang Hassibi, Santa Clara, CA (US)

(73) Assignee: INSILIXA, INC., Santa Clara, CA (US)

(*) Notice: Subject to any disclaimer, the term of this patent is extended or adjusted under 35 U.S.C. 154(b) by 616 days.

(21) Appl. No.: 16/102,310

(22) Filed: Aug. 13, 2018

(65) Prior Publication Data

US 2019/0062819 A1 Feb. 28, 2019

Related U.S. Application Data

(63) Continuation of application No. PCT/US2017/020887, filed on Mar. 6, 2017.

(60) Provisional application No. 62/304,859, filed on Mar. 7, 2016.

(51) Int. Cl.
| | | |
|---|---|---|
| C12Q 1/6837 | (2018.01) | |
| C12Q 1/6876 | (2018.01) | |
| C12Q 1/6874 | (2018.01) | |
| G01N 33/58 | (2006.01) | |

(52) U.S. Cl.
CPC .......... *C12Q 1/6837* (2013.01); *C12Q 1/6874* (2013.01); *C12Q 1/6876* (2013.01); *G01N 33/582* (2013.01); *C12Q 2563/107* (2013.01); *C12Q 2600/156* (2013.01); *C12Q 2600/16* (2013.01); *C12Q 2600/166* (2013.01)

(58) Field of Classification Search
CPC ...................................................... C12Q 1/68
See application file for complete search history.

(56) References Cited

U.S. PATENT DOCUMENTS

| | | | |
|---|---|---|---|
| 4,027,971 | A | 6/1977 | Kolman et al. |
| 4,469,863 | A | 9/1984 | Ts'o et al. |
| 4,539,295 | A | 9/1985 | Blough, Jr. |
| 4,562,157 | A | 12/1985 | Lowe et al. |
| 4,683,195 | A | 7/1987 | Mullis et al. |
| 4,683,202 | A | 7/1987 | Mullis et al. |
| 4,711,955 | A | 12/1987 | Ward et al. |
| 4,994,373 | A | 2/1991 | Stavrianopoulos et al. |
| 5,034,506 | A | 7/1991 | Summerton et al. |
| 5,082,830 | A | 1/1992 | Brakel et al. |
| 5,130,238 | A | 7/1992 | Malek et al. |
| 5,210,015 | A | 5/1993 | Gelfand et al. |
| 5,216,141 | A | 6/1993 | Benner |
| 5,235,033 | A | 8/1993 | Summerton et al. |
| 5,270,184 | A | 12/1993 | Walker et al. |
| 5,310,652 | A | 5/1994 | Gelfand et al. |
| 5,322,770 | A | 6/1994 | Gelfand |
| 5,323,115 | A | 6/1994 | Werner, Jr. |
| 5,328,824 | A | 7/1994 | Ward et al. |
| 5,333,675 | A | 8/1994 | Mullis et al. |
| 5,386,023 | A | 1/1995 | Sanghvi et al. |
| 5,399,491 | A | 3/1995 | Kacian et al. |
| 5,407,800 | A | 4/1995 | Gelfand et al. |
| 5,409,818 | A | 4/1995 | Davey et al. |
| 5,449,767 | A | 9/1995 | Ward et al. |
| 5,455,166 | A | 10/1995 | Walker |
| 5,455,705 | A | 10/1995 | Gusinov |
| 5,466,348 | A | 11/1995 | Holm-Kennedy |
| 5,475,610 | A | 12/1995 | Atwood et al. |
| 5,476,928 | A | 12/1995 | Ward et al. |
| 5,480,784 | A | 1/1996 | Kacian et al. |
| 5,487,972 | A | 1/1996 | Gelfand et al. |
| 5,491,063 | A | 2/1996 | Fisher et al. |
| 5,538,848 | A | 7/1996 | Livak et al. |
| 5,571,673 | A | 11/1996 | Picone |
| 5,573,906 | A | 11/1996 | Bannwarth et al. |
| 5,599,668 | A | 2/1997 | Stimpson et al. |
| 5,602,240 | A | 2/1997 | De Mesmaeker et al. |
| 5,627,054 | A | 5/1997 | Gillespie |
| 5,632,957 | A | 5/1997 | Heller et al. |
| 5,637,684 | A | 6/1997 | Cook et al. |
| 5,644,048 | A | 7/1997 | Yau |
| 5,656,493 | A | 8/1997 | Mullis et al. |
| 5,674,698 | A | 10/1997 | Zarling et al. |
| 5,677,152 | A | 10/1997 | Birch et al. |
| 5,723,591 | A | 3/1998 | Livak et al. |

(Continued)

FOREIGN PATENT DOCUMENTS

| | | |
|---|---|---|
| CN | 1250483 A | 4/2000 |
| CN | 1461350 A | 12/2003 |

(Continued)

OTHER PUBLICATIONS

Deshpande et al. Current Protocols in Cytometry 13.4.1-13.4.11 (Year: 2005).*
Pastinen et al., Minisequencing: a specific tool for DNA analysis and diagnostics on oligonucleotide arrays. Genome Research 7 : 606-614 (Year: 1997).*
Pastinen et al., A system for specific, high-throughput genotyping by allele-specific primer extension on microarrays. Genome Research 7 : 606-614 (Year: 2000).*
Saiki et al., Genetic analysis of amplified DNA with immobilized sequence-specific oligonucleotide probes. PNAS 86 : 6230-6234 (Year: 1989).*
Shumaker et al., Mutation Detection by Solid phase Primer extension. Human Mutation 7 :346-354 (Year: 1996).*

(Continued)

*Primary Examiner* — Ethan C Whisenant
(74) *Attorney, Agent, or Firm* — Wilson Sonsini Goodrich & Rosati

(57) ABSTRACT

The present disclosure provides methods, devices and systems for detecting a presence of a nucleic acid molecule having a nucleic acid sequence. Detection of cyclic single base extension can be used to detect a nucleic acid molecule hybridized to a probe and detect a presence of a nucleic acid. The methods disclosed herein can detect a nucleic acid molecule present in a nucleic acid sample at low concentrations and in the presence of background nucleic acids having high sequence similarity.

20 Claims, 13 Drawing Sheets

Specification includes a Sequence Listing.

(56) References Cited

U.S. PATENT DOCUMENTS

| | | |
|---|---|---|
| 5,744,305 A | 4/1998 | Fodor et al. |
| 5,773,258 A | 6/1998 | Birch et al. |
| 5,789,224 A | 8/1998 | Gelfand et al. |
| 5,804,375 A | 9/1998 | Gelfand et al. |
| 5,807,522 A | 9/1998 | Brown et al. |
| 5,837,501 A | 11/1998 | Beumer et al. |
| 5,854,033 A | 12/1998 | Lizardi et al. |
| 5,871,928 A | 2/1999 | Fodor et al. |
| 5,876,930 A | 3/1999 | Livak et al. |
| 5,919,630 A | 7/1999 | Nadeau et al. |
| 5,925,519 A | 7/1999 | Jensen et al. |
| 5,955,351 A | 9/1999 | Gerdes et al. |
| 5,974,164 A | 10/1999 | Chee |
| 5,994,056 A | 11/1999 | Higuchi |
| 6,025,601 A | 2/2000 | Trulson et al. |
| 6,030,787 A | 2/2000 | Livak et al. |
| 6,040,193 A | 3/2000 | Winkler et al. |
| 6,048,690 A | 4/2000 | Heller et al. |
| 6,054,270 A | 4/2000 | Southern |
| 6,083,763 A | 7/2000 | Balch |
| 6,103,476 A | 8/2000 | Tyagi et al. |
| 6,110,426 A | 8/2000 | Shalon et al. |
| 6,110,749 A | 8/2000 | Obremski et al. |
| 6,114,122 A | 9/2000 | Besemer et al. |
| 6,124,102 A | 9/2000 | Fodor et al. |
| 6,127,155 A | 10/2000 | Gelfand et al. |
| 6,153,425 A | 11/2000 | Kozwich et al. |
| 6,169,981 B1 | 1/2001 | Werbos |
| 6,171,785 B1 | 1/2001 | Higuchi |
| 6,174,670 B1 | 1/2001 | Wittwer et al. |
| 6,225,625 B1 | 5/2001 | Pirrung et al. |
| 6,251,639 B1 | 6/2001 | Kurn |
| 6,258,569 B1 | 7/2001 | Livak et al. |
| 6,261,776 B1 | 7/2001 | Pirrung et al. |
| 6,291,166 B1 | 9/2001 | Gerdes et al. |
| 6,291,183 B1 | 9/2001 | Pirrung et al. |
| 6,312,906 B1 | 11/2001 | Cass et al. |
| 6,319,958 B1 | 11/2001 | Johnson et al. |
| 6,327,410 B1 | 12/2001 | Walt et al. |
| 6,330,092 B1 | 12/2001 | Aronson |
| 6,365,729 B1 | 4/2002 | Tyagi et al. |
| 6,391,550 B1 | 5/2002 | Lockhart et al. |
| 6,403,341 B1 | 6/2002 | Barnes et al. |
| 6,406,848 B1 | 6/2002 | Bridgham et al. |
| 6,410,278 B1 | 6/2002 | Notomi et al. |
| 6,428,957 B1 | 8/2002 | Delenstarr |
| 6,432,695 B1 | 8/2002 | Zou et al. |
| 6,465,175 B2 | 10/2002 | Horn et al. |
| 6,469,524 B1 | 10/2002 | Oberdier |
| 6,472,887 B1 | 10/2002 | Tullis et al. |
| 6,516,276 B1 | 2/2003 | Ghandour et al. |
| 6,593,091 B2 | 7/2003 | Keys et al. |
| 6,600,996 B2 | 7/2003 | Webster et al. |
| 6,610,482 B1 | 8/2003 | Fodor et al. |
| 6,649,378 B1 | 11/2003 | Kozwich et al. |
| 6,673,536 B1 | 1/2004 | Stoughton et al. |
| 6,713,297 B2 | 3/2004 | McMillan et al. |
| 6,724,324 B1 | 4/2004 | Lambert |
| 6,743,581 B1 | 6/2004 | Vo-Dinh |
| 6,744,502 B2 | 6/2004 | Hoff et al. |
| 6,750,963 B2 | 6/2004 | Sampas |
| 6,783,934 B1 | 8/2004 | McMillan et al. |
| 6,806,052 B2 | 10/2004 | Bridgham et al. |
| 6,814,934 B1 | 11/2004 | Higuchi |
| 6,828,100 B1 | 12/2004 | Ronaghi |
| 6,859,570 B2 | 2/2005 | Walt et al. |
| 6,859,750 B1 | 2/2005 | Frazier |
| 6,872,527 B2 | 3/2005 | Gerdes et al. |
| 6,911,327 B2 | 6/2005 | McMillan et al. |
| 6,942,971 B2 | 9/2005 | McMillan et al. |
| 6,946,251 B2 | 9/2005 | Kurn |
| 6,953,958 B2 | 10/2005 | Baxter et al. |
| 6,969,488 B2 | 11/2005 | Bridgham et al. |
| 7,060,431 B2 | 6/2006 | Chee et al. |
| 7,064,197 B1 | 6/2006 | Rabbani et al. |
| 7,087,387 B2 | 8/2006 | Gerdes et al. |
| 7,122,355 B2 | 10/2006 | Ankenbauer et al. |
| 7,145,645 B2 | 12/2006 | Blumenfeld et al. |
| 7,223,540 B2 | 5/2007 | Pourmand et al. |
| 7,291,496 B2 | 11/2007 | Holm-Kennedy |
| 7,307,802 B2 | 12/2007 | Unger |
| 7,317,216 B2 | 1/2008 | Holm-Kennedy |
| 7,323,305 B2 | 1/2008 | Leamon et al. |
| 7,348,141 B2 | 3/2008 | French et al. |
| 7,361,472 B2 | 4/2008 | Yguerabide et al. |
| 7,463,353 B2 | 12/2008 | Yershov |
| 7,504,832 B2 | 3/2009 | Kandori et al. |
| 7,588,672 B2 | 9/2009 | Unger et al. |
| 7,599,060 B2 | 10/2009 | Hoshizaki et al. |
| 7,622,294 B2 | 11/2009 | Walt et al. |
| 7,630,227 B2 | 12/2009 | Tran |
| 7,649,358 B2 | 1/2010 | Toumazou et al. |
| 7,686,929 B2 | 3/2010 | Toumazou et al. |
| 7,687,260 B2 | 3/2010 | Gutekunst |
| 7,738,086 B2 | 6/2010 | Shepard et al. |
| 7,785,776 B2 | 8/2010 | Wittwer et al. |
| 7,785,785 B2 | 8/2010 | Pourmand et al. |
| 7,824,890 B2 | 11/2010 | Hoser et al. |
| 7,835,871 B2 | 11/2010 | Kain et al. |
| 7,842,457 B2 | 11/2010 | Berka et al. |
| 7,884,398 B2 | 2/2011 | Levon et al. |
| 7,888,013 B2 | 2/2011 | Miyahara et al. |
| 7,888,015 B2 | 2/2011 | Toumazou et al. |
| 7,906,072 B2 | 3/2011 | Unger et al. |
| 7,914,981 B2 | 3/2011 | Barany et al. |
| 7,932,034 B2 | 4/2011 | Esfandyarpour et al. |
| 7,948,015 B2 | 5/2011 | Rothberg et al. |
| 7,995,679 B2 | 8/2011 | Ranganathan et al. |
| 7,998,673 B2 | 8/2011 | French et al. |
| 8,012,756 B2 | 9/2011 | Pourmand et al. |
| 8,048,626 B2 | 11/2011 | Hassibi et al. |
| 8,119,345 B2 | 2/2012 | Weusten et al. |
| 8,158,359 B2 | 4/2012 | Leamon et al. |
| 8,306,757 B2 | 11/2012 | Rothberg et al. |
| 8,313,904 B2 | 11/2012 | El Gamal et al. |
| 8,313,907 B2 | 11/2012 | Pourmand et al. |
| 8,517,329 B2 | 8/2013 | Nash et al. |
| 8,518,329 B2 | 8/2013 | Hassibi et al. |
| 8,637,436 B2 | 1/2014 | Hassibi |
| 8,735,067 B2 | 5/2014 | Zhang et al. |
| 8,790,876 B2 | 7/2014 | Leamon et al. |
| 8,969,781 B2 | 3/2015 | Hassibi et al. |
| 8,999,724 B2 | 4/2015 | Holt et al. |
| 9,040,237 B2 | 5/2015 | Koo et al. |
| 9,133,504 B2 | 9/2015 | Hassibi et al. |
| 9,223,929 B2 | 12/2015 | Hassibi et al. |
| 9,341,589 B2 | 5/2016 | Hassibi et al. |
| 9,377,388 B2 | 6/2016 | Walt et al. |
| 9,458,497 B2 | 10/2016 | Hassibi et al. |
| 9,465,002 B2 | 10/2016 | Hassibi et al. |
| 9,499,861 B1 | 11/2016 | Hassibi et al. |
| 9,708,647 B2 | 7/2017 | Hassibi et al. |
| 9,983,163 B2 | 5/2018 | Hassibi et al. |
| 2001/0030290 A1 | 10/2001 | Stern |
| 2001/0046673 A1 | 11/2001 | French et al. |
| 2002/0001844 A1 | 1/2002 | Frutos et al. |
| 2002/0006619 A1 | 1/2002 | Cohen et al. |
| 2002/0034746 A1 | 3/2002 | McMillan et al. |
| 2002/0102567 A1 | 8/2002 | Fodor et al. |
| 2002/0106653 A1 | 8/2002 | Kurane et al. |
| 2002/0119462 A1 | 8/2002 | Mendrick et al. |
| 2002/0123048 A1 | 9/2002 | Gau |
| 2002/0131899 A1 | 9/2002 | Kovacs |
| 2002/0137096 A1 | 9/2002 | Fodor et al. |
| 2002/0146745 A1 | 10/2002 | Natan et al. |
| 2002/0150917 A1 | 10/2002 | Weidenhammer et al. |
| 2002/0177157 A1 | 11/2002 | Luo et al. |
| 2002/0187477 A1 | 12/2002 | Xue et al. |
| 2003/0040000 A1 | 2/2003 | Connolly et al. |
| 2003/0071843 A1 | 4/2003 | Hoff et al. |
| 2003/0130973 A1 | 7/2003 | Sumner et al. |
| 2003/0143591 A1 | 7/2003 | Davies et al. |
| 2003/0157581 A1 | 8/2003 | Grill et al. |
| 2003/0186310 A1 | 10/2003 | Kincaid |

(56) References Cited

U.S. PATENT DOCUMENTS

| | | |
|---|---|---|
| 2003/0194726 A1 | 10/2003 | Bolchakova et al. |
| 2003/0225718 A1 | 12/2003 | Shmulevich et al. |
| 2004/0002073 A1* | 1/2004 | Li et al. ............... C12Q 1/68 |
| 2004/0005582 A1 | 1/2004 | Shipwash et al. |
| 2004/0038420 A1 | 2/2004 | Gelbart et al. |
| 2004/0053254 A1 | 3/2004 | Wangh et al. |
| 2004/0058378 A1 | 3/2004 | Kong et al. |
| 2004/0077648 A1 | 4/2004 | Timmer et al. |
| 2004/0080629 A1 | 4/2004 | Sato et al. |
| 2004/0081974 A1 | 4/2004 | Gao |
| 2004/0086864 A1* | 5/2004 | Lo ............... C12Q 1/68 |
| | | 435/6 |
| 2004/0087033 A1 | 5/2004 | Schembri |
| 2004/0091862 A1 | 5/2004 | Brandenburg et al. |
| 2004/0096819 A1 | 5/2004 | McMillan et al. |
| 2004/0110219 A1 | 6/2004 | Buchholz et al. |
| 2004/0147045 A1 | 7/2004 | Nelson |
| 2004/0208792 A1 | 10/2004 | Linton et al. |
| 2004/0265902 A1 | 12/2004 | Fricker et al. |
| 2005/0003355 A1 | 1/2005 | Lu et al. |
| 2005/0064452 A1 | 3/2005 | Schmid et al. |
| 2005/0065290 A1 | 3/2005 | Shah |
| 2005/0084881 A1 | 4/2005 | Kelley et al. |
| 2005/0084884 A1 | 4/2005 | Palombella et al. |
| 2005/0089924 A1 | 4/2005 | Ho et al. |
| 2005/0112585 A1 | 5/2005 | Zichi et al. |
| 2005/0112634 A1 | 5/2005 | Woudenberg et al. |
| 2005/0161192 A1 | 7/2005 | Shigeura et al. |
| 2005/0202470 A1 | 9/2005 | Sundberg et al. |
| 2005/0238123 A1 | 10/2005 | Ranganathan et al. |
| 2005/0255516 A1 | 11/2005 | McMillan et al. |
| 2006/0014151 A1 | 1/2006 | Ogura et al. |
| 2006/0014200 A1 | 1/2006 | McMillan et al. |
| 2006/0024707 A1 | 2/2006 | Deans et al. |
| 2006/0051788 A1 | 3/2006 | Suzuki et al. |
| 2006/0068378 A1 | 3/2006 | Mirkin et al. |
| 2006/0078929 A1 | 4/2006 | Bickel et al. |
| 2006/0084069 A1 | 4/2006 | Chan et al. |
| 2006/0088844 A1 | 4/2006 | Xu |
| 2006/0094108 A1 | 5/2006 | Yoder et al. |
| 2006/0123516 A1 | 6/2006 | Ronen et al. |
| 2006/0140822 A1 | 6/2006 | Krysl et al. |
| 2006/0208254 A1 | 9/2006 | Goodman et al. |
| 2006/0269922 A1 | 11/2006 | Sagner et al. |
| 2006/0269934 A1 | 11/2006 | Woudenberg et al. |
| 2007/0010664 A1 | 1/2007 | Thomas et al. |
| 2007/0026421 A1 | 2/2007 | Sundberg et al. |
| 2007/0057159 A1 | 3/2007 | Hing |
| 2007/0065818 A1 | 3/2007 | Foti et al. |
| 2007/0077609 A1 | 4/2007 | Gambhir et al. |
| 2007/0099198 A1 | 5/2007 | Hassibi et al. |
| 2007/0212681 A1 | 9/2007 | Shapiro et al. |
| 2007/0218610 A1 | 9/2007 | Lim et al. |
| 2007/0279631 A1 | 12/2007 | Yershov |
| 2007/0281288 A1 | 12/2007 | Belkin et al. |
| 2008/0027008 A1 | 1/2008 | Henkin |
| 2008/0037008 A1 | 2/2008 | Shepard et al. |
| 2008/0039339 A1 | 2/2008 | Hassibi et al. |
| 2008/0081769 A1 | 4/2008 | Hassibi |
| 2008/0085839 A1 | 4/2008 | Klapproth |
| 2008/0176757 A1 | 7/2008 | Hassibi et al. |
| 2008/0305481 A1 | 12/2008 | Whitman et al. |
| 2009/0062134 A1 | 3/2009 | Linton et al. |
| 2009/0062152 A1 | 3/2009 | Linton et al. |
| 2009/0079414 A1 | 3/2009 | Levon et al. |
| 2009/0111207 A1 | 4/2009 | Choumane et al. |
| 2009/0137418 A1 | 5/2009 | Miller et al. |
| 2009/0143233 A1 | 6/2009 | Knight et al. |
| 2009/0143237 A1 | 6/2009 | Stender et al. |
| 2009/0156415 A1 | 6/2009 | Remacle et al. |
| 2009/0156425 A1 | 6/2009 | Walt et al. |
| 2009/0170728 A1 | 7/2009 | Walt et al. |
| 2009/0221025 A1 | 9/2009 | Huebner et al. |
| 2009/0318306 A1 | 12/2009 | Hasson et al. |
| 2009/0318307 A1 | 12/2009 | Garcia |
| 2009/0325164 A1 | 12/2009 | Vossenaar et al. |
| 2009/0325184 A1 | 12/2009 | Woudenberg et al. |
| 2010/0003715 A1 | 1/2010 | Pellegrino |
| 2010/0041030 A1 | 2/2010 | Hartwich |
| 2010/0105033 A1 | 4/2010 | Sun et al. |
| 2010/0122904 A1 | 5/2010 | Hassibi et al. |
| 2010/0129871 A1* | 5/2010 | Liu ............... C12P 19/34 |
| | | 435/91.1 |
| 2010/0137166 A1 | 6/2010 | Kain et al. |
| 2010/0138162 A1 | 6/2010 | Kain et al. |
| 2010/0233680 A1 | 9/2010 | Taylor et al. |
| 2010/0240544 A1 | 9/2010 | Liu et al. |
| 2010/0300899 A1 | 12/2010 | Levine et al. |
| 2010/0330578 A1 | 12/2010 | Duhr et al. |
| 2011/0009278 A1 | 1/2011 | Kain et al. |
| 2011/0009296 A1 | 1/2011 | Kain et al. |
| 2011/0086361 A1 | 4/2011 | Klunder et al. |
| 2011/0092692 A1 | 4/2011 | Jiang |
| 2011/0111968 A1 | 5/2011 | Okura et al. |
| 2011/0213252 A1 | 9/2011 | Fulghum |
| 2011/0236983 A1 | 9/2011 | Beechem et al. |
| 2011/0312810 A1 | 12/2011 | Moini et al. |
| 2012/0040853 A1 | 2/2012 | Pierik et al. |
| 2012/0052563 A1 | 3/2012 | Liang et al. |
| 2012/0077692 A1* | 3/2012 | Hassibi et al. ............ C40B 30/40 |
| 2012/0088682 A1 | 4/2012 | Rothberg et al. |
| 2012/0094298 A1 | 4/2012 | Seul et al. |
| 2012/0115214 A1 | 5/2012 | Battrell et al. |
| 2012/0164652 A1 | 6/2012 | Clemens et al. |
| 2012/0168306 A1 | 7/2012 | Hassibi et al. |
| 2012/0295805 A1 | 11/2012 | Levicky et al. |
| 2013/0045876 A1 | 2/2013 | Goel et al. |
| 2013/0210656 A1 | 8/2013 | Wangh et al. |
| 2013/0225441 A1 | 8/2013 | Hassibi |
| 2013/0252827 A1 | 9/2013 | Chun |
| 2013/0345065 A1 | 12/2013 | Hassibi et al. |
| 2014/0001341 A1 | 1/2014 | Hassibi et al. |
| 2014/0162266 A1 | 6/2014 | Klitgord et al. |
| 2014/0272978 A1 | 9/2014 | Shi et al. |
| 2014/0287420 A1 | 9/2014 | Cadle-Davidson |
| 2014/0287428 A1 | 9/2014 | Sietze |
| 2014/0318958 A1 | 10/2014 | Hassibi et al. |
| 2014/0363821 A1 | 12/2014 | Bashir et al. |
| 2015/0093849 A1 | 4/2015 | Shepard et al. |
| 2015/0125855 A1 | 5/2015 | Li et al. |
| 2016/0041095 A1 | 2/2016 | Rothberg et al. |
| 2016/0160271 A1 | 6/2016 | Hassibi et al. |
| 2016/0231270 A1 | 8/2016 | Hassibi et al. |
| 2017/0081714 A1 | 3/2017 | Hassibi et al. |
| 2017/0101666 A1 | 4/2017 | Hassibi et al. |
| 2017/0362648 A1 | 12/2017 | Hassibi et al. |
| 2018/0023129 A1 | 1/2018 | Hassibi et al. |
| 2018/0251828 A1 | 9/2018 | Hassibi et al. |
| 2018/0251829 A1 | 9/2018 | Hassibi et al. |
| 2018/0335399 A1 | 11/2018 | Hassibi et al. |
| 2019/0323070 A1 | 10/2019 | Hassibi et al. |
| 2020/0292457 A1 | 9/2020 | Hassibi et al. |

FOREIGN PATENT DOCUMENTS

| | | |
|---|---|---|
| CN | 1993617 A | 7/2007 |
| DE | 102014200483 A1 | 7/2015 |
| EP | 0684315 A1 | 11/1995 |
| EP | 0236069 B1 | 5/1997 |
| EP | 0872562 A1 | 10/1998 |
| EP | 1608952 A2 | 12/2005 |
| EP | 1681557 A1 | 7/2006 |
| EP | 1754257 A2 | 2/2007 |
| EP | 1924681 A2 | 5/2008 |
| EP | 2126765 A1 | 12/2009 |
| EP | 2374902 A1 | 10/2011 |
| EP | 2489745 A2 | 8/2012 |
| EP | 2029775 B1 | 10/2014 |
| WO | WO-0079009 A2 | 12/2000 |
| WO | WO-0121838 A2 | 3/2001 |
| WO | WO-0177372 A2 | 10/2001 |
| WO | WO-0186001 A1 | 11/2001 |
| WO | WO-0079009 A3 | 1/2002 |
| WO | WO-0230946 A1 | 4/2002 |

(56) References Cited

FOREIGN PATENT DOCUMENTS

| | | |
|---|---|---|
| WO | WO-02099397 A2 | 12/2002 |
| WO | WO-03062791 A2 | 7/2003 |
| WO | WO-2004011144 A2 | 2/2004 |
| WO | WO-03062791 A3 | 6/2004 |
| WO | WO-2004059006 A1 | 7/2004 |
| WO | WO-2005118870 A2 | 12/2005 |
| WO | WO-2005121159 A1 | 12/2005 |
| WO | WO-2006014351 A2 | 2/2006 |
| WO | WO-2006037527 A1 | 4/2006 |
| WO | WO-2006053769 A1 | 5/2006 |
| WO | WO-2007045755 A1 | 4/2007 |
| WO | WO-2007133703 A2 | 11/2007 |
| WO | WO-2007143669 A2 | 12/2007 |
| WO | WO-2008014485 A2 | 1/2008 |
| WO | WO-2008082713 A2 | 7/2008 |
| WO | WO-2008142571 A2 | 11/2008 |
| WO | WO-2008143646 A2 | 11/2008 |
| WO | WO-2009021054 A2 | 2/2009 |
| WO | WO-2009082706 A1 | 7/2009 |
| WO | WO-2009158451 A1 | 12/2009 |
| WO | WO-2011066186 A1 | 6/2011 |
| WO | WO-2013081987 A1 | 6/2013 |
| WO | WO-2013152203 A1 | 10/2013 |
| WO | WO-2014028061 A1 | 2/2014 |
| WO | WO-2016154227 A1 | 9/2016 |
| WO | WO-2017044100 A1 | 3/2017 |
| WO | WO-2017155858 A1 | 9/2017 |
| WO | WO-2018050501 A1 | 3/2018 |
| WO | WO-2020186252 A1 | 9/2020 |

OTHER PUBLICATIONS

Ansevin, et al. High-resolution thermal denaturation of DNA. I. Theoretical and practical considerations for the resolution of thermal subtransitions. Biopolymers. Jan. 1976;15(1):153-74.
Beaucage, et al. The functionalization of oligonucleotides via phosphoramidite derivative. Tetrahedron. 1993;49(10):1925-63.
Brill et al. Synthesis of oligodeoxynucleoside phosphorodithioates via thioamidites. J. Am. Chem. Soc. 111:2321-2322 (1989).
Brodsky, et al. Identification and handling of artifactual gene expression profiles emerging in microarray hybridization experiments. Nucleic Acids Res. Mar. 3, 2004;32(4):e46.
Cady, et al. Real-time PCR detection of Listeria monocytogenes using an integrated microfluidics platform. Sensors and Actuators B: Chemical. 2005; 107: 332-341.
Campbell, et al. Large-scale approaches for glycobiology. Genome Biology. 2005; 6(11):36.1-8.
Canon. High resolution thermal melt analysis. http://culs.canon.com/Science/Technology_Overview/High_Resolution_thermal_melt_analysis/High_Resolution_Thermal_Melt_Analysis.shtml. Accessed on Jun. 10, 2015. 1 pg.
Carlsson et al. Screening for genetic mutations. Nature 380(6571):207 (1996).
Clegg. Fluorescence resonance energy transfer and nucleic acids. Methods Enzymol. 1992;211:353-88.
Co-pending U.S. Appl. No. 16/191,836, filed Nov. 15, 2018.
Cronin, et al. Cystic fibrosis mutation detection by hybridization to light-generated DNA probe arrays. Hum Mutat. 1996;7(3):244-55.
De Mesmaeker et al. Comparison of Rigid and Flexible Backbones in Antisense Oligonucleotides Bioorg Med Chem Lett 4(3):395-398 (1994).
Dempcy et al. Synthesis of a thymidyl pentamer of deoxyribonucleic guanidine and binding studies with DNA homopolynucleotides PNAS USA 92:6097-6101 (1995).
Diehl et al. BEAMing: single-molecule PCR on microparticles in water-in-oil emulsions. Nature Methods 3(7):551-559 (2006).
Dolganov, et al. Novel molecular diagnostic (MDx) Platform for Highly-Multiplex Drug Susceptibility Testing of M. tuberculosis. http://www.stoptb.org/wg/new_diagnostics/assets/documents/09-NDWG-Annual-Meeting_GarySCHOOLNIK_&_Gregory_DOLGANOV.pdf. Accessed on Jun. 10, 2015. 13 pgs.
Dowling, et al. Exponential parameter estimation in the presence of known components and noise. Antennas and Propagation, IEEE Trans. on Antennas and Propag., 1994, 42(5):590-599.
Eltoukhy, et al. A 0.18-um CMOS bioluminescence detection lab-on-chip. Solid-State Circuits, IEEE Journal of: Mar. 2006; 41(3):651-662.
EP07784330.8 Search Report and Search Opinion dated Aug. 4, 2009.
EP12161041.4 Search Report and Search Opinion dated Nov. 5, 2012.
Falconnet, et al. Rapid, sensitive and real-time multiplexing platform for the analysis of protein and nucleic-acid biomarkers. Anal Chem. Feb. 3, 2015;87(3):1582-9. Epub Jan. 21, 2015.
FDA. Response to Section 501(k) Premarket Notification of Intent to Market. Re: K143178. Dated Jan. 30, 2015. 9 pages.
Feng, L. Probing lipid-protein interactions using lipid microarrays. Prostaglandins Other Lipid Mediat. 2005; 77(1-4):158-67.
Forster. Experimentelle und theoretische Untersuchung des zwischenmolekularen Übergangs von Elektronenanregungsenergie. Zeitschrift für naturforschung A 4.5 1949: 321-327.
Foss et al. Effects of fixative and fixation time on the extraction and polymerase chain reaction amplification of RNA from paraffin-embedded tissue. Comparison of two housekeeping gene mRNA controls. Diagn Mol Path 3:148-155 (1994).
Gao et al. Unusual conformation of a 3'-thioformacetal linkage in a DNA duplex. J. Biomolecular NMR.34:17-34 (1994).
Ginzinger. Gene quantification using real-time quantitative PCR: an emerging technology hits the mainstream. Exp Hematol. 2002; 30(6): 503-12.
Giordano, et al. Distinct transcriptional profiles of adrenocortical tumors uncovered by DNA microarray analysis. Am J Pathol. 2003; 162(2):521-531.
Guatelli et al. Isothermal, in vitro amplification of nucleic acids by a multienzyme reaction modeled after retroviral replication. PNAS USA 87(5):1874-1878 (1990).
Gunderson, et al.—Decoding Randomly Ordered DNA Arrays. Genome Res. 14:870-877, 2004.
Han, et al. Quantum-dot-tagged microbeads for multiplexed optical coding of biomolecules. Nature Biotechnology. 2001; 19, 631-635.
Hassibi. CMOS Biochips for Point-of-Care Molecular Diagnostics. Hot Chips—Aug. 2014. 32 pgs.
Hassibi, et al. A probabilistic model for inherent noise and systematic errors of microarrays. Proc of Workshop on Genomics Signal Processing and Statistics. 2005: 1-2.
Hassibi, et al. A Programmable 0.18-um CMOS Electrochemical Sensor Microarray for Biomolecular Detection. Sensors Journal, IEEE, Dec. 2006. vol. 6, Issue: 6: 1380-1388.
Hassibi, et al. A stochastic model and simulation algorithm for polymerase chain reaction (PCR) systems. Proc of Workshop on Genomics Signal Processing and Statistics. 2004: 1-4.
Hassibi, et al. Biological shot-noise and quantum-limited signal-to-noise ratio in affinity-based biosensors. J Appl Phys. 2005; 97: 084701.1-10.
Hassibi, et al. Effects of Scaling on the SNR and Speed of Biosensors. Engineering in Medicine and Biology Society, 2004. IEMBS'04. 26th Annual International Conference of the IEEE. vol. 1. IEEE, 2004.
Hassibi, et al. On noise processes and limits of performance in biosensors. J. Appl. Phys. 102, 014909 (2007) (12 pages).
Hassibi, et al. Real-time DNA microarray analysis. Nucleic Acids Res. Nov. 2009;37(20):e132. Epub Aug. 31, 2009.
Hassibi. Integrated Microarrays. Ph.D. Thesis Stanford University, 2005 (142 pgs).
Hauss. Electromagnetic nose and quantum optical measurements. Springer. NY 2000. Chap. 4. p. 127.
Held, et al. Modeling of DNA microarray data by using physical properties of hybridization. Proc Natl Acad Sci U S A. Jun. 24, 2003;100(13):7575-80. Epub Jun. 13, 2003.
Held, et al. Relationship between gene expression and observed intensities in DNA microarrays—a modeling study. Nucleic Acids Res. May 24, 2006;34(9):e70.

(56) References Cited

OTHER PUBLICATIONS

Horn et al. Oligonucleotides with alternating anionic and cationic phosphoramidate linkages: Synthesis and hybridization of stereo-uniform isomers. Tetrahedron Lett 37:743-746 (1996).
Howell, et al. iFRET: an improved fluorescence system for DNA-melting analysis. Genome Res. Sep. 2002;12(9):1401-7.
IDT—Integrated DNA Technologies. Strategies for Attaching Oligonucleotides to Solid Supports. Copyright 2014 (v3). Aug. 10, 2011. 7pages.
Jenkins et al. The Biosynthesis of Carbocyclic Nucleosides Chem Soc Re 24:169-176 (1995).
Jepsen, et al. Locked nucleic acid: a potent nucleic acid analog in therapeutics and biotechnology. Oligonucleotides. 2004;14(2):130-46.
Khabzaoui, et al. A multicriteria genetic algorithm to analyze microarray data. In Evolutionary Computation, Jun. 2004. CEC2004. Congress on vol. 2, pp. 1874-1881. IEEE.
Kiedrowski, et al. Parabolic growth of a self-replicating hexadeoxynucleotide bearing a 3'-5'-phosphoamidate linkage. Angew. Chem. Intl. Ed. English 1991;30:423-426.
Lalkhen, et al. Clinical tests: sensitivity and specificity. Continuing Education in Anaesthesia, Critical Care & Pain. 2008. 8(6), 221-223.
Landegren. Molecular mechanics of nucleic acid sequence amplification. Trends in Genetics, 1993, 9(6), 199-204.
Lee, et al. Seven-color, homogeneous detection of six PCR products. Biotechniques. Aug. 1999;27(2):342-9.
Letsinger et al. Cationic Oligonucleotides J Am Chem Soc 110:4470-4471 (1988).
Letsinger, et al. Hybridization of alternating cationic/anionic oligonucleotides to RNA segments. Nucleosides, Nucleotides & Nucleic Acids 13.6-7 (1994): 1597-1605.
Levine et al. Active CMOS Array for Electrochemical Sensing of Biomolecules, IEEE 2007 Custom Integrated Circuits Conference(CICC), pp. 826-828 (2007).
Li, et al. Bead-Based Melting Analysis in Temperature-Graident Microchannels for Single Nucleotide Polymorphisms Detection. 17th International Conference on Miniaturized Systems for Chemistry and Life Sciences. Oct. 27-31, 2013. Freiburg, Germany. 3 pages.
Lipsky, et al. DNA melting analysis for detection of single nucleotide polymorphisms. Clin Chem. Apr. 2001;47(4):635-44.
Liu, et al. TaqMan probe array for quantitative detection of DNA targets. Nucleic Acids Res. 2006; 34(1): e4. Published online Jan. 10, 2006.
Lizardi, et al. Exponential amplification of recombinant-RNA hybridization probes. Nature Biotechnology 6.10 (1988): 1197-1202.
Lockhart, et al. Multiplex metallica. Nat Biotechnol. Dec. 2001;19(12):1122-3.
Manickam, et al. A CMOS Electrochemical Impedance Spectroscopy (EIS) Biosensor Array. IEEE Trans Biomed Circuits Syst. Dec. 2010;4(6):379-90.
Marcy, et al. Innovative integrated system for real-time measurement of hybridization and melting on standard format microarrays. Biotechniques. Jun. 2008;44(7):913-20.
Margulies, et al. Genome sequencing in microfabricated high-density picolitre reactors. Nature. Sep. 15, 2005;437(7057):376-80. Epub Jul. 31, 2005.
Matsubara, et al. On-chip nanoliter-vol. multiplex TaqMan polymerase chain reaction from a single copy based on counting fluorescence released microchambers. Anal Chem. Nov. 1, 2004;76(21):6434-9.
Merrifield, R. B., "Solid-Phase Peptide Synthesis. III. An Improved Synthesis of Bradykinin," Biochemistry, vol. 3, 9, pp. 1385-1390, Sep. 1964.
Metzker. Sequencing technologies—the next generation. Nat Rev Genet. Jan. 2010;11(1):31-46. Epub Dec. 8, 2009.
Meuzelaar, et al. DNA diagnostics by surface-bound melt-curve reactions. J Mol Diagn. Feb. 2007;9(1):30-41.
Michael, et al. Randomly Ordered Addressable High-Density Optical Sensor Arrays. Anal. Chem., 1998; 70(7): 1242-1248.
Nanogen. A chip-based genetic detector for rapid identification of individuals. National institute of justice—Project No. 97-LB-VX-0004. Apr. 2006. 102 pgs.
Notice of Allowability dated Aug. 10, 2016 for U.S. Appl. No. 14/850,659.
Notice of allowance dated Jan. 15, 2016 for U.S. Appl. No. 13/527,742.
Notice of Allowance dated Apr. 26, 2017 for U.S. Appl. No. 14/665,904.
Notice of allowance dated May 1, 2013 for U.S. Appl. No. 13/417,661.
Notice of allowance dated May 31, 2016 for U.S. Appl. No. 13/240,603.
Notice of allowance dated Jun. 24, 2011 for U.S. Appl. No. 11/829,861.
Notice of allowance dated Jul. 10, 2015 for U.S. Appl. No. 11/758,621.
Notice of Allowance dated Jul. 14, 2016 from U.S. Appl. No. 14/850,659.
Notice of allowance dated Aug. 27, 2015 for U.S. Appl. No. 11/376,398.
Notice of allowance dated Sep. 23, 2013 for U.S. Appl. No. 11/844,996.
Notice of allowance dated Oct. 11, 2018 for U.S. Appl. No. 15/291,747.
Notice of allowance dated Nov. 3, 2014 for U.S. Appl. No. 13/535,665.
Notice of Allowance dated Jan. 31, 2018 for U.S. Appl. No. 13/873,684.
Office action dated Jan. 4, 2011 for U.S. Appl. No. 11/844,996.
Office action dated Jan. 7, 2016 for U.S. Appl. No. 13/240,603.
Office Action dated Feb. 1, 2017 for U.S. Appl. No. 14/665,904.
Office action dated Feb. 5, 2014 for U.S. Appl. No. 13/854,857.
Office Action dated Feb. 7, 2017 for U.S. Appl. No. 13/854,857.
Office action dated Feb. 13, 2013 for U.S. Appl. No. 11/376,398.
Office action dated Feb. 24, 2015 for U.S. Appl. No. 11/376,398.
Office action dated Feb. 26, 2016 for U.S. Appl. No. 13/959,492.
Office action dated Mar. 11, 2013 for U.S. Appl. No. 11/844,996.
Office action dated Mar. 15, 2016 for U.S. Appl. No. 14/850,659.
Office Action dated Apr. 3, 2017 for U.S. Appl. No. 14/822,737.
Office action dated Apr. 13, 2009 for U.S. Appl. No. 11/376,398.
Office action dated Apr. 22, 2013 for U.S. Appl. No. 13/527,742.
Office action dated May 11, 2010 for U.S. Appl. No. 11/844,996.
Office action dated May 21, 2015 for U.S. Appl. No. 11/376,398.
Office action dated May 27, 2014 for U.S. Appl. No. 11/376,398.
Office action dated May 30, 2013 for U.S. Appl. No. 11/376,398.
Office action dated Jun. 3, 2016 for U.S. Appl. No. 13/854,857.
Office action dated Jun. 11, 2012 for U.S. Appl. No. 13/417,661.
Office action dated Jun. 12, 2017 for U.S. Appl. No. 13/873,684.
Office action dated Jun. 15, 2009 for U.S. Appl. No. 11/758,621.
Office action dated Jul. 2, 2013 for U.S. Appl. No. 13/854,857.
Office action dated Jul. 3, 2012 for U.S. Appl. No. 11/844,996.
Office Action dated Jul. 19, 2016 from U.S. Appl. No. 14/665,904.
Office action dated Jul. 25, 2018 for U.S. Appl. No. 15/972,514.
Office action dated Jul. 28, 2014 for U.S. Appl. No. 13/535,665.
Office action dated Aug. 16, 2018 for U.S. Appl. No. 15/689,461.
Office action dated Aug. 16, 2018 for U.S. Appl. No. 15/972,517.
Office action dated Aug. 27, 2015 for U.S. Appl. No. 14/665,904.
Office action dated Aug. 28, 2015 for U.S. Appl. No. 13/240,603.
Office action dated Sep. 13, 2010 for U.S. Appl. No. 11/758,621.
Office action dated Sep. 20, 2011 for U.S. Appl. No. 11/758,621.
Office action dated Sep. 20, 2018 for U.S. Appl. No. 15/250,722.
Office action dated Oct. 9, 2014 for U.S. Appl. No. 13/854,857.
Office action dated Oct. 23, 2013 for U.S. Appl. No. 11/376,398.
Office Action dated Oct. 24, 2017 for U.S. Appl. No. 13/854,857.
Office action dated Nov. 6, 2016 for U.S. Appl. No. 13/873,684.
Office action dated Nov. 13, 2015 for U.S. Appl. No. 13/854,857.
Office action dated Nov. 13, 2018 for U.S. Appl. No. 14/822,737.
Office action dated Nov. 16, 2015 for U.S. Appl. No. 14/665,904.
Office action dated Nov. 20, 2012 for U.S. Appl. No. 13/417,661.
Office action dated Dec. 3, 2013 for U.S. Appl. No. 13/527,742.
Office action dated Dec. 7, 2010 for U.S. Appl. No. 11/829,861.
Office action dated Dec. 8, 2011 for U.S. Appl. No. 12/617,794.
Office action dated Dec. 28, 2009 for U.S. Appl. No. 11/376,398.

(56) References Cited

OTHER PUBLICATIONS

Office action dated Dec. 30, 2008 for U.S. Appl. No. 11/758,621.
Office action dated Dec. 31, 2013 for U.S. Appl. No. 13/535,665.
Parikh, et al. A CMOS Image Sensor for DNA Microarray, IEEE Custom Integrated Circuit Conf., 2007 26: 821-824.
Paska et al. Effect of formalin, acetone, and RNAlater fixatives on tissue preservation and different size amplicons by real-time PCR from paraffin-embedded tissue. Diagn Mol Path 13(4): 234-240 (2004).
PCT/US2007/070449 International Search Report and Written Opinion dated Mar. 3, 2008.
PCT/US2007/074644 International Search Report and Written Opinion dated Apr. 24, 2008.
PCT/US2007/076807 International search report and opinion dated Sep. 11, 2008.
PCT/US2015/049341 International Search Report and Written Opinion dated Jan. 28, 2016.
PCT/US2016/23634 International Search Report and Written Opinion dated Jul. 15, 2016.
PCT/US2017/020887 International Search Report and Written Opinion dated Jun. 5, 2017.
Petersson, et al. A review of the parameter estimation problem of fitting positive exponential sums to empirical data. Technical Report IMa-TOM-1997-08, Department of Mathematics and Physics. Malardalen University, Sweden. 1997: 1-29.
Petersson, et al. Applied Mathematics and Computation. Feb. 2002. vol. 126: No. 1. 31-61.
Pierik, et al. Rapid genotyping of human papillomavirus by post-PCR array-based hybridization techniques. J Clin Microbiol. Apr. 2011;49(4):1395-402. Epub Feb. 16, 2011.
Plummer, et al. Silicon Technologies: Fundamentals, Practices, and Modeling. Prentice Hall Electronics and VLSI Series, 2000.
Pont-Kindon, et al. Direct molecular haplotyping by melting curve analysis of hybridization probes: beta 2-adrenergic receptor haplotypes as an example. Nucleic Acids Res. Jun. 3, 2005;33(10):e89.
Pourmand, et al. Direct electrical detection of DNA synthesis. Proc Natl Acad Sci U S A. Apr. 25, 2006;103(17):6466-70. Epub Apr. 13, 2006.
Rant, et al. Switchable DNA interfaces for the highly sensitive detection of label-free DNA targets. Proc Natl Acad Sci U S A. Oct. 30, 2007;104(44):17364-9. Epub Oct. 19, 2007.
Reed, et al. High-resolution DNA melting analysis for simple and efficient molecular diagnostics. Pharmacogenomics. Jun. 2007;8(6):597-608.
Rehmna, et al. Immobilization of acrylamide-modified oligonucleotides by co-polymerization. Nucleic Acids Res. Jan. 15, 1999;27(2):649-55.
Reverter, et al. A rapid method for computationally inferring transcriptome coverage and microarray sensitivity. Bioinformatics. Jan. 1, 2005;21(1):80-9. Epub Aug. 12, 2004.
Ririe, et al. Product differentiation by analysis of DNA melting curves during the polymerase chain reaction. Anal Biochem. Feb. 15, 1997;245(2):154-60.
Rothberg, et al. An integrated semiconductor device enabling non-optical genome sequencing. Nature. Jul. 20, 2011;475(7356):348-52.
Rothberg et al., "The Development and Impact of 454 Sequencing," Nature Biotechnology, vol. 26, No. 10, pp. 1117-1124, Oct. 9, 2008.
Rothe, et al. Multi-target electrochemical biosensing enabled by integrated CMOS electronics. Journal of Micromechanics and Microengineering, 2011, 21(5), 054010.
Sakurai et al., "Real-Time Monitoring of DNA Polymerase Reactions by a Micro ISFET pH Sensor," Anal. Chem., 64, No. 17, pp. 1996-1997, Sep. 1, 1992.
Salm, et al. Ultralocalized thermal reactions in subnanoliterdroplets-in-air. Proc Natl Acad Sci U S A. Feb. 26, 2013;110(9):3310-5. Epub Feb. 11, 2013.
Sanchez, et al. Linear-after-the-exponential (LATE)-PCR: an advanced method of asymmetric PCR and its uses in quantitative real-time analysis. Proc Natl Acad Sci U S A. Feb. 17, 2004;101(7):1933-8. Epub Feb. 9, 2004.
Sanghvi, et al. Chapters 6 and 7, ASC Symposium Series 580, "Carbohydrate Modifications in Antisense Research", 1994.
Sanghvi, et al. ed. Chapters 2 and 3, ASC Symposium Series 580—Carbohydrates Modifications in Antisense Research. American Chemical Society. Washington, DC. 1994.
Savyon Diagnostics. Nano CHIP, www.nanochip400.com. NG Jun. 2010—VER1. 8pgs.
Schena, et al. Quantitative monitoring of gene expression patterns with a complementary DNA microarray. Science. Oct. 20, 1995;270(5235):467-70.
Scherf, et al. Letter from Uwe Scherf-S to Kristen Kanack re: K143178 Section 510(k). Department of Health & Human Services. Jan. 30, 2015. 9pgs.
Schienle, et al. A fully electronic DNA sensor with 128 positions and in-pixel A/D conversion. IEEE Journal of vol. 39, Issue 12, Dec. 2004 pp. 2438-2445.
Singh, et al. A CMOS-Microfluidic Chemiluminescence Contact Imaging Microsystem. IEEE Journal of Solid-State Circuits. Nov. 2012;47(11) 2822-33.
Singh et al. A Compact Parasitic-Insensitive Dual-Frequency $\Delta\Sigma$ Modulated CMOS Capacitive Architecture, IEEE, pp. 242-245 (2010).
Singh. High Dynamic Range CMOS-Integrated Biosensors. https://repositories.lib.utexas.edu/bitstream/handle/2152/29144/SINGH-DISSERTATION-2013.pdf?sequence=1. May 1, 2013. Accessed on Feb. 11, 2016. 189 pages.
Soon, et al. High Throughput Melting Curve Analysis In Monolithic Silicon-Based Microfluidic Device. 14th International Conference on Miniaturized Systems for Chemistry and Life Sciences. Oct. 3-7, 2010. Groningen, The Netherlands.
Sosnowski. A chip-based genetic detector for rapid identification of individuals. Document No. 213911. Award No. 1997-LB-XV-0004. Apr. 2006. 100 pages.
Stillman, et al. FAST slides: a novel surface for microarrays. Biotechniques. Sep. 2000;29(3):630-5.
Stimpson, et al. Real-time detection of DNA hybridization and melting on oligonucleotide arrays by using optical wave guides. Proc Natl Acad Sci U S A. Jul. 3, 1995;92(14):6379-83.
Stochastic Matrix, one page, 2013. Wolfram MathWorld. Obtained online on May 29, 2013.
Stolovitzky, et al. Efficiency of DNA replication in the polymerase chain reaction. Proc Natl Acad Sci USA. 1996; 93: 12947-52.
Stoughton. Applications of DNA microarrays in biology. Annu Rev Biochem. 2005;74:53-82.
Tang, et al. Simple and effective method for generating single-stranded DNA targets and probes. Biotechniques. Jun. 2006;40(6):759-63.
Temiz et al. Robust Microelectrodes Developed for Improved Stability in Electrochemical Characterization of Biomolecular Layers, IEEE Sensors 2010 Conference, pp. 1051-1055 (2010).
Tijssen. Ch 2—Overview of principles of hybridization and the strategy of nucleic acid assays. Techniques in Biochemistry and Molecular Biology: Hybridization with Nucleic Acid Probes. Elsevier Science Publisher, Netherlands. 1993. 70 pages.
Tijssen. Chapter 3 of Laboratory Techniques in Biochemistry and Molecular Biology: Hybridization with Nucleic Acid Probes, Part I. Theory and Nucleic Acid Preparation. Elsevier, N.Y. 1993.
Tijssen. Overview of principles of hybridization and the strategy of nucleic acid probe assays. Laboratory techniques in biochemistry and molecular biology. 1993. 24: 19-78.
Tolley, et al. Single-chain polymorphism analysis in long QT syndrome using planar waveguide fluorescent biosensors. Anal Biochem. Apr. 15, 2003;315(2):223-37.
Tomlinson, et al. Influence of the length of target DNA overhang proximal to the array surface on discrimination of single-base mismatches on a 25-mer oligonucleotide array. BMC Res Notes. Apr. 17, 2014;7:251.

(56) References Cited

OTHER PUBLICATIONS

Tsuji et al. Development of a Time-Resolved Fluorometric Method for Observing Hybridization in Living Cells Using Fluorescence Resonance Energy Transfer. Biophysical Journal, Jul. 2001, 81:501-515.

Tu, et al. Quantitative noise analysis for gene expression microarray experiments. Proc Natl Acad Sci U S A. Oct. 29, 2002;99(22):14031-6. Epub Oct. 18, 2002.

Van Der Veen, et al. Subspace-based signal analysis using singular value decomposition. Proceedings of the IEEE, 1993, 81(9), 1277-1308.

Vikalo, et al. A statistical model for microarrays, optimal estimation algorithms, and limits of performance. Signal Processing, IEEE Transactions on, 2006, 54(6), 2444-2455.

Vikalo, et al. Optimal estimation of gene expression levels in microarrays. Presented at the IEEE Int. Workshop Genomic Signal Processing Statistics, Newport, RI, May 22-24, 2005.

Vikalo, et al. Proof of publication date of [Vikalo et al. Optimal estimation of gene expression in microarrays.] as Mar. 5, 2005, one page, acquired from USPTO Library on Jun. 13, 2014.

Wang, et al. Estimation of the mutation rate during error-prone polymerase chain reaction. J Comput Biol. 2000; 7(1-2): 143-58.

Wittwer, et al. Continuous fluorescence monitoring of rapid cycle DNA amplification. Biotechniques. Jan. 1997;22(1):130-8.

Yuen, et al. Accuracy and calibration of commercial oligonucleotide and custom cDNA microarrays. Nucleic Acids Res. May 15, 2002;30(10):e48.

Zhang. Noisy Data with Outliers, one page, 1996. Obtained online on Feb. 9, 2013.

Zhu, et al. Multiplex asymmetric PCR-based oligonucleotide microarray for detection of drug resistance genes containing single mutations in Enterobacteriaceae. Antimicrob Agents Chemother. Oct. 2007;51(10):3707-13. Epub Jul. 23, 2007.

Zhu, et al. Protein chip technology. Current Opinion in Chemical Biology. 2003; 7: 55-63.

A. Agah, et al., A High-Resolution Low-Power Incremental Lb. ADC With Extended Range for Biosensor Arrays, IEEE Journal of Solid-State Circuits, vol. 45, No. 6, pp. 1099-1110 (2010) (Year: 2010).

A. Hassibi et al., 2018. Multiplexed identification, quantification and genotyping of infectious agents using a semiconductor biochip. Nature biotechnology, 36(8), p. 738.

Brown, et al. Exploring the new world of the genome with DNA microarrays. Nature Genet. 1999; 21 (Suppl.):33-37.

C. Y. Huang, Design of a voltammetry potentiostat for biochemical sensors, Analog Integr. Cir. Sig. Process, vol. 67, pp. 375-381 (2011) (Year: 2011).

Co-pending U.S. Appl. No. 16/670,126, inventors HassibiArjang et al., filed Oct. 31, 2019.

Co-pending U.S. Appl. No. 16/777,051, inventors HassibiArjang et al., filed Jan. 30, 2020.

Co-pending U.S. Appl. No. 16/983,989, inventors HassibiArjang et al., filed Aug. 3, 2020.

Co-pending U.S. Appl. No. 17/018,036, inventors HassibiArjang et al., filed Sep. 11, 2020.

Didenko. DNA probes using fluorescence resonance energy transfer (FRET): designs and applications. Biotechniques. Nov. 2001;31(5):1106-16, 1118, 1120-1.

El Gamal, A., Dec. 2002. Trends in CMOS image sensor technology and design. In Digest. International Electron Devices Meeting, (pp. 805-808). IEEE.

El Gamal, et al. CMOS image sensors. Circuits and Devices Magazine, IEEE. 2005; 20(3):6-20.

Field, R.M., Realov, S. and Shepard, K.L., 2014. A 100 fps, time-correlated single-photon-counting-based fluorescence-lifetime imager in 130 nm CMOS. IEEE Journal of Solid-State Circuits, 49(4), pp. 867-880.

Fossum, E.R. and Hondongwa, D.B., 2014. A review of the pinned photodiode for CCD and CMOS image sensors. IEEE J. Electron Devices Soc., 2(3), pp. 33-43.

Hagan, A. K., & Zuchner, T. (2011). Lanthanide-based time-resolved luminescence immunoassays. Analytical and bioanalytical chemistry, 400(9), 2847-64.

Huang, et al. A Single-Frame Superresolution Algorithm for Lab-on-a-Chip Lensless Microfluidic Imaging. IEEE Design &Test. Dec. 2015. 32(6):32-40. doi: 10.1109/MDAT.2015.2424418.

"Insulator (eletricity)" from Wikipedia, the free encyclopedia. Printed on Dec. 13, 2018.

Lai et al. PrimRglo: A multiplexable quantitative real-time polymerase chain reaction system for nucleic acid detection. Analytical Biochemistry 422:89-95 (2012).

Liu, et al., Biosensing based upon molecular confinement in metallic nanocavity arrays. Proceedins of SPIE 5703. Plasmonics in biology and medicine II, Mar. 31, 2005, pp. 99-106.

Lund-Olesen, et al., Sensitive on-chip quantitative real-time PCR performed on an adaptable and robust platform. Biomed Microdevices. Dec. 2008;10(6):769-776. doi: 10.1007/s10544-008-9189-0.

M. Stanacevic, VLSI Potentiostat Array with Oversampling Gain Modulation for Wide-Range Neurotransmitter Sensing IEEE Transactions on Biomedical Circuits and Systems, vol. 1, No. 1, pp. 63-72 (2007) (Year: 2007).

Manickam, et al., A Fully Integrated CMOS Fluorescence Biochip for DNA and RNA Testing. IEEE Journal of solid-state circuits, Nov. 2017; 52(11): 2857-2870.

Moore, E.G., Samuel, A.P. and Raymond, K.N., 2009. From antenna to assay: lessons learned in lanthanide luminescence. Accounts of chemical research, 42(4), pp. 542-552.

Murari, K., Etienne-Cummings, R., Thakor, N. and Cauwenberghs, G., 2009. Which photodiode to use: A comparison of CMOS-compatible structures. IEEE sensors journal, 9(7), pp. 752-760.

Namasivayam et al., Advances in on-chip photodetection for applications in miniaturized genetic analysis systems, Journal ofv Micrornechanics and Microengineering vol. 14, issue 1, p. 81-90, Published Aug. 18, 2003.

Novak, et al., An integrated fluorescence detection system for lab-on-a-chip applications. Lab on a chip, royal society of chemistry. Nov. 2006; 7(1):27-29.

P. M. Levine, et al., Active CMOS Sensor Array for Electrochemical Biomolecular Detection, IEEE Journal of Solid-State Circuits, vol. 43, No. 8, pp. 1859-1871 (2008) (Year: 2009).

Potrich, Cristina, et al., On chip micro-extraction and real-time PCR with integrated SPAD optical fluorescence detection for nucleic acid analysis. Lab-on-a-chip European Congress. 2011.

S. Hwang, et al., CMOS Microelectrode Array for Electrochemical Lab-on-a-Chip Applications, IEEE Sensors Journal, vol. 9, No. 6, pp. 609-615 (2009) (Year: 2009).

Schwartz, D.E., Charbon, E. and Shepard, K.L., 2008. A single-photon avalanche diode array for fluorescence lifetime imaging microscopy. IEEE journal of solid-state circuits, 43(11), pp. 2546-2557.

Selvin, P.R., 2002. Principles and biophysical applications of lanthanide-based probes. Annual review of biophysics and biomolecular structure, 31(1), pp. 275-302.

Selvin, P.R., "Lanthanide-Labeled DNA", (2003) Topics in Fluorescence Spectroscopy, vol. 7: DNA Technology, Chapter 6, Kluwer Academic.

Seo, Min-Woong, et al,. A 10 ps time-resolution CMOS image sensor with two-tap true-CDS lock-in pixels for fluorescence lifetime imaging. IEEE Journal of soli-state circuits 51.1 (2015): 142-154.

Singh, et al., CMOS biochips for hypothesis-driven DNA analysis. IEEE Biomedical circuits and systems conference. Oct. 2014.

Tao, et al., Blocking oligo—a novel approach for improving chip-based DNA hybridization efficiency. Mol Cell Probes. Aug. 2003;17(4):197-202.

Tokuda et al., A CMOS image sensor with optical and potential dual imaging function for on-chip bioscientific applications, Sensors and Actuators A: Physical, vol. 125, Issue 2, Jan. 10, 2006, pp. 273-280.

Walczak, et al., Miniaturized System for Real-Time PCR in Low-Cost Disposable LTCC Chip With Integrated Optical Waveguide. 12th international conference on miniaturized systems for chemistry and life sciences. 2008; 1078-1080.

(56) References Cited

OTHER PUBLICATIONS

Wilhelm, et al., Real-time polymerase chain reaction. Chembiochem, 2003;4:1120-1128.
You, et al., Measuring thermodynamic details of DNA hybridization using fluorescence, Biopolymers, vol. 95, 2011; pp. 472-486.
Yuan, J. and Wang, G., 2006. Lanthanide-based luminescence probes and time-resolved luminescence bioassays. TrAC Trends in Analytical Chemistry, 25(5), pp. 490-500.
Supplementary Information from Rothberg et al.,An Integrated Semiconductor Device Enabling Non-Optical Genome Sequencing. Nature, 475, 348-352, Jul. 21, 2011.
The definition for "ionic current". Printed on Oct. 20, 2021.
The definition for "photodiodes". Printed on Oct. 20, 2021.
The definition of "Electrical Impedance" from Wikipedia. Printed on Oct. 20, 2021.
Co-pending U.S. Appl. No. 17/558,084, inventors Hassibi; Arjang et al., filed Dec. 21, 2021.

\* cited by examiner

| Oligo Name | Sequence |
|---|---|
| Target-WT | 5'- AGC CAG CCG AGC CAA TTC ATG TTC CAG AAC AAC CCG CTG TCG GGG TTG ACC TAC AAG CGC CGA CTG TCG GCG CTG GGG CCC GGC -3' |
| Target-MT | 5'- AGC CAG CTG AGC CAA TTC ATG GAC CAG AAC AAC CCG CTG TCG GGG TTG ACC CAC AAG CGC CGA CTG TCG GCG CTG GGG CCC GGC -3' |
| Probe_WT | 5-NH2-C9-CCG ACA GCG GGT TGT –FAM– TC TGG AA-3' |
| Probe_MT | 5-NH2-C9-CCG ACA GCG GGT TGT –FAM– TC TGG TC-3' |

*FIG. 4*

NUCLEIC ACID SEQUENCE IDENTIFICATION USING SOLID-PHASE CYCLIC SINGLE BASE EXTENSION

CROSS-REFERENCE

This application is a continuation of International Patent Application No. PCT/US2017/020887, filed Mar. 6, 2017, which claims priority to U.S. Provisional Patent Application No. 62/304,859, filed Mar. 7, 2016, each of which is entirely incorporated herein by reference.

SEQUENCE LISTING

The instant application contains a Sequence Listing which has been submitted electronically in ASCII format and is hereby incorporated by reference in its entirety. Said ASCII copy, created on Mar. 27, 2017, is named 42500-719_601_SL.txt and is 1,817 bytes in size.

BACKGROUND

Identifying specific short nucleic acid sequences, for example a single nucleotide polymorphism (SNP) or insertion-deletion, at a known location within a DNA fragment or RNA transcript can be of great importance in genomics and related applied fields such as pharmacogenomics, molecular diagnostics, personalized medicine, etc. Such information, if acquired accurately, can be used for genotyping organisms and for classifying their behavior and function. Point mutations present in a DNA fragment or RNA transcript can result in various diseases and disorders, including, but not limited to, cystic fibrosis; cancer, including breast cancer; neurofibromatosis; sickle-cell anemia; and Tay-Sachs disease. A large number of solid tumor cancers can be caused by single point mutations or small base pair insertions/deletions in susceptible genes. Currently, there are various methods for genotyping samples comprising nucleic acid sequences. These methods include DNA microarrays, quantitative polymerase chain reaction processes such as allele-specific PCR, and DNA sequencing such as next-generation sequencing.

A general challenge in nucleic acid sequence identification and genotyping is the presence of background nucleic acid sequences which can interfere with the identification and result in error. The induced errors originating from background nucleic acid sequences can generally increase with two factors—1) significant sequence similarity between the background material and the target sequence and 2) low concentrations of target sequence in the presence of high concentrations of genomic background. For example, these two factors can make detection of a target sequence from a sample obtained from a biopsy procedure in DNA-based cancer diagnostics challenging. In a sample obtained from a biopsy, the number of cancerous cells from which target "mutated" sequences may be derived may be present as only a fraction of the cells of the sample. Additionally, the mutations in cancerous cells can be subtle and may include only a handful of single nucleotide polymorphisms (SNPs) or insertion-deletions (indels), resulting in significant sequence similarity between the background material and the target sequence.

SUMMARY

As recognized herein, the ability to detect low level mutations from among mostly wild-type nucleic acids, such as deoxyribonucleic acids (DNA), may be very useful in areas such as cancer detection, prenatal testing, and infectious diseases.

The present disclosure provides methods and systems of detecting low level mutations in nucleic acids, such as DNA comprising mostly wild-type sequences. Methods and systems of the present disclosure may be useful in various contexts, such as disease (e.g., cancer) detection, prenatal testing and infectious diseases.

In an aspect, a method for detecting a presence of a nucleic acid molecule having a nucleic acid sequence in a biological sample of a subject comprises (a) bringing a solution comprising the biological sample in contact with an array of probes on a solid support, wherein the array of probes has sequence complementarity to the nucleic acid sequence, and wherein at most a subset of the array of probes hybridizes to the nucleic acid molecule if the nucleic acid molecule is present in the biological sample; (b) subjecting the array of probes to an elongation reaction under conditions that are sufficient to elongate the subset of the probes hybridized to the nucleic acid molecule having the nucleic acid sequence, to yield elongation product(s) coupled to the solid support; (c) detecting a signal or a signal change indicative of a presence of the elongation product(s); (d) subjecting the array of probes to denaturing conditions that are sufficient to denature the elongation product(s) to yield the nucleic acid molecule in the solution, wherein subsequent to subjecting the array of probes to denaturing conditions, the subset of the probes is unavailable for subsequent elongation; and (e) repeating (a)-(d), thereby detecting the presence of the nucleic acid molecule having the nucleic acid sequence in the biological sample of the subject. In some embodiments, the nucleic acid sequence is present in the nucleic acid molecule, and wherein in (a), a subset but not all of the array of probes hybridizes to the nucleic acid molecule having the nucleic acid sequence. In some embodiments, the elongation product(s) includes the subset of the array of probes and at least one nucleotide coupled thereto, wherein the at least one nucleotide is complementary to the nucleic acid molecule. In some embodiments, the nucleic acid molecule is single stranded. In some embodiments, the array of probes includes individually addressable locations. In some embodiments, the nucleic acid sequence comprises a genomic variant. In some embodiments, the solid support comprises a sensor array, which sensor array comprises a sensor that detects the signal or the signal change indicative of the presence of the elongation product(s). In some embodiments, each probe in the array of probes comprises a fluorophore. In some embodiments, the fluorophore is a fluorescent moiety. In some embodiments, the elongation reaction comprises i) bringing the array of probes in contact with a polymerizing enzyme and nucleotides, and ii) using the polymerizing enzyme to incorporate at least one of the nucleotides in a given one of the probes to yield the elongation product(s). In some embodiments, the nucleotides comprise tags. In some embodiments, the tags are quenchers. In some embodiments, the nucleotides are inhibitors of the polymerizing enzyme. In some embodiments, the nucleotides are dideoxynucleotides (ddNTPs). In some embodiments, the polymerizing enzyme is thermostable. In some embodiments, the polymerizing enzyme lacks 3'-5' exonuclease activity. In some embodiments, the array of probes comprises a fluorophore and the nucleotides comprise quenchers. In some embodiments, the signal or the signal change includes a decrease in fluorescence from the array of probes resulting from the incorporation of the nucleotides comprising quenchers. In some embodiments, the detecting is in the absence of Forster resonance energy transfer (FRET). In some embodiments, detecting the signal or the signal change comprises detecting a presence or an increase in a signal relative to a reference. In some embodiments, detecting the signal or the signal change comprises detecting an absence or a decrease in a signal relative to a reference. In some embodiments, detecting the signal or the signal change occurs in real-time. In some embodiments, the probes have lengths of at least about 5 nucleic acid bases. In some embodiments, the denaturing conditions include an increase in temperature. In some embodiments, the increase in temperature is a temperature increase above 80° C. In some embodiments, the increase in temperature is a temperature increase above 85° C.

Another aspect provides a method for detecting a presence of a nucleic acid sequence in a biological sample of a subject, the biological sample comprising nucleic acid molecules. The method comprises (a) bringing a solution comprising the biological sample in contact with an array of probes on a solid support, wherein the array of probes has sequence complementarity to the nucleic acid sequence, wherein the nucleic acid molecules having the nucleic acid sequence are at a concentration of less than about 10% in the solution, and wherein at most a subset of the array of probes hybridizes to the nucleic acid molecules having the nucleic acid sequence if the nucleic acid molecules are present in the biological sample; (b) subjecting the array of probes to an elongation reaction under conditions that are sufficient to elongate the subset of the array of probes hybridized to the nucleic acid molecules having the nucleic acid sequence to yield elongation product(s) coupled to the solid support; (c) detecting a signal or a signal change indicative of a presence of the elongation product(s); (d) subjecting the array of probes to denaturing conditions that are sufficient to denature the elongation product(s) to yield the nucleic acid molecules in the solution; and (e) repeating (a)-(d), thereby detecting the presence of the nucleic acid sequence. In some embodiments, the concentration is less than 5% of the solution. In some embodiments, the concentration is less than 1% of the solution. In some embodiments, the nucleic acid sequence is detected at a sensitivity of at least about 90%. In some embodiments, the sensitivity is at least about 95%. In some embodiments, the sensitivity is at least about 99%. In some embodiments, the nucleic acid sequence is detected at a sensitivity of at least about 90% upon repeating (a)-(d) at least 5 times. In some embodiments, the nucleic acid sequence is detected at a sensitivity of at least about 95% upon repeating (a)-(d) at least 5 times. In some embodiments, the nucleic acid sequence is detected at a sensitivity of at least about 90% upon repeating (a)-(d) at least 10 times.

In another aspect, a method for quantifying a concentration of nucleic acid molecule(s) having a nucleic acid sequence in a biological sample of a subject comprises (a) bringing a solution comprising the biological sample in contact with an array of a set of probes on a solid support, wherein the set of probes has sequence complementarity to the nucleic acid sequence, and wherein at most a subset of the set of probes hybridizes to the nucleic acid molecule(s) having the nucleic acid sequence if the nucleic acid molecule(s) is present in the biological sample; (b) subjecting the array to an elongation reaction under conditions that are sufficient to elongate the subset of the set of probes hybridized to the nucleic acid molecules having the nucleic acid sequence to yield elongation product(s) coupled to the solid support; (c) detecting a signal or a signal change indicative of a presence of the elongation product(s); (d) subjecting the array to denaturing conditions that are sufficient to denature the elongation product(s) to yield the biological sample in the solution; and (e) repeating (a)-(d) until a net signal or a net signal change exceeds a predetermined threshold, thereby quantifying the concentration of the nucleic acid molecule(s) having the nucleic acid sequence in the biological sample of the subject. In some embodiments, the number of times (a)-(d) are repeated to reach the predetermined threshold is used to quantify the concentration. In some embodiments, the concentration is quantified at an accuracy of at least 90%. In some embodiments, the accuracy is at least 95%. In some embodiments, the concentration is quantified at a sensitivity of at least 90%. In some embodiments, the sensitivity is at least 95%. In some embodiments, the predetermined threshold of the net signal or the net signal change is at least a 25% decrease relative to a reference. In some embodiments, the predetermined threshold of the net signal or the net signal change is at least a 50% decrease relative to the reference. In some embodiments, the predetermined threshold of the net signal or the net signal change is at least a 25% increase relative to a reference. In some embodiments, the predetermined threshold of the net signal or the net signal change is at least a 50% increase relative to the reference. In some embodiments, the method comprises quantifying a concentration of an additional nucleic acid molecule(s) having an additional nucleic acid sequence in the biological sample. In some embodiments, the concentration of the additional nucleic acid molecule(s) having the additional nucleic acid sequence is quantified in parallel with quantifying the concentration of nucleic acid molecule(s). In some embodiments, the additional nucleic acid sequence and an additional set of probes having sequence complementarity to the additional nucleic acid sequence has a hybridization thermodynamic property similar to the nucleic acid sequence and the set of probes having sequence complementarity to the nucleic acid sequence. In some embodiments, the hybridization thermodynamic property is melting temperature.

In another aspect, a system for detecting a presence of a nucleic acid molecule having a nucleic acid sequence in a biological sample of a subject, comprises: a sensor comprising an array of probes on a solid support, wherein the array of probes has sequence complementarity to the nucleic acid sequence; and a controller operatively coupled to the sensor, wherein the controller is programmed to: (a) bring a solution comprising the biological sample in contact with the array of probes, wherein at most a subset of the array of probes hybridizes to the nucleic acid molecule if the nucleic acid molecule is present in the biological sample; (b) subject the array of probes to an elongation reaction under conditions that are sufficient to elongate the subset of the array of probes hybridized to the nucleic acid molecule having the nucleic acid sequence, to yield elongation product(s) coupled to the solid support; (c) detect a signal or a signal change indicative of a presence of the elongation product(s); (d) subject the array of probes to denaturing conditions that are sufficient to denature the elongation product(s) to yield the nucleic acid molecule in the solution, wherein subsequent to subjecting the array of probes to denaturing conditions, the subset of the array of probes is unavailable for subsequent elongation; and (e) repeat (a)-(d), thereby detecting the presence of the nucleic acid molecule having the nucleic acid sequence in the biological sample of the subject. In some embodiments, the sensor further comprises a detector that is configured to detect the signal or signal change.

In another aspect, a system for detecting a presence of a nucleic acid sequence in a biological sample of a subject, the biological sample comprising nucleic acid molecules, comprises: a sensor comprising an array of probes on a solid support, wherein the array of probes has sequence complementarity to the nucleic acid sequence; and a controller operatively coupled to the sensor, wherein the controller is programmed to: (a) bring a solution comprising the biological sample in contact with the array of probes, wherein the nucleic acid molecules having the nucleic acid sequence are at a concentration of less than about 10% in the solution, and wherein at most a subset of the array of probes hybridizes to the nucleic acid molecules having the nucleic acid sequence if the nucleic acid molecules are present in the biological sample; (b) subject the array of probes to an elongation reaction under conditions that are sufficient to elongate the subset of the array of probes hybridized to the nucleic acid molecules having the nucleic acid sequence to yield elongation product(s) coupled to the solid support; (c) detect a signal or a signal change indicative of a presence of the elongation product(s); (d) subject the array of probes to denaturing conditions that are sufficient to denature the elongation product(s) to yield the nucleic acid molecules in the solution; and (e) repeat (a)-(d), thereby detecting the presence of the nucleic acid sequence. In some embodiments, the sensor further comprises a detector that is configured to detect the signal or signal change.

In another aspect, a system for quantifying a concentration of nucleic acid molecule(s) having a nucleic acid sequence in a biological sample of a subject, comprises: a sensor comprising an array of a set of probes on a solid support, wherein the set of probes has sequence complementarity to the nucleic acid sequence; and a controller operatively coupled to the sensor, wherein the controller is programmed to: (a) bring a solution comprising the biological sample in contact with the array, wherein at most a subset of the set of probes hybridizes to the nucleic acid molecule(s) having the nucleic acid sequence if the nucleic acid molecule(s) is present in the biological sample; (b) subject the array to an elongation reaction under conditions that are sufficient to elongate the subset of the set of probes hybridized to the nucleic acid molecule(s) having the nucleic acid sequence, to yield elongation product(s) coupled to the solid support; (c) detect a signal or a signal change indicative of a presence of the elongation product(s); (d) subject the array to denaturing conditions that are sufficient to denature the elongation product(s) to yield the biological sample in the solution; and (e) repeat (a)-(d) until a net signal or a net signal change exceeds a predetermined threshold, thereby quantifying the concentration of the nucleic acid molecule(s) having the nucleic acid sequence in the biological sample of the subject. In some embodiments, the sensor further comprises a detector that is configured to detect the signal or signal change.

In another aspect, a non-transitory computer-readable medium comprising machine-executable code that, upon execution by one or more computer processors, implements a method for detecting a presence of a nucleic acid molecule having a nucleic acid sequence in a biological sample of a subject, the method comprising: (a) bringing a solution comprising the biological sample in contact with an array of probes on a solid support, wherein the array of probes has sequence complementarity to the nucleic acid sequence, and wherein at most a subset of the array of probes hybridizes to the nucleic acid molecule if the nucleic acid molecule is present in the biological sample; (b) subjecting the array of probes to an elongation reaction under conditions that are sufficient to elongate the subset of the array of probes hybridized to the nucleic acid molecule having the nucleic acid sequence, to yield elongation product(s) coupled to the solid support; (c) detecting a signal or a signal change indicative of a presence of the elongation product(s); (d) subjecting the array of probes to denaturing conditions that are sufficient to denature the elongation product(s) to yield the nucleic acid molecule in the solution, wherein subsequent to subjecting the array of probes to denaturing conditions, the subset of the array of probes is unavailable for subsequent elongation; and (e) repeating (a)-(d), thereby detecting the presence of the nucleic acid molecule having the nucleic acid sequence in the biological sample of the subject.

In another aspect, a non-transitory computer-readable medium comprising machine-executable code that, upon execution by one or more computer processors, implements a method for detecting a presence of a nucleic acid sequence in a biological sample of a subject, the biological sample comprising nucleic acid molecules, the method comprising: (a) bringing a solution comprising the biological sample in contact with an array of probes on a solid support, wherein the array of probes has sequence complementarity to the nucleic acid sequence, wherein the nucleic acid molecules having the nucleic acid sequence are at a concentration of less than about 10% in the solution, and wherein at most a subset of the array of probes hybridizes to the nucleic acid molecules having the nucleic acid sequence if the nucleic acid molecules are present in the biological sample; (b) subjecting the array of probes to an elongation reaction under conditions that are sufficient to elongate the subset of the array of probes hybridized to the nucleic acid molecules having the nucleic acid sequence to yield elongation product(s) coupled to the solid support; (c) detecting a signal or a signal change indicative of a presence of the elongation product(s); (d) subjecting the array of probes to denaturing conditions that are sufficient to denature the elongation product(s) to yield the nucleic acid molecules in the solution; and (e) repeating (a)-(d), thereby detecting the presence of the nucleic acid sequence.

In another aspect, a non-transitory computer-readable medium comprising machine-executable code that, upon execution by one or more computer processors, implements a method for quantifying a concentration of nucleic acid molecule(s) having a nucleic acid sequence in a biological sample of a subject, the method comprising: (a) bringing a solution comprising the biological sample in contact with an array of a set of probes on a solid support, wherein the set of probes has sequence complementarity to the nucleic acid sequence, and wherein at most a subset of the set of probes hybridizes to the nucleic acid molecule(s) having the nucleic acid sequence if the nucleic acid molecule(s) is present in the biological sample; (b) subjecting the array to an elongation reaction under conditions that are sufficient to elongate the subset of the set of probes hybridized to the nucleic acid molecule(s) having the nucleic acid sequence, to yield elongation product(s) coupled to the solid support; (c) detecting a signal or a signal change indicative of a presence of the elongation product(s); (d) subjecting the array to denaturing conditions that are sufficient to denature the elongation product(s) to yield the biological sample in the solution; and (e) repeating (a)-(d) until a net signal or a net signal change exceeds a predetermined threshold, thereby quantifying the concentration of the nucleic acid molecule(s) having the nucleic acid sequence in the biological sample of the subject.

Another aspect provides a non-transitory computer-readable medium comprising machine-executable code that, upon execution by one or more computer processors, implements any of the methods above or elsewhere herein.

Another aspect provides a computer system comprising one or more computer processors and a non-transitory computer-readable medium coupled thereto. The non-transitory computer-readable medium comprises machine-executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "FIG" and "FIGS." herein), of which:

FIG. 4 shows a table with sequences of a mutant target, a wild-type target, a mutant probe and a wild-type probe that can be used for detecting mutant targets and wild-type targets in a sample (FIG. 4 discloses SEQ ID NOS 3-6, respectively, in order of appearance);

DETAILED DESCRIPTION

Figure 1:
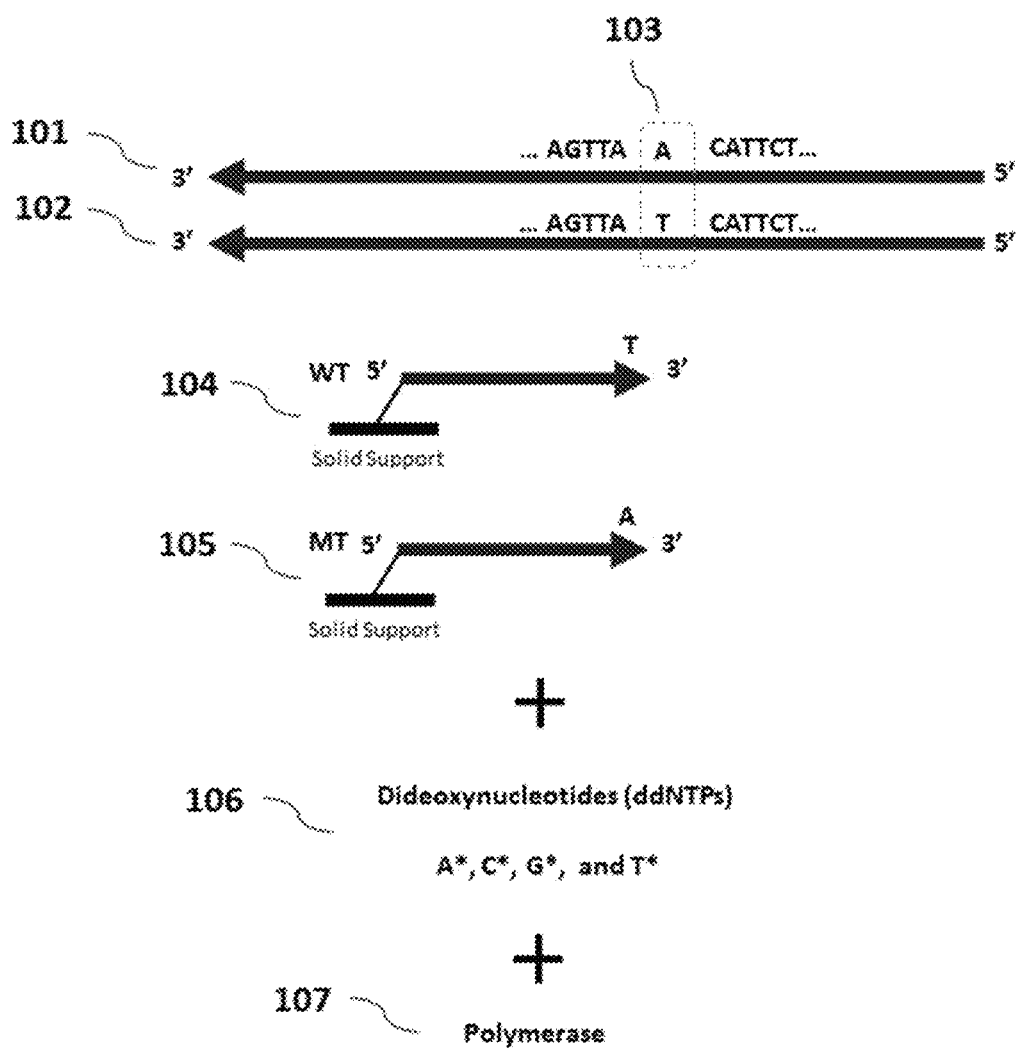
FIG. 1 schematically illustrates a wild-type sequence, a mutant sequence, a wild-type probe and a mutant probe (FIG. 1 discloses SEQ ID NOS 1-2, respectively, in order of appearance)

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "nucleotide," as used herein, generally refers to a molecule that can serve as a monomer (e.g., subunit) of a nucleic acid, such as deoxyribonucleic acid (DNA) or ribonucleic acid (RNA), or analog thereof. Non-limiting examples of nucleotides include adenosine (A), cytosine (C), guanine (G), thymine (T), uracil (U), and variants thereof. A nucleotide can include any subunit that can be incorporated into a growing nucleic acid strand. A nucleotide may be a modified nucleotide, such as a locked nucleic acid. A nucleotide may be unlabeled or labeled with one or more tags or reporters. A labeled nucleotide may yield a detectable signal, such as an optical signal, electrical signal, chemical signal, mechanical signal, or combinations thereof. The detectable signal may occur in response to a stimulus such as excitation light for fluorophore labels, or electrical potential induced by an electrode-electrolyte transducer for electrochemical reduction-oxidation (redox) labels. A nucleotide may be labeled with a molecule, such as a quencher molecule, which can reduce the detectable emission of radiation from a source that may otherwise have emitted this radiation. A nucleotide can be a deoxynucleotide (e.g., deoxynucleotide triphosphate, dNTP) or an analog thereof, e.g., a molecule having one or more phosphates in a phosphate chain, such as at least about 1, 2, 3, 4, 5, 6, 7, 8, 9, or 10 phosphates. A nucleotide can be a dideoxynucleotide (ddNTP) or an analog thereof. Dideoxynucleotides (ddNTPs), unlike dNTPs, generally lack both 2' and 3' hydroxyl groups and, after being added to a growing nucleotide chain, can result in chain termination during polymerization reactions.

The terms "polynucleotide" and "oligonucleotide" are used interchangeably to generally refer to a polymeric form of nucleotides (polynucleotide) of various lengths (e.g., at least about 2, 3, 4, 5, 6, 7, 8, 9, 10, 20, 30, 40, 50, 100, 1,000, 10,000, 100,000, 1,000,000, 10,000,000, 100,000,000 nucleotides or longer), either of ribonucleotides, deoxyribonucleotides, or analogs thereof. This term may refer to the primary structure of the molecule. Thus, the term may include triple-, double- and single-stranded DNA, as well as triple-, double- and single-stranded RNA. Non-limiting examples of polynucleotides include coding and non-coding regions of a gene or gene fragment, intergenic DNA, loci (locus) defined from linkage analysis, exons, introns, messenger RNA (mRNA), transfer RNA (tRNA), ribosomal RNA (rRNA), short interfering RNA (siRNA), short-hairpin RNA (shRNA), micro-RNA (miRNA), small nucleolar RNA, ribozymes, complementary DNA (cDNA), DNA molecules produced synthetically or by amplification, genomic DNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications may be imparted before or after assembly of the polymer. Nucleic acids can comprise phosphodiester bonds (e.g., natural nucleic acids). Nucleic acids, in some cases, may comprise nucleic acid analogs that have alternate backbones, for example, phosphoramide (see, e.g., Beaucage et al., Tetrahedron (1993) 49(10):1925 and U.S. Pat. No. 5,644,048), phosphorodithioate (see, e.g., Briu et al., J. Am. Chem. Soc. (1989) 11 1:2321), O-methylphosphoroamidite linkages (see, e.g., Eckstein, Oligonucleotides and Analogues: A Practical Approach, Oxford University Press), and peptide nucleic acid (PNA) backbones and linkages (see, e.g., Carlsson et al., Nature (1996) 380:207). Nucleic acids can comprise other analog nucleic acids including those with positive backbones (see, e.g., Denpcy et al., Proc. Natl. Acad. Sci. (1995) 92:6097); non-ionic backbones (see, e.g., U.S. Pat. Nos. 5,386,023, 5,637,684, 5,602,240, 5,216,141 and 4,469,863; Kiedrowshi et al., Angew. Chem. Intl. Ed. English (1991) 30:423; Letsinger et al., J. Am. Chem. Soc. (1988) 110:4470; Letsinger et al., Nucleoside & Nucleotide (1994) 13:1597; Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. (1994) 4:395; Jeffs et al., J. Biomolecular NMR (1994) 34:17; Horn T., et al., Tetrahedron Lett. (1996) 37:743); and non-ribose backbones, (see, e.g., U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook). Nucleic acids can comprise one or more carbocyclic sugars (see, e.g., Jenkins et al., Chem. Soc. Rev. (1995) pp 169-176). These modifications of the ribose-phosphate backbone can facilitate the addition of labels or increase the stability and/or half-life of such molecules in physiological environments.

The terms "target nucleic acid molecule", "target nucleic acid," and "target polynucleotide" may be used interchangeably to refer to a nucleic acid molecule or polynucleotide in a population of nucleic acid molecules. The presence, amount and/or nucleotide sequence of a target nucleic acid or changes in one or more of these may be desired to be determined. The target nucleic acid sequence may originate from a nucleic acid sample of interest originating from, for example, a clinical sample, such as blood, urine, saliva, exudate (e.g., pus), or a biopsy sample (e.g., solid or liquid). The target nucleic acid sequence may originate from a cell-free sample. The target polynucleotide may be a portion of a larger polynucleotide or may refer to the larger polynucleotide comprising a target sequence. The term "target sequence," as used herein, generally refers to the nucleic acid sequence on a single strand of nucleic acid, e.g., a single strand of nucleic acid of a target nucleic acid.

The term "probe," as used herein, generally refers to a molecular species or other marker that can bind to a specific target nucleic acid. A probe can be any type of molecule or particle. A probe can be a nucleic acid probe, for example a polynucleotide or oligonucleotide having a sequence that can bind, for example by hybridization, to a target nucleic acid having a target sequence. A probe can be immobilized to a substrate or other solid surface (e.g., solid-phase), for example via direct attachment or by a linker. Non-limiting examples of linkers include amino acids, polypeptides, nucleotides, oligonucleotides, and chemical linkers. A plurality of probes can be immobilized to a substrate or other solid surface and can be referred to as a probe array. A plurality of probes of a probe array may be arranged uniformly, for example as an arrangement of spots, or non-uniformly.

The terms "hybridize," "hybridization," "hybridizing," "anneal," and "annealing," as used herein, generally refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A first sequence that can be stabilized via hydrogen bonding with the bases of the nucleotide residues of a second sequence is said to be "hybridizable" to the second sequence. In such a case, the second sequence can also be said to be hybridizable to the first sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, and G-C and G-U base pairs are formed. In general, a first sequence that is hybridizable to a second sequence is specifically or selectively hybridizable to the second sequence, such that hybridization to the second sequence or set of second sequences is preferred (e.g., thermodynamically more stable under a given set of conditions, such as stringent conditions) to hybridization with non-target sequences during a hybridization reaction. Hybridizable sequences may share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity.

The term "allele(s)," as used herein, refers to any of one or more alternative forms of a gene at a particular locus, all of which relate to one trait or characteristic at the specific locus. In a diploid cell of an organism, alleles of a given gene can be located at a specific location, or locus (loci plural) on a chromosome. One allele can be present on each chromosome of the pair of homologous chromosomes. A diploid organism may comprise a large number of different alleles at a particular locus.

The term "wild-type" when made in reference to an allele or sequence can refer to the allele or sequence that encodes the phenotype most common in a particular natural population. In some cases, a wild-type allele can refer to an allele present at highest frequency in a population. In some cases, a wild-type allele or sequence refers to an allele or sequence associated with a normal state relative to an abnormal state, for example a disease state.

The term "mutant" when made in reference to an allele or sequence refers to an allele or sequence that does not encode the phenotype most common in a particular natural population. In some cases, a mutant allele can refer to an allele present at a lower frequency in a population relative to a wild-type allele. In some cases, a mutant allele or sequence can refer to an allele or sequence mutated from a wild-type sequence to a mutated sequence that presents a phenotype associated with a disease state. Mutant alleles and sequences may be different from wild-type alleles and sequences by only one to several bases. The term mutant when made in reference to a gene refers to one or more sequence mutations in a gene, including a point mutation, a single nucleotide polymorphism (SNP), an insertion, a deletion, a substitution, a transposition, a translocation, a copy number variation, or another genetic mutation, alteration or sequence variation. Numerous diseases and disorders result from mutations in single genes and may be referred to as monogenic diseases and disorders. Non-limiting examples of monogenic diseases include severe combined immunodeficiency, cystic fibrosis, lysosomal storage diseases (e.g., Gaucher's disease, Hurler's disease, Hunter syndrome, Fabry disease, Neimann-Pick disease, Tay-Sach's etc), sickle cell anemia, and thalassemia.

The term "detector," as used herein, generally refers to a device capable of detecting one or more signals and/or one or more types of signals, such as but not limited to optical signals, electrical signals, chemical signals, mechanical signals, and combinations thereof. In some cases, a detector includes optical and/or electronic components that can detect one or more signals, such as radiation including but not limited to electromagnetic radiation; electrons; protons; ions such as anions and cations; and force such as, but not limited to, mechanical force, electromagnetic force, and electrostatic force.

The term "about" or "approximately," as used herein, generally refers to a range of +/-15%, 10%, 9%, 8%, 7%, 6%, 5%, 4%, 3%, 2%, or 1% of a designated amount or value, including the amount or value itself.

The term "label," as used herein, generally refers to a specific molecular structure that can be attached to a target molecule, such as a nucleotide or polynucleotide. A label attached to a target molecule can enable the target molecule to be distinguished and traced, for example, by providing a unique characteristic not intrinsic to the target molecule.

The term "fluorophore," as used herein, refers to a chemical group that can be excited (e.g., by light or a chemical reaction) to emit radiation. Some fluorophores may be fluorescent, in which the emitted radiation has a longer wavelength than the absorbed radiation. Some fluorophores may be luminescent. Some fluorophores may be phosphorescent, in which absorbed radiation is not immediately emitted but emitted over a period ranging from at least several milliseconds to several minutes. As used herein, a "dye" may include a fluorophore. Non-limiting examples of fluorophores include 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-HAT (Hydroxy Tryptamine); 5-Hydroxy Tryptamine (HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC; AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromomycin A; CL-NERF (Ratio Dye, pH); CMFDA; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.18; Cy3.5™; Cy3™; Cy5.18; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrotluorescein Diacetate (DCFH); DID-Lipophilic Tracer; DiD (DiIC18(5)); DIDS; Dihydrorhodamine 123 (DHR); DU (DiIC18(3)); Dinitrophenol; DiO (DiOC18

(3)); DiR; DiR (DiIC18(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; Euko-Light; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluor o-Emerald; Fluor o-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 10GF; Genacryl Pink 3G; Genacryl Yellow SGF; GeneBlazer (CCF2); GFP(S65T); GFP red shifted (rsGFP); GFP wild type, non-UV excitation (wtGFP); GFP wild type, UV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, Indodicarbocyanine (DiD); Indotricarbocyanine (DiR); Intrawhite Cf; JC-1; JO-JO-1; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin EBG; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-Texas Red [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH126 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-Texas Red]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); RsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; Spectrum Aqua; Spectrum Green; Spectrum Orange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl Rodamine Iso Thio Cyanate; True Blue; TruRed; Ultralite; Uranine B; Uvitex SFC; wt GFP; WW 781; X-Rhodamine; XRITC; Xylene Orange; Y66F; Y66H; Y66 W; Yellow GFP; YFP; YO-PRO-1; YO-PRO-3; YOYO-1; and YOYO-3. As used herein, a "fluorophore" may include a salt of the fluorophore.

The term "quencher," as used herein, refers generally to a moiety or molecule that reduces and/or is capable of reducing the detectable emission of radiation, for example fluorescent or luminescent radiation, from a source that may otherwise have emitted this radiation. A quencher may be capable of reducing light emission when located in proximity to the emission source, such as at a distance less than 10 nanometers (nm) (e.g., less than 9 nm, 8 nm, 7 nm, 6 nm, 5 nm, 4 nm, 3 nm, 2 nm or less) from the emission source. In some aspects, a quencher reduces the detectable radiation emitted by the source by at least 5%, 10%, 15%, 20%, 25%, 50%, 75%, or greater. Quenching can involve any type of energy transfer, including but not limited to, photoelectron transfer, proton coupled electron transfer, dimer formation between closely situated fluorophores, transient excited state interactions, collisional quenching, or formation of non-fluorescent ground state species. A fluorophore and a quencher may not exhibit spectral overlap for quenching. In some cases, a fluorophore and a quencher may exhibit spectra overlap. As used herein, "quenching" includes any type of quenching, including dynamic (Förster-Dexter energy transfer, etc.), and static (ground state complex) quenching. A quencher can dissipate the energy absorbed from a fluorescent dye in a form other than light (e.g. as heat). Example quenchers, without limitation, include Black Hole Quencher Dyes (Biosearch Technologies) such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare).

Other examples of labels include electrochemical labels. In some cases, the electrochemical labels are reduction-oxidation (redox) molecules that can participate in a redox cycling process, in which repeated oxidations and reductions can result in current flow. Redox labels may comprise organic compounds, nanoparticles, metals, or another suitable substituent. A redox label may be oxidized and reduced repeatedly without degradation. Non-limiting examples of redox labels include ferrocene and ferrocene derivatives such as alkyl ferrocene, ferrocene acetate, alkyl ferrocene dimethylcarboxamide, acetyl ferrocene, propoyl ferrocene, butyryl ferrocene, pentanoyl ferrocene, hexanoyl ferrocene, octanoyl ferrocene, benzoyl ferrocene, 1,1'-diacetyl ferrocene, 1,1'-dibutyryl ferrocene, 1,1'-dihexanoyl ferrocene, ethyl ferrocene, propyl ferrocene, n-butyl ferrocene, pentyl ferrocene, hexyl ferrocene, 1,1'-diethyl ferrocene, 1,1'-dipropyl ferrocene, 1,1'-dibutyl ferrocene, 1,1'-dihexyl ferrocene, cyclopentenyl ferrocene, cyclohexenyl ferrocene, 3-ferrocenoyl propionic acid, 4-ferrocenoyl butyric acid, 4-ferrocenylbutyric acid, 5-ferrocenylvaleric acid, 3-ferrocenoyl propionic acid esters, 4-ferrocenoyl butyric acid esters, 4-ferrocenyl butyric acid esters, 5-ferrocenylvaleric acid esters, dimethylaminomethyl ferrocene, 1,1 dicarboxyferrocene, carboxyferrocene, and vinyl-ferrocene; porphyrin derivatives such as hydroporphyrins, chlorins, bacteriochlorins, isobacteriochlorins, decahydroporphyrins, corphins, porphyrins phthalocyanine, pyrrocorphin, and metal-complexed porphyrins including Magnesium porphyrin, Zinc porphyrin, and Iron porphyrin; quinone derivatives such as 2,5-dichloro-1,4-benzoquinone, Methylene Blue, Methyl-1, 4-benzoquinone, Anthraquinone, and 1,4-dihydroquinone; 1,4-dihydroxy-2-naphthoic acid; and nanoparticles such as CdS and ZnS nanoparticles. In some cases, the electrochemical label is a catalyst which can create a highly electrochemically-reactive molecule by acting on a substrate. Examples of catalysts that can catalyze an electrochemical reaction of a detection compound include peroxidases such as horseradish peroxide (HRP) and soybean peroxidase for use with hydrogen peroxide as a substrate; glucose oxidase and glucose dehydrogenase for use with glucose as a substrate; and lactate oxidase and lactate dehydrogenase for use with lactate as a substrate. Other labels include electrostatic labels, colorimetric labels (e.g., a colored label or a chromogenic label) and mass tags (e.g., stable isotope labels). A chromogenic label generally refers to a moiety which is colored, which can become colored after undergoing a modification such as a chemical reaction, or which becomes colored after interacting with a secondary target species. The term "chromogenic label" may also refer to a group of associated atoms which can exist in at least two states of energy, a ground state of relatively low energy and an excited state to which it may be raised by the absorption of energy, such as in the form of light, from a specified region of the radiation spectrum. Chromogenic moieties include conjugated moieties containing PI systems and metal complexes. Examples include porphyrins, polyenes, polyynes and polyaryls. The term mass tag refers generally to any moiety that is capable of being uniquely detected by virtue of its mass, for example using mass spectrometry (MS) detection techniques. Examples of mass tags include a 2-nitro-α-methyl-benzyl group, a 2-nitro-α-methyl-3-fluorobenzyl group, a 2-nitro-α-methyl-3,4-difluorobenzyl group, and a 2-nitro-α-methyl-3,4-dimethoxybenzyl group. In some cases, mass tags can be detected using parallel mass spectrometry.

Overview

The present disclosure provides methods and systems that can be used to detect the presence of a nucleic acid, for example a target nucleic acid, having a nucleic acid sequence such as a target sequence. In some cases, the nucleic acid is in the presence of background genomic material. The background genomic material may comprise background nucleic acid(s) having high sequence similarity to the nucleic acid to be detected (e.g., the target nucleic acid). Background nucleic acid(s) having high sequence similarity to the target nucleic acid may differ from the target nucleic acid by at least about 1, 2, 3, 4, 5 nucleotides or more. Provided herein are methods, devices, and systems that enable the use of cyclic solid-phase single base extension for the detection of nucleic acid sequences, (e.g. target sequences). The methods, devices, and systems of the present disclosure can comprise components including, but not limited to:

1. Sample chamber, which can include an aqueous environment in which a plurality of free-moving target nucleic acids to be analyzed are present;

2. Probe array, which can comprise a plurality of nucleic acid probes at independently (or individually) addressable locations on a solid surface (or support). The probe array can be interfaced with the sample chamber. Each addressable location (herein referred to as a "spot") can comprise a plurality of identical nucleic acids (herein referred to as "probes") that can specifically hybridize to a target nucleic acid;

3. Temperature controller, which can measure and adjust the temperature of the sample chambers, reaction solution, and array to predetermined or specific values; and 4. Detector, which can measure, in parallel, the signals generated at every addressable location. Signals can be related to a molecular labels' presence, such as an optical signal including but not limited to fluorescence or luminescence signals generated by a fluorophore; a chemical signal such as the generation of by-products from a chemical reaction; an electrical signal such as current; a mechanical signal such as a force; or combinations thereof. The signals can be discrete (e.g., individually resolvable) signals.

The probe array can include independently addressable spots (or location) that each has one or a plurality of probes. Each spot in the array may comprise the same number of probes or a different number of probes. Probes at a given independently addressable spot of the array can be different (e.g., have a different nucleic acid sequence) from probes at another independently addressable spot of the array. In some cases, probes of a group of spots of the array are the same. Probes of the group of spots can be different from probes of all other spots of the array. Each spot may comprise greater than or equal to about 5, 10, 15, 20, 25, 30, 35, 40, 45, 50, 60, 70, 80, 90, 100, 200, 300, 400, 500, 600, 700, 800, 1,000, 10,000, 100,000 or more probes. In some cases, each spot comprises less than or equal to about 10,000, 8,000, 6,000, 4,000, 2,000, 1,000, 800, 600, 400, 200, 100, 80, 60, 40, 20, 10, 5 or fewer probes.

The solid support may comprise a sensor array. The sensor array may be an integrated sensor array. The integrated sensor array may include one or more integrated detectors (e.g., detectors unitary with a solid support of the integrated sensor). The sensor array may comprise a substrate and a plurality of probes (e.g., the probe array) that attached or immobilized to a surface of the substrate. The sensor array may also comprise a single or a plurality of integrated sensors that may be capable of detecting or capturing a signal or a signal change indicative of an interaction (e.g., hybridization) between the probes and one or more analytes (e.g., a nucleic acid molecule, a template nucleic acid molecule, a primer, an amplicon, a polymerase, a nucleotide) in a reaction mixture.

A sensor array may comprise a plurality of locations, e.g., at least about 1, 10, 30, 50, 60, 70, 80, 90, 100, 300, 500, 700, 900, 1,100, 1,300, 1,500, 2,000, 4,000, 6,000, 8,000, 10,000, 20,000, 30,000, 40,000, 50,000, 60,000, 70,000, 80,000, 90,000, 100,000, 250,000, or 500,000 locations. Each of the locations may be independently or individually addressable. Each of the locations may comprise one or more sensors. Each location may correspond to or be associated with at least one spot in the probe array for detecting a signal or signal change therefrom. In some cases, each location of the sensor array corresponds to greater than or equal to about 1, 2, 3, 4, 5, 6, 7, 8, 9, 10, 12, 14, 16, 18, 20 or more spots in the probe array. In some cases, each location of the sensor array corresponds to less than or equal to about 100, 80, 60, 40, 20, 10, 9, 8, 7, 6, 5, 4, 3, 2 or fewer spots in the probe array.

Any number of sensors may be used with methods and systems of the present disclosure. In some cases, the sensor array comprises less than or equal to about 1,000,000, 750,000, 500,000, 250,000, 100,000, 75,000, 50,000, 25,000, 10,000, 7,500, 5,000, 2,500, 1,000, 900, 800, 700, 600, 500, 400, 300, 200, 100, 80, 60, 40, 20, 5, or 2 sensors, or even 1 sensor. In some cases, the sensor array comprises at least about 1, 10, 30, 50, 70, 90, 100, 300, 500, 700, 900, 1,100, 1,300, 1,500, 2,000, 4,000, 6,000, 8,000, 10,000, 20,000, 30,000, 40,000, 50,000, 60,000, 70,000, 80,000, 90,000, 100,000, 250,000, or 500,000 sensors. The sensors can be individually (or independently) addressable. In some cases, the number of sensors comprised in the sensor array is between any of the two values described herein, for example, from about 10 to 1,000 sensors.

Methods, devices, and systems of the present disclosure can employ variants of the above components assembled together to create a system capable of detecting elongation product(s), such as for example an elongation product comprising an oligonucleotide probe coupled to at least one nucleotide. One or more probes may be immobilized to a solid support to form an addressable array. The nucleic acids may be in the sample chamber (or reaction chamber) where they can move through diffusion and drift processes to interact with, and, if thermodynamically favorable, hybridize to the probes at individual spots of the addressable array. The temperature controller can set the temperature of the reaction chamber to various predefined values to facilitate or prohibit events such as hybridization of a nucleic acid to a probe, nucleotide incorporation during an elongation reaction, and denaturation of a hybridized nucleic acid and probe or a hybridized nucleic acid and elongation product. Meanwhile, the detector can measure the quantity (or magnitude) of a signal, such as an optical signal, electrical signal, chemical signal, mechanical signal, or combinations thereof, that indicates occurrences of reactions, such as nucleotide incorporation of a single-base extension reaction. An optical signal may be detectable radiation such as a fluorescence signal or luminescence signal at an independently addressable spot. In some cases, the signal may be a change, for example an increase or a decrease, of the detectable radiation from a baseline and/or reference measurement. The acquired data can be used to identify a target nucleic acid and quantify the concentration of the target nucleic acid in a nucleic acid sample. The nucleic acid sample may comprise a plurality of nucleic acids, for example background nucleic acids having high sequence similarity to the target nucleic acid.

Reaction Chamber and Solution

A reaction chamber can comprise a closed reservoir. The reaction chamber can have a volume from about 10 nanoliters (nL) to 10 milliliters (mL). In some cases, the reaction chamber volume is from about 1 microliter (µL) to 100 µL. The reaction chamber volume can be at least about 10 nL, 100 nL, 1 µL, 10 µL, 100 µL, 1 mL, or 10 mL.

A reaction chamber can contain an aqueous solution, or a reaction solution. The aqueous solution within the reaction chamber can comprise a buffered saline-based solution, such as an aqueous solution comprising a mixture of a weak acid and its conjugate base, or vice versa. The solution can comprise a plurality of nucleic acids. The plurality of nucleic acids may comprise a target nucleic acid whose presence, amount and/or nucleotide sequence or changes in one or more of these, are desired to be determined. The plurality of nucleic acids may also comprise background genomic material. One or more nucleic acids of the background genomic material may have high sequence similarity with the target sequence. The target nucleic acid can comprise RNA or DNA. A target sequence may comprise RNA or DNA, or a sequence derived from RNA or DNA. Examples of nucleotide sequences which may be target sequences are sequences corresponding to natural or synthetic RNA or DNA, including but not limited to genomic DNA and messenger RNA. The length of the sequence can be any length, for example greater than or equal to about 5, 10, 20, 50, 100, 200, 300, 400, 500, 600, 700, 800, 1,000, 1,200, 1,500, 2,000, 5,000, 10,000, 100,000 or longer nucleotides in length.

A reaction solution can comprise reagents to yield elongation products comprising a probe on a solid support and at least one nucleotide coupled thereto. An elongation product may be formed when at least one nucleotide is incorporated into a probe which is hybridized to a target nucleic acid, the target nucleic acid serving as the template for nucleotide incorporation. A reaction solution can comprise nucleotides and nucleotide analogs, such as deoxynucleotides (dNTPs), dideoxynucleotides (ddNTPs), or analogs thereof. When using ddNTPs, nucleotide incorporation can result in termination of the elongation reaction as ddNTPs can act as chain-elongation inhibitors of DNA polymerase. ddNTPs, also known as 2',3' dideoxynucleotides, lack a 3'-hydroxyl group compared to dNTPs and as a result, can inhibit chain elongation by polymerases. ddNTPs can include ddGTP, ddATP, ddTTP and ddCTP. A reaction solution may also comprise one or more polymerizing enzymes capable of incorporating one or more nucleotides, such as dNTPs and ddNTPs, into a primed probe (e.g., a probe hybridized to a nucleic acid) to yield an elongation product. Suitable polymerizing enzymes include DNA polymerases, reverse transcriptases and RNA polymerases. Suitable native or engineered polymerizing enzymes include T7 polymerase, the Klenow fragment of *E. coli* polymerase which lacks 3'-5'exonuclease activity, *E. coli* polymerase III, Sequenase™, φ29 DNA polymerase, exonuclease-free Pfu, exonuclease-free Vent™ polymerase, Thermosequenase, Thermosequenase II, Tth DNA polymerase, Tts DNA polymerase, MuLv Reverse transcriptase or HIV reverse transcriptase. The selection of an appropriate polymerase depends on various factors, such as reaction conditions including the interaction between a polymerase and a specific modified nucleotide (as described by Metzker et al., Nucleic Acids Res 1994, Nol. 22, No. 20; p. 4259-4267); reaction temperatures; ion concentrations in the reaction solution; etc.

In some cases, dNTPs and ddNTPs can include "labels" which can be used, either directly or in combination with other molecules such as reporter molecules, for the detection of elongation product(s). Labels can comprise molecular structures that, once attached to a nucleic acid, provide a distinct characteristic that is not inherent to the dNTPs, ddNTPs, or nucleic acids. In some cases, nucleotide and nucleotide analogs, including ddNTPs, can comprise fluorophores or fluorescent moieties as labels. In some cases, nucleotide and nucleotide analogs, including ddNTPs, can comprise quencher molecules. A quencher is a molecular structure that may be capable of reducing the detectable emission of radiation from a source that may have otherwise emitted the radiation. Example of quenchers, without limitation, include Black Hole Quencher Dyes (Biosearch Technologies such as BHQ-0, BHQ-1, BHQ-2, BHQ-3, BHQ-10; QSY Dye fluorescent quenchers (from Molecular Probes/Invitrogen) such as QSY7, QSY9, QSY21, QSY35, and other quenchers such as Dabcyl and Dabsyl; Cy5Q and Cy7Q and Dark Cyanine dyes (GE Healthcare). Quenchers may be used with devices, methods and systems of the present disclosure. Other examples of labels include electrochemical labels, electrostatic labels, colorimetric labels and mass tags. Examples of electrochemical labels, such as redox labels, include organic compounds, nanoparticles, and metals such as ferrocene and ferrocene derivatives, poryphyrin derivatives and metal-complexed poryphyrins, quinone derivatives, and CdS and ZnS nanoparticles. In some cases, the electrochemical label may be a catalyst such as a peroxidase (e.g., HRP and soybean peroxidase), glucose oxidase, glucose dehydrogenase, lactate oxidase, and lactate dehydrogenase.

Additional reagents that may also be present in a reaction solution and useful for generating elongation products include but are not limited to additives such as detergents, salts, including magnesium salts and potassium salts.

Samples

A biological sample can comprise tissue, cells, cell fragments, cell organelles, nucleic acids, genes, gene fragments, expression products, gene expression products, gene expression product fragments or combinations thereof. The biological sample may be a cell-free sample. A sample can be heterogeneous or homogenous. A sample can comprise blood, urine, cerebrospinal fluid, seminal fluid, saliva, sputum, stool, lymph fluid, tissue, or combinations thereof. A sample can be a tissue-specific sample such as a sample obtained from skin, heart, lung, kidney, thyroid, breast, pancreas, liver, muscle, smooth muscle, bladder, gall bladder, colon, intestine, brain, esophagus, or prostate. A sample can comprise sections of tissues, such as frozen sections or formalin-fixed sections taken for histological purposes. A biological sample can comprise cell cultures. A cell culture can be supplied from a primary cell culture, a subculture, or a cell line from any organism. A sample can be derived from a single individual organism, e.g., human, animal, plant, or microbial. A sample can alternatively be derived from two or more organisms.

A nucleic acid sample may be extracted and purified from a biological sample. A variety of kits are available for extraction of polynucleotides, selection of which may depend on the type of sample, or the type of nucleic acid to be isolated. In some cases, nucleic acid can be extracted from the entire sample obtained. In some cases, nucleic acid can be extracted from a portion of the sample obtained. Methods for DNA or RNA extraction from biological samples can include for example the use of a commercial kit, such as the Qiagen DNeasy Blood and Tissue Kit, the Qiagen EZ1 RNA Universal Tissue Kit, or the Qiagene QIAmp Circulating Nucleic Acid Kit (Qiagene). Polynucleotides may be extracted from a sample, with or without extraction from cells in a sample, according to any suitable method.

Polynucleotides can also be derived from stored samples, such frozen or archived samples. One common method for storing samples can be to formalin-fix and paraffin-embed them. However, this process can also be associated with degradation of nucleic acids. Polynucleotides processed and analyzed from a formalin-fixed, paraffin embedded (FFPE) sample may include short polynucleotides, such as fragments in the range of 50-200 base pairs, or shorter. A number of techniques exist for the purification of nucleic acids from formalin-fixed, paraffin-embedded samples, such as those described in WO2007133703, and methods described by Foss, et al Diagnostic Molecular Pathology, (1994) 3:148-155 and Paska, C., et al Diagnostic Molecular Pathology, (2004) 13:234-240. Commercially available kits may be used for purifying polynucleotides from FFPE samples, such as Ambion's Recoverall Total Nucleic acid Isolation kit. In some situations, the paraffin may be removed from the tissue via extraction with Xylene or other organic solvent, followed by treatment with heat and a protease like proteinase K which cleaves the tissue and proteins and helps to release the genomic material from the tissue. The released nucleic acids can then be captured on a membrane or precipitated from solution, washed to remove impurities and for the case of mRNA isolation, a DNase treatment step can sometimes be added to degrade unwanted DNA. Other methods for extracting FFPE DNA are available and can be used.

A nucleic acid sample can comprise nucleic acids purified from a homogenate of cells, tissues, or other biological samples. A nucleic acid sample can be the total DNA preparation of a biological sample. A nucleic acid sample can be a cell-free sample, including circulating DNA in plasma or serum such as tumor DNA and fetal DNA. A nucleic acid sample can be the genomic DNA isolated from a biological sample. A nucleic acid sample can comprise genomic DNA molecules which include both intron and exon sequences (coding sequences), as well as non-coding regulatory sequences such as promoter sequences, enhancer sequences, and 5'/3' untranslated regions (UTRs). A nucleic acid sample can be total mRNA, including but not limited to mRNA, polyA RNA, polysomal RNA, tRNA, ribosomal RNA, lincRNA, miRNA, piRNA, and siRNA, isolated from a biological sample. Nucleic acid samples can include, but are not limited to, isolated genomic DNA containing the gene or genes containing a polymorphic locus, an RNA transcript derived from the isolated genomic DNA, cDNA reverse transcribed from the transcript, cRNA transcribed from the cDNA, DNA amplified from the genes, RNA transcribed from amplified DNA, etc. In some cases, a nucleic acid sample may comprise amplification product(s) from one or more amplification processes, including polymerase chain reaction (PCR), asymmetric PCR, multiplex PCR, nested PCR, hot-start PCR, touchdown PCR, RT-PCR, and methylation specific PCR. A nucleic acid sample may comprise amplification product(s) from isothermal amplification reactions including loop-mediated isothermal amplification (LAMP), strand displacement amplification (SDA), helicase-dependent amplification (HDA), and nicking enzyme amplification reaction (NEAR). A nucleic acid sample can contain polymorphic loci of interest or nucleic acids derived from a polymorphic locus of interest. In some cases, a subset of polynucleotide sequences or genomic DNA can also be used, such as particular chromosomes.

Amplification products may be generated by subjecting a sample to nucleic acid amplification, such as polymerase chain reaction (PCR). PCR can rely on thermal cycling, including one or more cycles of repeated heating and cooling of the reaction for polynucleotide melting and enzymatic replication of the polynucleotide. Primers (short nucleic acid fragments) containing sequences complementary to a target region of a target polynucleotide along with polymerizing enzyme (e.g., DNA or RNA polymerase), can provide for the selective and repeated amplification of the target polynucleotide. The primers can have sequences that are complementary to a sequence of interest, such as a sequence with a mutation or a sequence that has been identified to predispose a subject to a given disease (e.g., cancer). As PCR progresses, the polynucleotide generated can itself used as a template for replication, setting in motion a chain reaction in which the target polynucleotide template is exponentially amplified.

As an alternative, amplification can be asymmetric PCR, which can preferentially amplify one polynucleotide strand in a double-stranded polynucleotide template. This approach can be where amplification of only one of two complementary strands is required. In asymmetric PCR, PCR is carried out as described above, but with an excess of a primer having sequence complementarity to the strand targeted for amplification. Because of the slow (arithmetic) amplification later in the reaction after the limiting primer has been exhausted, extra cycles of PCR may be required. In some cases, asymmetric amplification may use a limiting primer with a higher melting temperature (Tm) than an excess primer to maintain reaction efficiency as the limiting primer concentration decreases mid-reaction.

Amplification can be isothermal amplification. An example of an isothermal amplification method is strand displacement amplification, also referred to as SDA, which may use cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. See, e.g., U.S. Pat. Nos. 5,270,184 and 5,455,166, each of which is entirely incorporated herein by reference. Thermophilic SDA (tSDA) may use thermophilic endonucleases and polymerases at higher temperatures in essentially the same method. See, e.g., European Pat. No. 0 684 315, which is entirely incorporated herein by reference.

Examples of other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278), each of which is entirely incorporated herein by reference. In some cases, isothermal amplification utilizes transcription by an RNA polymerase from a promoter sequence, such as may be incorporated into an oligonucleotide primer. Transcription-based amplification methods may include nucleic acid sequence based amplification, also referred to as NASBA (e.g., U.S. Pat. No. 5,130,238); methods which rely on the use of an RNA replicase to amplify the probe molecule itself, commonly referred to as Qβ replicase (e.g., Lizardi, P. et al. (1988) Bio Technol. 6, 1197-1202); self-sustained sequence replication (e.g., Guatelli, J. et al. (1990) Proc. Natl. Acad. Sci. USA 87, 1874-1878; Landgren (1993) Trends in Genetics 9, 199-202; and Lee, H. H. et al., Nucleic Acid Amplification Technologies (1997)); and methods for generating additional transcription templates (e.g., U.S. Pat. Nos. 5,480,784 and 5,399,491), each of which is entirely incorporated herein by reference. Other methods of isothermal nucleic acid amplification include the use of primers containing non-canonical nucleotides (e.g., uracil or RNA nucleotides) in combination with an enzyme that cleaves nucleic acids at the non-canonical nucleotides (e.g., DNA glycosylase or RNaseH) to expose binding sites for additional primers (e.g., U.S. Pat. Nos. 6,251,639, 6,946,251, and 7,824,890), which are hereby incorporated by reference in their entirety. Isothermal amplification processes can be linear or exponential.

A nucleic acid sample can comprise a mixture of nucleic acids corresponding to a wild-type sequence and mutant sequence. A nucleic acid sample may comprise additional nucleic acid sequences that are not wild-type or mutant sequences. In some cases, a wild-type sequence can refer to a wild-type allele and a mutant sequence can refer to a mutant allele. As used herein, wild-type sequence and mutant sequence when used in reference to a nucleic acid sample or nucleic acid can refer to nucleic acid(s) comprising the sequences of the respective wild-type sequence and mutant sequence in addition to the sequence itself. Amount can be measured in any unit using any technique suitable for a particular application. In some cases, amount can be measured in units of mass (e.g., grams, milligrams, micrograms, nanograms, etc). Amount can be measured in moles (e.g., millimoles, micromoles, nanomoles, etc). Amount can be measured in units of concentration (e.g., mass/volume, moles/volume, etc). A wild-type sequence and mutant sequence can be present in a nucleic acid sample in different relative or total amounts. In some cases, wild type sequences and mutant sequences are present in amounts (e.g., mass and/or moles and/or concentration and/or percentage of total, etc) that are about equal. In some cases, a mutant sequence can be present at a lower abundance than a wild-type sequence, for example, if a mutant sequence is derived from a cancer cell population that represents a small fraction of the total number of cells of a biopsy. In some cases, a mutant sequence in a nucleic acid sample prepared from tissue obtained from a biopsy procedure can comprise less than or equal to about 90%, 80%, 70%, 60%, 50%, 40%, 30%, 20%, 15%, 10%, 9%, 8%, 7%, 6%, 5%, 4%, 3%, 2%, 1%, 0.1% or 0.01% of the nucleic acid sample or less. The concentration of a mutant sequence can depend on the source of the nucleic acid. In some cases, a mutant sequence in any nucleic acid sample can comprises less than or equal to about 90%, 80%, 70%, 60%, 50%, 40%, 30%, 20%, 15%, 14%, 13%, 12%, 11%, 10%, 9%, 8%, 7%, 6%, 5%, 4%, 3%, 2%, 1%, 0.1% or 0.01% of the nucleic acid sample or less.

The nucleic acid sample may be fragmented. Various methods are available for fragmenting polynucleotides, including but not limited to chemical, enzymatic, and mechanical methods such as sonication, shearing, and contacting with restriction enzymes. The fragments can have an average or median length from about 10 to about 1,000 nucleotides in length, such as between about 10-800, 10-500, 50-500, 90-200, or 50-150 nucleotides. The fragments can have an average or median length that is less than or equal to about 2,000, 1,800, 1,600, 1,400, 1,200, 1,000, 900, 800, 700, 600, 500, 400, 300, 200, 100, 90, 80, 70, 60, 50, 40, 30, 20, 10, 5, or fewer nucleotides.

Samples obtained using methods disclosed herein, may comprise small amounts of deoxyribonucleic acid (DNA) or ribonucleic acid (RNA). The amount of DNA or RNA in an individual sample may be less than or equal to about 500 nanograms (ng), 400 ng, 300 ng, 200 ng, 100 ng, 75 ng, 50 ng, 45 ng, 40 ng, 35 ng, 30 ng, 25 ng, 20 ng, 15 ng, 10 ng, 5 ng, 1 ng, 0.5 ng, 0.1 ng or less. The amount of DNA or RNA may be less than about 40 ng. The amount of DNA or RNA may be less than about 25 ng. The amount of DNA or RNA may be less than about 15 ng. The amount of DNA or RNA may be between about 1 ng and about 25 ng. The amount of DNA or RNA may be between about 5 ng and about 50 ng.

Probe Arrays

A probe array can comprise biological materials deposited so as to create spotted arrays. A probe can comprise materials synthesized, deposited, or positioned to form arrays according to other technologies. Thus, microarrays formed in accordance with any of these technologies may be referred to generally and collectively hereafter for convenience as "probe arrays." Oligonucleotides can be used as probes. Probe sequences can be designed to have sequence complementarity to a target sequence to facilitate hybridization between a probe and a nucleic acid comprising the target sequence.

The solid substrate can be biological, non-biological, organic, inorganic, or a combination of any of these. The substrate can exist as one or more particles, strands, precipitates, gels, sheets, tubing, spheres, containers, capillaries, pads, slices, films, plates, slides, or semiconductor integrated chips, for example. The solid substrate can be flat or can take on alternative surface configurations. For example, the solid substrate can contain raised or depressed regions on which synthesis or deposition takes place. In some examples, the solid substrate can be chosen to provide appropriate light-absorbing characteristics. For example, the substrate can be a polymerized Langmuir Blodgett film, functionalized glass, Si, Ge, GaAs, GaP, $SiO_2$, $SiN_4$, modified silicon, the top dielectric layer of a semiconductor integrated circuit (IC) chip, or any one of a variety of gels or polymers such as (poly)tetrafluoroethylene, (poly)vinylidenedifluoride, polystyrene, polycarbonate, or combinations thereof.

The plurality of probes can be located in one or more addressable regions on a solid substrate, herein referred to as "spot(s)." In some cases, a solid substrate comprises at least about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 spots with probes. In some cases, a solid substrate comprises at most about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 spots with probes. In some cases, a solid substrate comprises about 2, 3, 4, 5, 6, or 7-10, 10-50, 50-100, 100-500, 500-1,000, 1,000-5,000, 5,000-10,000, 10,000-50,000, 50,000-100,000, 100,000-500,000, 500,000-1,000,000 or over 1,000,000 spots with probes.

In some cases it may be useful to have spots which do not contain probes. Such spots can act as control spots in order to increase the quality of the measurement, for example, by using binding to the spot to estimate and correct for non-specific binding. It may also be useful to have redundant spots which have identical probe sequences to another spot but physically may not be adjacent or in proximity to the other spot. The data acquired by such probe arrays may be less susceptible to fabrication non-idealities and measurement errors.

In some cases, probes can include reporter molecules, herein referred to as "labels." Labels can comprise molecular structures that, once attached to a nucleic acid sequence, provide a distinct characteristic that is not inherent to those nucleic acid molecules. A label may produce an optical signal, an electrical signal, a chemical signal, a mechanical signal, or combinations thereof. Examples are labels that create unique optical characteristics include fluorophores and fluorescent moieties. An optical label can be used as a single signal generating entity or as part of a dual-molecule reporter in the role of either an energy donor or energy acceptor. As previously discussed, interactions between specific labels of probes and labeled nucleotides resulting from nucleotide incorporation into a probe which is hybridized to a nucleic acid sequence, wherein the nucleic acid sequence serves as a template for nucleotide incorporation, can create unique detectable signals. For example, when the labels on the probe and nucleotide, respectively, are an energy donor, such as a fluorophore, and an energy acceptor, such as a quencher, that can participate in an energy transfer phenomena, signal quenching of the energy donor can be detected when a nucleotide comprising an energy acceptor is incorporated into the probe. In some cases, probes comprise quencher molecules and nucleotides comprise fluorophores. Other examples of labels include electrochemical labels, electrostatic labels, colorimetric labels and mass tags. Labels may be used with devices, methods and systems of the present disclosure.

Labels can be coupled to a target molecule, such as a nucleic acid or nucleotide, by direct attachment or by attachment through one or more linkers (e.g., linker molecules). In some cases, labels couple to a target molecule by an electrostatic interaction that may not involve forming a covalent bond with the target molecule.

Temperature Controllers

A temperature controller can establish a specific temperature for the solution in the reaction chamber, and/or create a temperature profile that requires heating and/or cooling. A temperature controller can include a feedback control system that measures the temperature, using temperature sensors (such as a thermistor or a thermocouple), and, based on the measured temperature, add or remove heat from the reaction chamber using thermal devices (such as Peltier devices or resistive heaters). Temperature controllers can comprise heat sinks for removing heat. Temperature controllers can be integrated into an array. The temperature of an array can be controlled by individual spot, by array regions or sub-regions, or on an array-wide scale.

Temperature controllers can change the temperature of a substrate, reaction chamber, and/or array spot. The rate of temperature change can be about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. The rate of temperature change can be at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20° C./minute. Temperature controllers can change temperature at a linear rate (e.g., 5° C./second). Alternatively, temperature controllers can change temperature at a non-linear rate. Temperature controllers can increase or decrease temperature.

Detectors

The present disclosure provides detectors that may be used to detect signals, including but not limited to fluorescence signals, and signal changes, including but not limited to increases and/or decreases in fluorescence signals. Such signals can be used for detecting the presence of extension products. Such detectors can be optical detectors for measuring optical signals, electrochemical detectors for measuring electrochemical signals, or electrostatic detectors for measuring charge.

Signals detected by a detector can include signals conveying information about the presence, absence, and/or quantity of the labels. Signals can be optical signals, such as fluorescence or chemi-luminescence. Signals can be electrical, such as electrochemical signals, electrostatic signals, resistance, capacitance, or inductance. Signals can be mechanical signals, such as force signals. Signals can be processed, including normalization to a background signal. Signals can be detected in real-time.

Examples of optical detectors include but are not limited to charge-coupled device (CCDs) arrays (including cooled CCDs), complementary metal-oxide-semiconductor (CMOS) image sensor, or photomultiplier tubes (PMTs). Detectors can also include wavelength-selective components such as optical filters to allow measurement of selective wavelengths. Examples of other detectors include electrodes coupled to voltammetry detection circuitry.

The detector can sample (e.g., acquire measurements) at a rate of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 90, 120, 150, 180, 210, 240, 270, 300, 400, 500, 1000, 10,000, or 100,000 measurements per minute.

The detector can comprise a light source. The light source can be used, for example, to excite fluorescence and/or colorimetric labels. The light source can comprise at least one lamp, such as an incandescent, halogen, fluorescent, gas-discharge, arc, or light emitting diode (LED). The light source can comprise a laser. The light source can produce a specific wavelength or range or wavelengths, such as UV. The light source can comprise filters for controlling the output spectrum, wavelength, or wavelengths. The light source can comprise multiple light sources, of the same or of different types, which can be used separately or in combination.

The detector can comprise various optical elements, including but not limited to filters, lenses, collimators, mirrors, reflectors, beam splitters, and diffusers. The detector can comprise a filter or filters, including but not limited to wavelength filters (e.g., color filters, UV filters, IR filters), dichroic filters, and polarizing filters. The filters can comprise multiple filters, of the same or of different types, which can be used separately or in combination. The detector can comprise elements (e.g., signal processing unit) for removing image distortion or aberration, such as barrel or fisheye distortion, pincushion distortion, mustache distortion, monochromatic aberrations (e.g., piston, tilt, defocus, spherical aberration, coma, astigmatism, field curvature, image distortion), or chromatic aberrations (e.g., axial, longitudinal, lateral, transverse). Such elements can comprise computer systems programmed to implement instructions for partially or fully correcting image distortion. For example, Brown's distortion model or the Brown-Conrady model can be used to correct for radial distortion and tangential distortion.

In some examples, the detector can measure emitted photons coming from individual spots. These photons can be correlated to the presence and/or activity of optical labels in that area.

In some cases, the detector comprises an integrated biosensor array, which may be built using CMOS integrated circuit (IC) fabrication processes (Plummer J. D. et al., "Silicon Technologies: Fundamentals, Practice, and Modeling," Prentice Hall Electronics and VLSI Series, 2000). In such systems, herein referred to as "CMOS biochips", the probe array can be placed on top of a CMOS biochip. Examples of such systems may be found in, for example, U.S. Patent Pub. Nos. 2010/0122904, 2013/0345065, 2014/0001341, 2014/0318958, 2014/0011710, 2012/0168306, 2013/0225441, 2012/0077692, 2007/0099198, 2008/0081769, 2008/0176757 and 2008/0039339, and U.S. Pat. Nos. 8,637,436, 8,048,626, and 8,518,329, each of which is entirely incorporated herein by reference.

Figure 12:
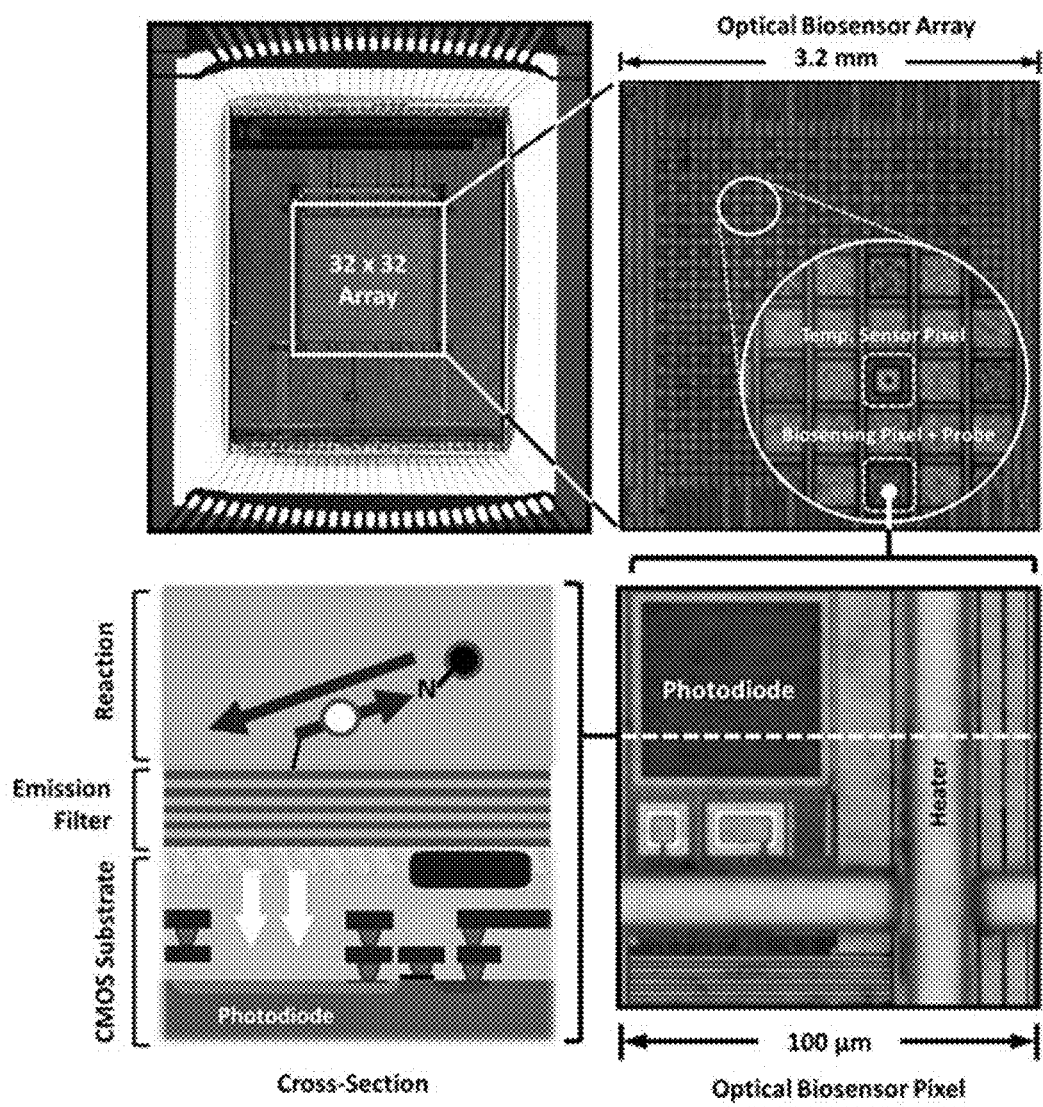
FIG. 12 shows example images and a schematic of an optical biochip detector.

FIG. 12 shows an example optical CMOS biochip detector (FIG. 12, top left) comprising a 32×32 array of optical biosensors (FIG. 12, top right) that can be used to detect optical signals, such as for example radiation including but not limited to fluorescence signals and luminescence signals. Each optical biosensor is 100 µm×100 µm square. Each side of the optical biosensor array is about 3.2 mm in length. Each biosensor comprises an embedded photodiode sensor, and an emission filter is located between the CMOS substrate of the biosensor and the reaction chamber of the associated array pixel (FIG. 12, bottom left). The heat of the array can be controlled by heaters (FIG. 12, bottom right).

Figure 13:
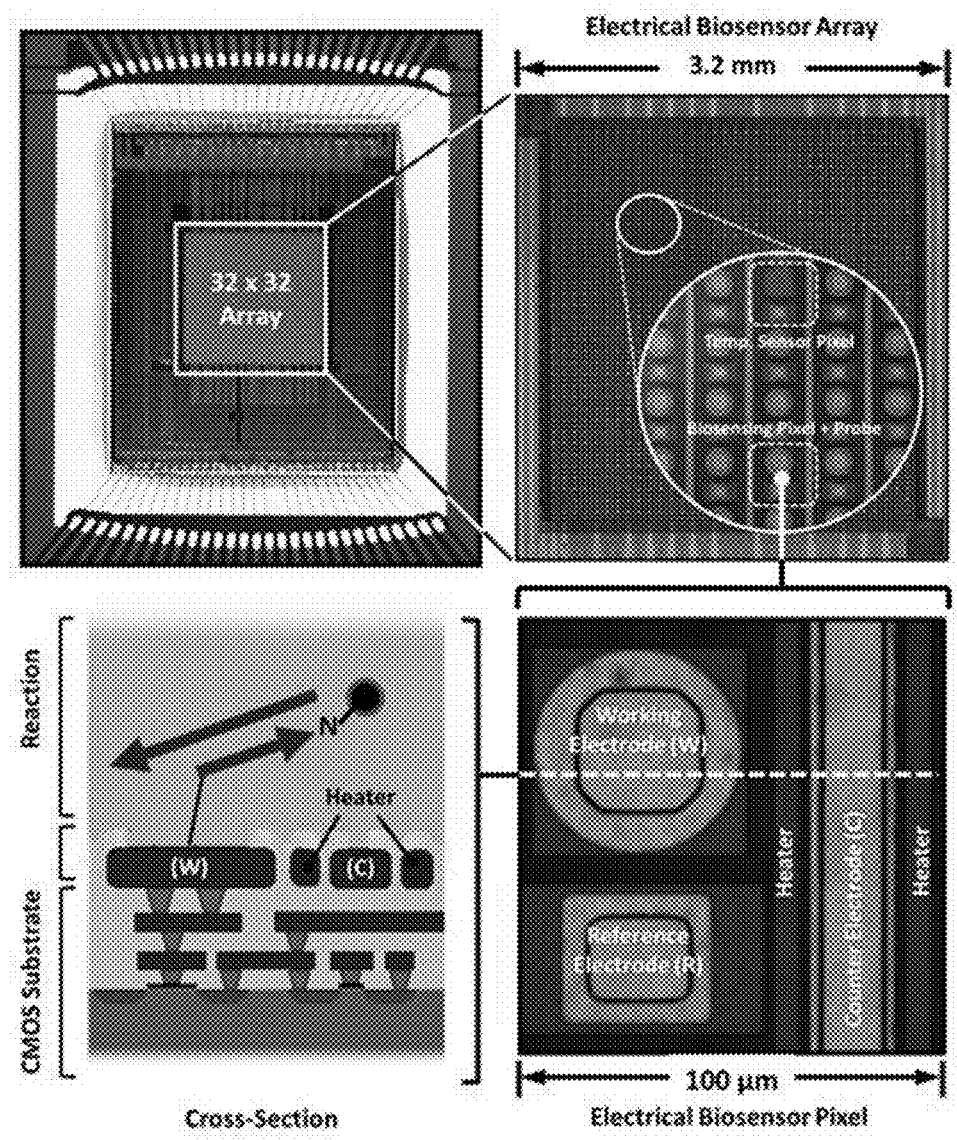
FIG. 13 shows example images and a schematic of an electrical biochip detector.

FIG. 13 shows an example electrical CMOS biochip detector (FIG. 13, top left) comprising a 32×32 array of electrical biosensors (FIG. 13, top right) that can be used to detect electrical signals in a voltammetry configuration. Each electrical biosensor is 100 µm×100 µm square. Each side of the biosensor array is about 3.2 mm in length. Each biosensor comprises a probe array located between the CMOS substrate of the biosensor and the reaction chamber of the associated array pixel (FIG. 13, bottom left). Each of the biosensors may comprise a reference electrode (R) underneath a working electrode (W), a counter electrode (C) disposed in between two heater layers. The heat of the array can be controlled by heaters (FIG. 13, bottom right).

Detection Methods

Methods, devices, and systems provided herein may be utilized to detect the presence of a target nucleic acid molecule having a target sequence by detecting the presence of elongation product(s) comprising a probe on a solid support and at least one nucleotide coupled thereto. Elongation product(s) form when at least one nucleotide can be incorporated into a probe hybridized to a target nucleic acid. A target nucleic acid hybridized to a probe can serve as a template for base or nucleotide incorporation. A probe can be a constituent of a plurality of probes located in a spot of on a probe array as described elsewhere herein.

The detection of a signal indicative of the presence of elongation product(s), such as for example an optical signal, an electrical signal, a chemical signal, a mechanical signal, or combinations thereof, can be used to detect the presence of a target nucleic acid. Where target nucleic acid molecules represent a low percentage (e.g., less than or equal to about 50%, 20%, 15%, 10%, 5%, 4%, 3%, 2%, 1%, 0.1%, 0.01% or less) of a nucleic acid sample or are present at a low concentration (e.g., a concentration less than or equal to about 50 volume %, 20 volume %, 15 volume %, 10 volume %, 5 volume %, 4 volume %, 3 volume %, 2 volume %, 1 volume %, 0.1 volume %, 0.1 volume % or less), an elongation reaction to yield elongation products can be repeated one or more times through thermally denaturing the probes and targets between each elongation steps. Using this approach, the cumulative signal or cumulative signal change over some or all elongation reactions as opposed to a single elongation process can be used to detect the presence of a target nucleic acid and quantify the amount (e.g., mass, moles, concentration, etc) of a target nucleic acid in a sample, for example a sample comprising background genomic material. This may be used with a single base extension assay. Where elongation reactions are repeated for several cycles, the number of cycles performed to reach a signal threshold or signal change threshold, either absolute or with respect to a baseline and/or reference measurement, can be used to quantify the amount (e.g., mass, moles, concentration, etc) of target nucleic acid and/or the ratio of the wild-type to the mutant in a sample.

The presence of elongation products can be determined by detecting a signal or signal change indicative of the presence of the elongation products. Signals may be optical signals, electrical signals, chemical signals, mechanical signals, or combinations thereof. The incorporation of at least one nucleotide into a probe to generate an elongation product may change a detectable property of the probe, such as but not limited to level of radiation emission, mass, volume, electric charge, conductivity and other related properties. Comparison of one or more of these signals to a baseline and/or reference values, for example prior to coupling the at least one nucleotide to the probe, and determination of a change from baseline can be used to indicate the presence of elongation product(s). In some cases, incorporation of a nucleotide into a probe may produce a by-product, such as but not limited to radiation such as electromagnetic radiation and heat; ions such as anions and cations; or other chemicals that can be detected to indicate the presence of elongation product(s).

The signal or signal change may be an optical signal or optical signal change. In some cases, a reporter molecule, such as a fluorophore, can provide the signal or the signal change indicative of the presence of elongation products. A fluorophore can emit a characteristic optical signal, for example radiation such as luminescence, phosphorescence or fluorescence, upon optical excitation or chemical reaction. A signal change indicative of the presence of elongation products may be a decrease in luminescence, phosphorescence or fluorescence signal relative to a baseline value. For example, a probe may be labeled with a fluorophore (e.g., energy donor). Upon incorporation of a quencher-labeled nucleotide into a fluorophore-labeled probe to yield an elongation product, the characteristic signal, for example the fluorescence intensity of the fluorophore, may change. The unincorporated quencher-labeled nucleotides may not create any background and/or artificial signals that interfere with the detection of elongation products, for example, if the unincorporated quencher-labeled nucleotides are located at a sufficient distance away from the probes during signal detection. In some cases, a baseline level of signal may be pre-determined and used for calibration. Fluorescence intensity can increase or decrease, in the presence of another molecule, such as an energy acceptor or quencher. The fluorescence intensity of the probe can decrease partially or completely depending on the selection of fluorophore and quencher molecule. Alternatively, a different energy donor and energy acceptor pair can be used. In cases where an elongation product is not formed and a nucleotide is not incorporated into the probe, the quencher may be absent and the fluorescence intensity of the fluorophore may not change. Generation of or changes in light or other radiation may be detected by an optical detector.

Detection and quantification of an additional target nucleic acid (e.g. a reference nucleic acid) having an additional target sequence (e.g. a reference sequence) can be performed in parallel and used as a reference. When using a reference, quantification may be provided as quantification relative to the reference (e.g. about 0.01×, 0.1×, 1×, 1.5×, 2×, 5×, 10×, 100×, etc, the abundance of the reference or some other relative measure) rather than as a numerical quantification. In some cases, the target nucleic acid molecule and the reference nucleic acid molecule are present at about the same amount, such as at about 1:1 ratio. In some cases, the reference nucleic acid molecule may be present at a higher proportion, such as at a ratio of at least about 2:1 (reference: target). In some cases, the ratio of the reference nucleic acid to the target nucleic acid can be at least about 3:1, 4:1, 5:1, 10:1, 15:1, 20:1, 50:1, or 100:1. When using numerical quantification, amounts may be measured in any suitable unit, including mass, such as grams, milligrams, micrograms, nanograms, etc; moles; and concentration such as mass per volume, moles per volume, etc. Where an amount is quantified relative to a reference sequence, the amount can be provided in various forms such as but not limited to as a percentage (%) of the reference and as positive/negative differences compared to the reference, for example as fold differences and order(s) of magnitude differences. In some cases, at least about 1, 2, 3, 4, 5, 6, 7, 8, 9, 10, 20, 30, 40, 50 or more reference sequences are used.

The nucleotide sequence of probes can be complementary to a target sequence, and probes may hybridize to a target nucleic acid. A probe can hybridize to a nucleic acid that is completely complementary in sequence. In some cases, a probe can hybridize to a nucleic acid that is not completely complementary in sequence and base mismatches can occur, for example at the 3'-end of the probe where a polymerase enzyme can facilitate elongation. In some cases, where sequence complementarity between two sequences in a nucleic acid sample is high, for example a wild-type sequence and a mutant sequence differing by one or two bases, a probe may bind to nucleic acid molecules of both sequences efficiently, despite the inherent mismatch. When bound to probes, a nucleic acid molecule can serve as a template in an elongation reaction to yield elongation products. If a probe and hybridized nucleic acid are complementary over the length of the probe, including the 3'-end of the probe, for example a wild-type probe and wild-type nucleic acid, a nucleotide can be incorporated into the probe in an elongation reaction to yield an elongation product comprising the probe and a nucleotide incorporated at the 3'-end of the probe. If there is a base mismatch or more than one base mismatch between a probe and a hybridized nucleic acid, such as at the 3'-end of the probe, for example a wild-type probe and a mutant nucleic acid, a nucleotide may not be incorporated into the probe, for example by a polymerase enzyme, in an elongation reaction. In addition to probe sequence and degree of complementarity, reaction conditions, such as buffer type, salt concentrations, and reaction solution temperature, can influence hybridization between a probe and a target nucleic acid, as well as the specificity of the elongation process.

In an example, a wild type nucleic acid 101 (WT) and a mutant nucleic acid 102 (MT) represent a reference nucleic acid having a reference sequence and a target nucleic acid having a target sequence, respectively. In this example, the WT sequence 101 and the MT sequence 102 differ at a mutation location 103, as shown in FIG. 1. The WT sequence 101 comprises an 'A' base at the mutation location and the MT sequence 102 comprises a 'T' base at the mutation location 103. To detect the presence of each of the WT nucleic acid and the MT nucleic acid, for example in a nucleic acid sample, WT and MT probes immobilized on a solid support can be subjected to elongation reactions, in which a polymerizing enzyme may yield elongation product(s) comprising an immobilized probe and at least one nucleotide coupled thereto. A WT probe 104 on a solid support having a 3' terminal nucleotide comprising a 'T' base complementary to the 'A' base of the WT sequence at the mutation location can hybridize to the WT nucleic acid. A MT probe 105 on a solid support having a 3' terminal nucleotide comprising an 'A' base complementary to the 'T' base of the MT sequence at the mutation location can hybridize to the MT nucleic acid. In the presence of ddNTPs 106 and a polymerizing enzyme such as polymerase 107, elongation products can be formed.

Figure 2A:
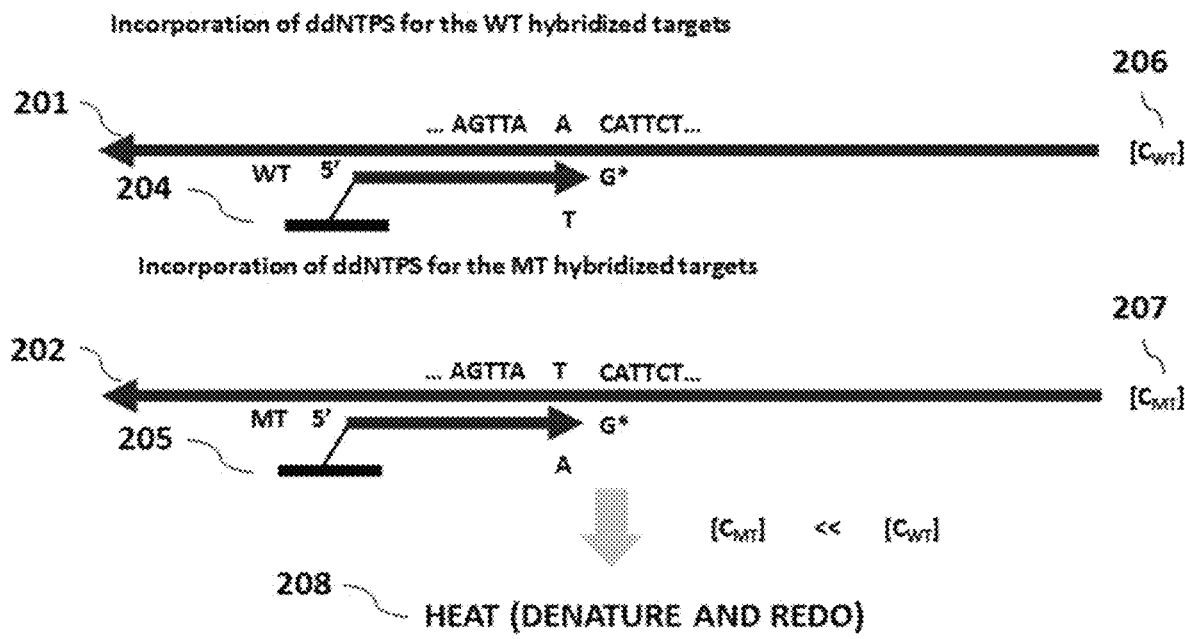
FIG. 2A schematically illustrates elongation products comprising a probe and at least one nucleotide coupled thereto (FIG. 2A discloses SEQ ID NOS 1-2, respectively, in order of appearance)

As illustrated in FIG. 2A, a WT probe 204 hybridized to a WT sequence 201 can incorporate a 'G' base into the probe in an elongation reaction using the WT sequence 201, but not the MT sequence 202, as a template and yield an elongation product comprising a probe and nucleotide coupled thereto. Similarly, a mutant probe 205 hybridized to a mutant sequence 202 can incorporate a 'G' base into the probe in an elongation reaction using the MT sequence 202, but not the WT sequence 201, as a template and yield an elongation product. If desired, such as when a target nucleic acid represents a small percentage of a nucleic acid sample or when the concentration of the MT nucleic acid 207 is less than the concentration of the WT nucleic acid 206, the array can be subjected to denaturation conditions 208, including but not limited to elevated reaction temperatures such as via heating, and hybridization and elongation can be repeated. When using dideoxynucleotides, probes with a nucleotide incorporated are subsequently unavailable for further elongation reactions.

Figure 2B:
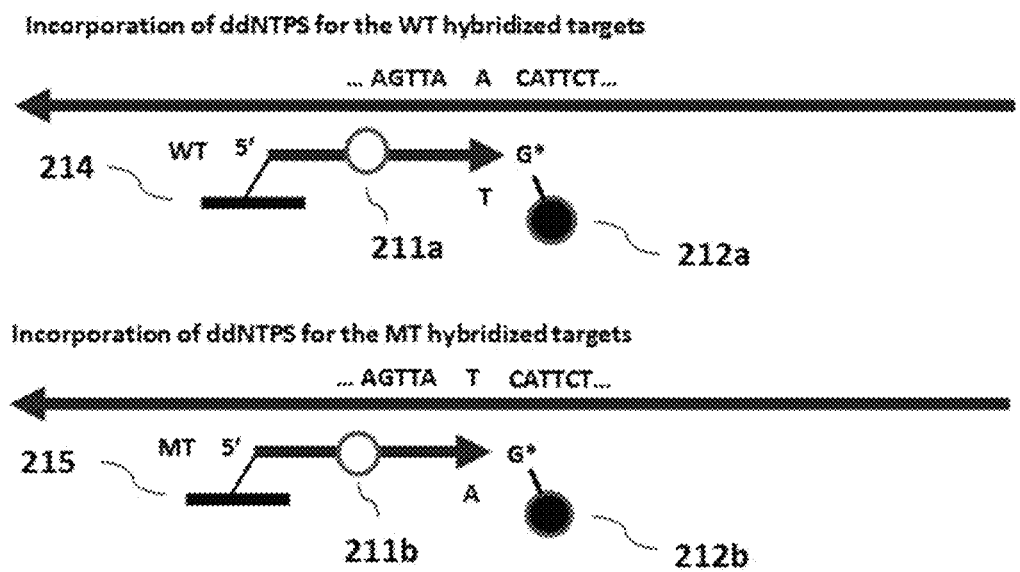
FIG. 2B schematically illustrates elongation products, wherein probes are labeled with fluorophores and nucleotides are labeled with quenchers (FIG. 2B discloses SEQ ID NOS 1-2, respectively, in order of appearance)

The incorporation of a nucleotide can generate a detectable optical signal indicative of the presence of elongation products. When a WT probe 214 and a MT probe 215 are labeled with fluorophores 211a and 211b as illustrated in FIG. 2B, the incorporation of a quencher labeled nucleotide 212a and 212b can result in decreased fluorescence from the fluorophore when the fluorophore is excited. A baseline level of fluorescence can first be determined by measuring fluorescence from fluorophores of the probes prior to any conditions sufficient to yield elongation products. Following one or more elongation reactions, fluorescence from fluorophores of the probes can be measured to determine a signal change. Decreases in fluorescence intensity can indicate the presence of one or more elongation products.

The percentage or fraction of mutant probes in a spot of a probe array bound to mutant nucleic acids may reflect the percentage or fraction of mutant nucleic acids of the total mutant and wild-type nucleic acids, assuming that both mutant and nucleic acids have about the same ability to bind to a mutant probe. For example, in a nucleic acid sample comprising wild-type and mutant nucleic acids at approximately equal proportions, a probe spot having mutant probes may have approximately 50% of its probes hybridized to mutant nucleic acids and approximately 50% of its probes hybridized to wild-type nucleic acids. Approximately 50% of the probes, for example, the approximately 50% of probes hybridized to mutant nucleic acids, may form elongation products as mutant probes hybridized to wild-type nucleic acids (e.g. approximately 50% of mutant probes in a probe spot) contain at least one mismatched base and may not form elongation products. Similarly, with a nucleic acid sample comprising wild-type and mutant nucleic acids at an approximately 3:1 ratio, a probe spot having mutant probes may have approximately 25% of its probes hybridized to mutant nucleic acids and approximately 75% of its probes hybridized to wild-type nucleic acids. Approximately 25% of the probes, for example, the approximately 25% of probes hybridized to mutant nucleic acids, may form elongation products as mutant probes hybridized to wild-type nucleic acids (e.g. approximately 75% of mutant probes in a probe spot) contain at least one mismatched base and may not form elongation products. Similarly, with a nucleic acid sample comprising wild-type and mutant nucleic acids at an approximately 9:1 ratio, a probe spot having mutant probes may have approximately 10% of its probes hybridized to mutant nucleic acids and approximately 90% of its probes hybridized to wild-type nucleic acids. Approximately 10% of the probes, for example, the approximately 10% of probes hybridized to mutant nucleic acids, may form elongation products as mutant probes hybridized to wild-type nucleic acids (e.g. approximately 90% of mutant probes in a probe spot) contain at least one mismatched base and may not form elongation products.

Figure 3A:
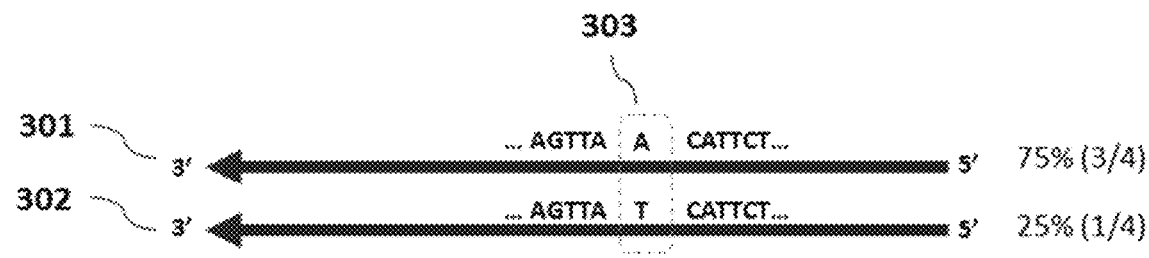
FIGS. 3A and 3B schematically illustrate the detection of mutant target sequences in a sample having both mutant sequences and wild-type sequences (FIG. 3A discloses SEQ ID NOS 1-2, respectively, in order of appearance)
Figure 3B:
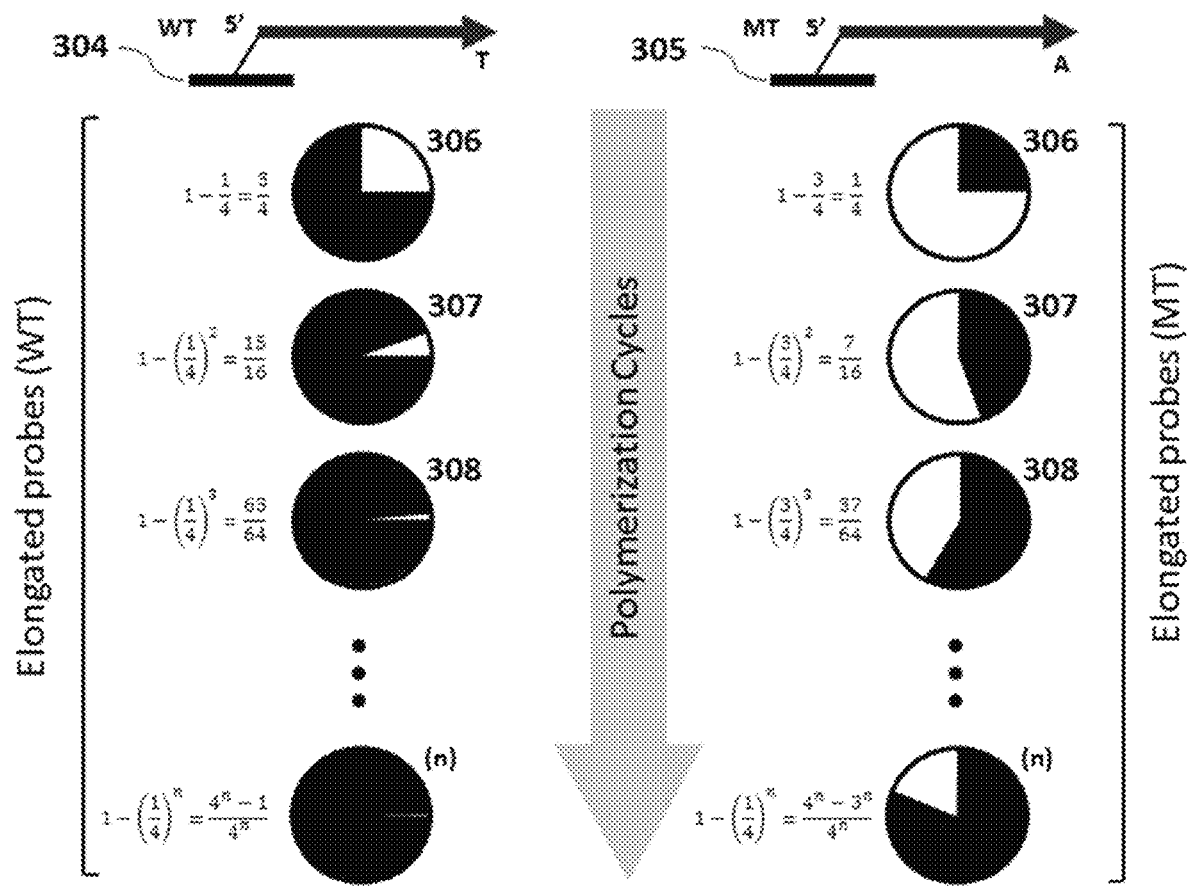

In an example as illustrated in FIGS. 3A and 3B, a nucleic acid sample of WT sequences 301 and MT sequences 302 differ at a mutation location 303. WT sequences 301 represent about 75% of the nucleic acid sample and MT sequences 302 represent about 25% of the nucleic acid sample as shown in FIG. 3A. The WT sequences 301 and MT sequences 302 can hybridize with about the same efficiency to both probes, e.g., wild WT probes 304 and MT probes 305 shown in FIG. 3B, that is, both WT and MT sequences can hybridize to both WT and MT probes at about the same rate and competition may be about equal. This may be possible, for example, if the melting temperatures ($T_m$) of both targets for both probes are well above the elongation temperature of the elongation reaction. As shown in FIG. 3B, at the onset of the first elongation reaction 306, the ratio of WT and MT targets bound to each collection of probes, e.g., WT probes and MT probes, may be similar to their concentration in solution (e.g., about 75% and about 25%). In a first elongation reaction, the probe-target complexes that have a matching 3'-end can be elongated and incorporate a ddGTP, which is complementary to the 'C' base adjacent to the mutation location 303 in both WT and MT sequences. As a result, about 75% (¾) of the WT probes in the WT spot will be elongated while about 25% (¼) of the MT probes in the MT spots will be elongated. When a quencher labeled nucleotide is incorporated into a probe to yield an elongation product, the quencher may change the detectable fluorescence emission from the fluorophore of the probe (e.g., decrease the detectable fluorescence emission) as illustrated by the shaded area of the circle. Following the first elongation reaction, an increase in temperature can denature or separate the hybridized probe-target or probe-elongation product complexes. The temperature can then be adjusted for a second elongation reaction. In the second elongation reaction 307, the ratio of WT and MT targets bound to WT and MT probes may again be similar to their concentration in solution, e.g., about 75% and about 25%. Target sequences may hybridize to both elongated and non-elongated probes. However, previously elongated probes having incorporated a chain terminating nucleotide may be unable for further elongation. In the second elongation reaction 307, about 75% (¾) of the non-elongated WT probes in the WT spot can be elongated while about 25% (¼) of the non-elongated MT probes in the MT spots can be elongated. As shown in FIG. 3B, at the end of the $2^{nd}$ elongation step, about 93% (15/16) of the WT probes are elongated and about 43% (7/16) of the MT probes are elongated. A third elongation reaction 308 may be performed, and additional elongation reactions may be performed as necessary to detect and estimate the ratio of the concentrations of WT and MT nucleic acids and/or quantify the amounts of WT and MT nucleic acids in solution. In some cases, this may be useful when a target sequence is present as a minor proportion of the nucleic acid sample. Elongation cycles can be repeated as necessary to generate sufficient signal to detect the target sequence.

In some cases, a control probe may be used. The sequence of the control probe and/or its structure may be designed such that the control probe does not hybridize to any target sequences or background molecules. During elongation, the measured signal from this probe can then be used to assess the activity of the fluorophore and also be used to calibrate fluorophore quantum yield variations as a function of pH fluctuations, temperature variations, etc. as well as any optical or chemical bleaching.

In a nucleic acid sample comprising a mixture of wild-type and mutant nucleic acids, for example a sample comprising target nucleic acid (e.g. mutant) and background genomic material (e.g. wild-type), a mutant nucleic acid may be present at a low percentage or at a low concentration, such as less than or equal to about 50%, 40%, 30%, 20%, 15%, 10%, 9%, 8%, 7%, 6%, 5%, 4%, 3%, 2%, 1%, 0.5%, 0.1%, 0.05%, 0.01%, 0.005%, 0.001% or less, or 50 volume %, 40 volume %, 30 volume %, 20 volume %, 15 volume %, 10 volume %, 9 volume %, 8 volume %, 7 volume %, 6 volume %, 5 volume %, 4 volume %, 3 volume %, 2 volume %, 1 volume %, 0.5 volume %, 0.1 volume % 0.05 volume %, 0.01 volume %, 0.005 volume %, 0.001 volume %, or less of the nucleic acid sample. A plurality of probes, for example probes in a spot of a probe array, having sequence complementarity to a mutant sequence may hybridize to both the wild-type and mutant nucleic acids in a nucleic acid sample. If a probe and hybridized nucleic acid are complementary over the length of the probe, for example a mutant probe and mutant nucleic acid, a nucleotide can be incorporated into the probe in an elongation reaction to yield an elongation product. If there is a base mismatch or more than one base mismatch between a probe and a hybridized nucleic acid, for example a mutant probe and a wild-type nucleic acid, a nucleotide may not be incorporated into the probe in an elongation reaction.

When a target nucleic acid is present in background genomic material, for example background genomic material comprising nucleic acids having high sequence similarly to the target nucleic acid, at a low percentage or a low concentration, the signal or signal change, for example detected from a probe spot, from generating elongation products may be small as a fraction of the probes in a probe spot will be bound to the target nucleic acid. The signal change may be a signal change that is less than or equal to about a 50%, 40%, 30%, 25%, 20%, 15%, 10%, 9%, 8%, 7%, 6%, 5%, 4%, 3%, 2%, 1%, 0.5%, 0.1% or smaller signal change from a baseline measurement. Elongation products can be generated by repeating hybridization and elongation reactions in cycles to generate cumulative signal. In nucleic acid samples where the concentration of a target nucleic acid, for example a mutant nucleic acid, is low, the signal change indicative of elongation products from a single elongation reaction may be low, for example a percentage signal change less than or equal 10% relative to a reference, for example a decrease of less than 10% when a fluorophore of a probe is quenched. In some cases, a percentage signal change may be less than or equal to about 50%, 40%, 30%, 20%, 10%, 9%, 8%, 7%, 6%, 5%, 4%, 3%, 2%, 1% or less relative to a reference, as a small percentage of probes may be bound to the target nucleic acid and yield an elongation product in an elongation reaction.

In some cases, dideoxynucleotides (ddNTPs), which can also be referred to as terminator dNTPs since they result in chain termination, can be used for nucleotide incorporation so that probes previously forming elongation products are unavailable to form elongation products in subsequent reactions, and signals indicative of elongation products are generated from probes with one nucleotide coupled thereto. For example, in a nucleic acid sample comprising a target nucleic acid such as a mutant nucleic acid and a reference nucleic acid such as a wild-type nucleic acid which differ by one base in sequence, the mutant nucleic acid and the wild-type nucleic acid may be present at a ratio of approximately 1:19, or approximately 5% and approximately 95% of the total. A probe spot comprising mutant probes may hybridize to both mutant and wild-type nucleic acids, for example at a ratio of approximately 1:19 wherein about 5% of the probes are hybridized to mutant nucleic acids and about 95% of the probes are hybridized to wild-type nucleic acids. About 5% of the probes, for example the probes hybridized to mutant nucleic acids, can yield elongation products. The probe spot can then be subjected to denaturing conditions sufficient to yield the nucleic acids into the reaction solution. In the presence of ddNTPs, or chain terminating nucleotides, the approximately 5% of probes of the spot that yielded elongation products may be unavailable for subsequent elongation reactions. In the next cycle of hybridization and elongation to yield elongation products using the nucleic acid sample, about 5% of the remaining approximately 95% of mutant probes of a spot may be hybridized to mutant nucleic acids and about 95% of the remaining approximately 95% of mutant probes of a spot may be hybridized to wild-type nucleic acids. Similarly, about 5% of the remaining probes available for elongation reactions (e.g. about 95% of the original probes in the probe spot), for example the probes hybridized to mutant nucleic acids and without a nucleotide, such as a ddNTP, coupled thereto, can yield elongation products. Similarly, these probes yielding elongation products may be unavailable for further elongation reactions in the presence of ddNTPs. By repeating denaturation, hybridization, and generation of elongation products, signal can accumulate over each cycle such that the cumulative signal generated or the cumulative signal change generated can be used for detecting a presence of a target nucleic acid molecule and quantifying its concentration in a nucleic acid sample, for example in samples where the target nucleic acid represents a small percentage or fraction of the nucleic acid sample.

In cases where elongation products are yielded in several cycles, the number of cycles performed to reach a signal threshold or signal change threshold, either absolute or with respect to a reference, can be used to quantify the amount (e.g., mass, moles, concentration, etc) of nucleic acid molecules having a target sequence in a sample. In some cases, the number of cycles can be compared to a reference sample of known amount in a solution (e.g., mass, moles, concentration, etc). In some cases, the amount of a nucleic acid having a target sequence in a sample is determined as a relative quantity, for example compared to a reference sequence (e.g. %, order(s) of magnitude, or fold). In some cases, at least about 5, 10, 15, 20, 25, 30, 35, 40, 45, or 50 cycles are performed. In some cases, between 5 and 100 cycles are performed. In some cases, a signal threshold is at least about a 10%, 20%, 25%, 50%, 60%, 70%, 80%, or 90% decrease in signal. In some cases, a signal threshold is at least about a 5%, 10%, 15%, 20%, 25%, 50%, 60%, 70%, 80%, or 90% increase in signal. In some cases, a signal change threshold is at least about a 5%, 10%, 15%, 20%, 25%, 50%, 60%, 70%, 80%, or 90% decrease relative to a reference. In some cases, a signal change threshold is at least about a 5%, 10%, 15%, 20%, 25%, 50%, 60%, 70%, 80%, or 90% increase relative to a reference. In some cases, at least about 2, 3, 4, 5, 6, 7, 8, 9, 10, 15, 20 reference sequences or more are used.

In alternative arrangements, nucleotide incorporation can result in increased fluorescence or altered fluorescence spectrum of an energy acceptor (FRET acceptor), for example when a FRET donor labeled nucleotide is incorporated to a FRET acceptor labeled probe. In an alternative arrangement, a FRET acceptor labeled nucleotide can be incorporated in a FRET donor labeled probe.

In alternative arrangements where nucleotides are labeled with an electrochemical label, nucleotide incorporation can result in increased electrochemical signal induced by electrochemical labels. When using electrochemical-labelled nucleotides, spots and their associated probes may include a dedicated electro-analytical system, such as an electrode connected to an electronic sensor. Once the incorporation occurs, the label is detected by the electro-analytical system. See, e.g., U.S. Pat. Nos. 8,518,329, 9,465,002, 9,223,929, and U.S. Patent Publication No. 2014-0318958, each of which is entirely incorporated herein by reference.

Methods for Detecting a Presence of a Nucleic Acid

In an aspect, a method for detecting the presence of a nucleic acid molecule having a nucleic acid sequence in a biological sample of a subject comprises bringing a solution comprising the biological sample in contact with an array of probes on a solid support. The probes may have sequence complementarity to the nucleic acid sequence. In some cases, at most a subset of the probes (e.g., less than or equal to about 90%, 80%, 70%, 60%, 50%, 45%, 40%, 35%, 30%, 25%, 20%, 15%, 10%, 5%, 1% or less of the probes) hybridizes to the nucleic acid molecule if the nucleic acid molecule is present in the biological sample. Next, the probe array may be subjected to an elongation reaction under conditions that are sufficient to elongate the subset of the probes hybridized to the nucleic acid molecule having the nucleic acid sequence, to yield elongation product(s) coupled to the solid support. In some cases, a signal or a signal change indicative of a presence of the elongation product(s) is detected during and/or after the elongation reaction. In cases where the signal or signal change is detected during the elongation reaction, the detection may occur in real-time. Subsequently, the probe array may be subjected to denaturing conditions that are sufficient to denature the elongation product(s) to release the nucleic acid molecule into the solution. In some cases, subsequent to subjecting the array to denaturing conditions, the subset of the probes that hybridized to the nucleic acid molecule and is elongated during the elongation reaction is no longer unavailable for subsequent elongation reaction(s). In some cases, one or more of the above-mentioned steps may be repeated so as to generate signals (or signal change) that are sufficient to identify or detect the presence of the nucleic acid molecule having the nucleic acid sequence in the biological sample of the subject. The one or more of the steps (e.g., contacting, hybridization, elongation, detecting and denaturation) can be repeated at least about 1, 2, 3, 4, 5, 6, 7, 8, 9, 10, 15, 20, 25, 30, 35, 40, 45, 50 or more times.

The probes may be oligonucleotide probes. An array of probes can comprise a plurality of oligonucleotides immobilized on a solid support. A probe array may comprise a plurality of probe spots. Each probe spot, as described herein, may contain a plurality of probes having the same oligonucleotide sequence. A subset of probes can hybridize to the nucleic acid molecule if the nucleic acid molecule is present in the biological the sample. Various reaction conditions and reagents can be adjusted to optimize hybridization such as but not limited to adjusting the temperature of a substrate, reaction chamber or reaction solution, or array to facilitate hybridization between the probes and nucleic acid molecules; optimizing probe length, sequence, and nucleotide composition; optimizing the preparation of nucleic acid samples including but not limited to purification techniques and nucleic acid processing; adjusting buffer components, concentrations, and additives of a solution such as a reaction solution; and combinations thereof. The temperature can be adjusted by a temperature controller. Hybridization conditions, including, but not limited to hybridization temperature(s), can depend on the melting temperature of the hybridized probe and nucleic acid molecule and reaction conditions, including buffer composition and salt concentrations. Melting temperature, also referred to as T, is a property that generally represents the temperature at which about 50% of an oligonucleotide consisting of a reference sequence (which may in fact be a sub-sequence within a larger polynucleotide) and its complementary sequence are hybridized (or separated) and can depend properties such as the length of the oligonucleotide and nucleotide composition. A melting temperature can be calculated for a polynucleotide sequence, such as for example a probe sequence.

In some cases, the nucleic acid sequence can be present in the nucleic acid molecule and when contacting the nucleic acid molecule with a probe array, a subset but not all of the probes may hybridize to the nucleic acid molecule having the nucleic acid sequence. For example, probes may hybridize to both a target nucleic acid having a target sequence and one or more additional nucleic acids having one or more additional nucleic acid sequences with high sequence similarity to the target sequence, for example the one or more additional nucleic acid sequences differing from the target sequence by at most about 100, 50, 40, 30, 20, 10, 9, 8, 7, 6, 5, 4, 3, or 2 bases, or even 1 base. The proportion of probes in the subset hybridized to target nucleic acid having the target sequence can depend on the relative proportions of the target nucleic acid and the one or more additional nucleic acids or the relative proportion of the target nucleic acid to the entire nucleic acid sample. In some cases, the target nucleic acid and the one or more additional nucleic acids are at about a 1:1 ratio, about a 1:2 ratio, about a 1:3 ratio, about a 1:4 ratio, about a 1:5 ratio, about a 1:10 ratio, about a 1:15 ratio, about a 1:20 ratio, or greater. In some cases, the target nucleic acid having the target sequence can comprise less than or equal to about 90%, 80%, 70%, 60%, 50%, 45%, 40%, 35%, 30%, 25%, 20%, 15%, 10%, 5%, 1%, 0.1% or less of the nucleic acid molecules in a biological sample. In some cases, the percentage of probes in a spot (subset of the total probes in a spot) hybridized to the nucleic acid molecule having the nucleic acid sequence is less than or equal to about 90%, 80%, 70%, 60%, 50%, 45%, 40%, 35%, 30%, 25%, 20%, 15%, 10%, 5%, 1%, 0.1% or less.

In some cases, the nucleic acid molecule is single stranded. In some cases, the nucleic acid molecule is double stranded. A double stranded nucleic acid may be treated, for example by denaturation, to yield a single stranded nucleic acid before hybridization. A nucleic acid molecule can be a deoxyribonucleic acid (DNA) or a ribonucleic acid (RNA) molecule. A nucleic acid sequence can be a deoxyribonucleic acid (DNA) sequence or a ribonucleic acid (RNA) sequence. In some cases, a nucleic acid is a cDNA that is reverse transcribed from an RNA template, for example by a reverse transcriptase. In some cases, the nucleic acid sequence comprises a sequence variant or a genomic variant. A genomic variant can be a point mutation, a single nucleotide polymorphism (SNP), an insertion, a deletion, a substitution, a transposition, a translocation, a copy number variation, or another genetic mutation, alteration or sequence variation. In some cases, the sequence variant is associated with a disease or disorder.

Oligonucleotide probes can be designed with various factors in mind. When designing probes, the probe length, nucleotide sequence, nucleotide composition, and combinations thereof may be selected for optimizing the detection of a target nucleic acid. In some cases, the probes have lengths of at least about 5, 6, 7, 8, 9, 10, 15, 20, 25, 30, 35, 40, 45, or 50 nucleotides or more. Nucleotide sequences and nucleotide composition can be selected to minimize non-specific hybridization. The probes can be deoxyribonucleic acid (DNA) oligonucleotides or ribonucleic acid (RNA)

oligonucleotides. A probe can be any probe as described elsewhere herein. In some cases, the probes comprise fluorophores. A fluorophore can be a fluorescent moiety, such as but not limited to fluorescein dyes such as 5-carboxy-2,7-dichlorofluorescein and 5-carboxyfluorescein (5-FAM) and rhodamine dyes such as carboxytetramethylrhodamine (5-TAMRA also known as TRITC).

In some cases, the probe spots of an array are individually addressable. The probe spots of an array can be simultaneously addressable. In some cases, all spots on an array may be simultaneously addressable. In some cases, the individually addressable locations can be heated independently and/or to different temperatures. The signals, for example optical signals, electrical signals, chemical signals, mechanical signals, and combinations thereof, of a spot may be detected individually and/or independently of other probe spots on the array.

In some cases, the solid support can comprise a sensor array. The sensor array can comprise one or more sensors that detect one or more signals, for example optical signals, electrical signals, chemical signals, mechanical signals and combinations thereof, or signal changes indicative of the presence of the elongation product(s). A sensor that detects a signal or signal change indicative of the presence of the elongation product(s) can be any detector as described elsewhere herein. In some cases, the signal from each individually addressable location or spot can be independently detected.

In some cases, the elongation reaction can comprise i) bringing the array of probes in contact with a polymerizing enzyme and nucleotides, and ii) using the polymerizing enzyme to incorporate at least one of the nucleotides in a given one of the probes to yield the elongation product(s).

A polymerizing enzyme can be a DNA polymerase or an RNA polymerase. A polymerizing enzyme can be thermostable. Examples of thermostable polymerizing enzymes include, but are not limited to, *Thermus thermophilus* HB8 (see, e.g., U.S. Pat. No. 5,789,224 and U.S. Patent Publication No. 20030194726); mutant *Thermus oshimai; Thermus scotoductus; Thermus thermophilus* 1B21; *Thermus thermophilus* GK24; *Thermus aquaticus* polymerase (AmpliTaq® FS or Taq (G46D; F667Y) (see e.g., U.S. Pat. No. 5,614,365), Taq (G46D; F667Y; E6811), and Taq (G46D; F667Y; T664N; R660G); *Pyrococcus furiosus* polymerase; *Thermococcus gorgonarius* polymerase; *Pyrococcus* species GB-D polymerase; *Thermococcus* sp. (strain 9° N-7) polymerase; *Bacillus stearothermophilus* polymerase; Tsp polymerase; ThermalAce™ polymerase (Invitrogen); *Thermus flavus* polymerase; *Thermus litoralis* polymerase; *Thermus* Z05 polymerase; delta Z05 polymerase (e.g. delta Z05 Gold DNA polymerase); and mutants, variants, or derivatives thereof. Additional examples of polymerizing enzymes include, but are not limited to, non-thermostable polymerases, including, but not limited to DNA polymerase I; mutant DNA polymerase I, including, but not limited to, Klenow fragment and Klenow fragment (3' to 5' exonuclease minus); T4 DNA polymerase; mutant T4 DNA polymerase; T7 DNA polymerase; mutant T7 DNA polymerase; phi29 DNA polymerase; and mutant phi29 DNA polymerase. In some cases, a hot start polymerase can be used. A hot start polymerase is a modified form of a DNA Polymerase that requires thermal activation (see for example U.S. Pat. Nos. 6,403,341 and 7,122,355, hereby incorporated by reference in their entirety). Such a polymerase can be used, for example, to further increase sensitivity, specificity, and yield; and/or to further improve low copy target amplification. Typically, the hot start enzyme can be provided in an inactive state. Upon thermal activation the modification or modifier can be released, generating active enzyme. A number of hot start polymerases are available from various commercial sources, such as Applied Biosystems; Bio-Rad; eEnzyme LLC; Eppendorf North America; Finnzymes Oy; GeneChoice, Inc.; Invitrogen; Jena Bioscience GmbH; MIDSCI; Minerva Biolabs GmbH; New England Biolabs; Novagen; Promega; QIAGEN; Roche Applied Science; Sigma-Aldrich; Stratagene; Takara Mirus Bio; USB Corp.; Yorkshire Bioscience Ltd; and the like. In some cases, the polymerizing enzyme can lack 3' to 5' exonuclease activity. In some cases, the polymerizing enzyme can lack 5' to 3' exonuclease activity.

In some cases, the nucleotides can comprise tags. A tag can be a quencher molecule or a fluorophore. In some cases, the nucleotides are inhibitors of the polymerizing enzyme. In some cases, the nucleotides are dideoxynucleotides. The nucleotides can be dideoxynucleotides labeled with quencher molecules. A quencher or quencher molecule can be any quencher as previously described herein.

The probes can comprise an energy donor molecule and the nucleotides can comprise quencher energy acceptor molecules. As an alternative, the probes can comprise an energy acceptor molecule and the nucleotides can comprise energy donor molecules.

The probes may comprise fluorophores and the nucleotides may comprise quenchers. As an alternative, the probes can comprise quenchers and the nucleotides can comprise fluorophores.

In some cases, the elongation product(s) includes the probe and at least one nucleotide coupled thereto. The at least one nucleotide may be complementary to the nucleic acid molecule. For example, the at least one nucleotide has a sequence that is at least partially or fully complementary to the nucleic acid molecule.

In some cases, the signal or the signal change indicative of a presence of the elongation products includes a decrease in fluorescence from the probes resulting from the incorporation of nucleotides comprising quenchers. The decrease may be at least about a 5%, 10%, 20%, 30%, 40%, 50%, 60%, 70%, 80%, 90%, or 95% decrease in intensity relative to a baseline and/or reference measurement. For example, the reference may be a background signal prior to any reaction under conditions sufficient to yield the elongation products.

As an alternative, the signal or the signal change indicative of a presence of the elongation products includes an increase in fluorescence. The increase may be at least about a 5%, 10%, 20%, 30%, 40%, 50%, 60%, 70%, 80%, 90%, or 95% increase in intensity relative to a baseline and/or reference measurement. For example, the reference may be a background signal prior to any reaction under conditions sufficient to yield the elongation products.

In some cases, detecting a signal or a signal change indicative of the presence of the elongation products is in the absence of Forster resonance energy transfer (FRET). In some cases, detecting the signal or the signal change comprises detecting a presence or an increase in a signal relative to a reference. In some cases, detecting the signal or the signal change comprises detecting an absence or a decrease in a signal relative to a reference. In some cases, detecting the signal or the signal change occurs in real-time.

In some cases, the denaturing conditions to yield the nucleic acid molecule in the solution include an increase in temperature. The increase in temperature can be a temperature increase of at least about 10° C., 20° C., 30° C., 40° C., 50° C., 60° C., 70° C., 75° C., 80° C., 85° C., 90° C., 95°

C., or 100° C. relative to a reference (e.g., elongation temperature, or hybridization temperature). For example, the elongation reaction can be conducted at a temperature of at least about 70° C. and the denaturing conditions include increasing the temperature to at least about 80° C.

In an aspect, a method for detecting a presence of a nucleic acid sequence in a biological sample of a subject, the biological sample comprising nucleic acid molecules having the nucleic acid sequence, comprises the step of bringing a solution comprising the biological sample in contact with an array of probes on a solid support. The probes in the array may have sequence complementarity to the nucleic acid sequence. In some cases, the nucleic acid molecules having the nucleic acid sequence are at a low concentration in the solution, e.g., less than or equal to about 90%, 80%, 70%, 60%, 50%, 45%, 40%, 35%, 30%, 25%, 20%, 15%, 10% or less in the solution. In some cases, at most a subset of the probes (e.g., less than or equal to about 90%, 80%, 70%, 60%, 50%, 45%, 40%, 35%, 30%, 25%, 20%, 15%, 10% or less of the probes) hybridizes to the nucleic acid molecules having the nucleic acid sequence if the nucleic acid molecules are present in the biological sample.

Next, the probe array can be subjected to an elongation reaction under conditions that are sufficient to elongate the subset of the probes that hybridized to the nucleic acid molecules having the nucleic acid sequence to yield elongation product(s) coupled to the solid support. During and/or after the elongation reaction, a signal or a signal change indicative of a presence of the elongation product(s) may be detected. The detection may occur at different time points during the reaction or in real-time. Subsequently, the probe array may be subjected to denaturing conditions that are sufficient to denature the elongation product(s) to yield the nucleic acid molecules in the solution. In some cases, one or more of the above-mentioned steps may be repeated so as to generate signal(s) or signal change that enables the detection of the presence of the nucleic acid sequence. In some cases, the one or more of the steps (e.g., contacting, hybridization, elongation, detecting and denaturation) are repeated at least about 1, 2, 3, 4, 5, 6, 7, 8, 9, 10, 15, 20, 25, 30, 35, 40, 45, 50 or more times.

In some cases, the concentration of the nucleic acid molecules having the nucleic acid sequence is less than or equal to about 50%, 40%, 30%, 20%, 15%, 10%, 5%, 1%, or 0.1% of the solution. In some cases, the concentration of the nucleic acid molecules having the nucleic acid sequence is between about 0% and 50% of the total nucleic acid molecules in a sample.

In some cases, the nucleic acid sequence is detected at a sensitivity (i.e., the percentage of the nucleic acid molecules that can be detected/identified by the method) of at least about 50%, 55%, 60%, 65%, 70%, 75%, 80%, 85%, 90%, 91%, 92%, 93%, 94%, 95%, 96%, 97%, 98%, 99%, 99.5% or higher. In some cases, the nucleic acid sequence can be detected at a sensitivity between about 80% and about 100%. In some cases, the nucleic acid sequence can be detected at a sensitivity of at least about 90%, 95%, 96%, 96%, 98%, 99%, or 99.5% upon repeating the one or more of the steps at least 5, 10, 20, 30, 40, 50, 60, 70, 80, 90, 100 or more times.

In some cases, the nucleic acid sequence can be detected at a sensitivity of at least about 90% upon repeating (a)-(d) at least 5 times. In some cases, the nucleic acid sequence can be detected at a sensitivity of at least about 95% upon repeating (a)-(d) at least 5 times. In some cases, the nucleic acid sequence can be detected at a sensitivity of at least about 90% upon repeating (a)-(d) at least 10 times. In some cases, the nucleic acid sequence can be detected at a sensitivity of at least about 95% upon repeating (a)-(d) at least 10 times.

In one aspect, a method for quantifying a concentration of nucleic acid molecules having a nucleic acid sequence from a biological sample of a subject comprises bringing a solution comprising the biological sample in contact with an array of a set of probes on a solid support. The set of probes may have sequence complementarity to the nucleic acid sequence. In some cases, at most a subset of the set of probes hybridizes to the nucleic acid molecules having the nucleic acid sequence if the nucleic acid molecules are present in the biological sample.

Next, the probe array may be subjected to an elongation reaction under conditions that are sufficient to elongate the subset of the set of probes hybridized to the nucleic acid molecules having the nucleic acid sequence to yield elongation product(s) coupled to the solid support. During and/or after the elongation reaction, a signal or a signal change indicative of a presence of the elongation product(s) may be detected. The detection may occur at different time points during and/or after the reaction or in real-time. Following the elongation reaction, the probe array may then be subjected to denaturing conditions that are sufficient to denature the elongation product(s) to yield the biological sample in the solution. One or more of the above-mentioned steps, including, e.g., contacting, hybridization, elongation, detecting and denaturation, may be repeated at least about 1, 2, 3, 4, 5, 6, 7, 8, 9, 10, 20, 30, 40, 50, 60, 70, 80, 90, 100 or more times until a net signal or a net signal change exceeds a predetermined threshold, thereby quantifying the concentration of nucleic acid molecules having the nucleic acid sequence from the biological sample of the subject. Such net signal or net signal change may be a quantity of signal or signal change remaining once signal artifacts (e.g., noise) have been removed. Such net signal or signal change may be relative to a baseline.

In some cases, the number of times (a)-(d) are repeated to reach the predetermined threshold can be used to quantify the concentration. In some cases, the number of times (a)-(d) are repeated to reach the predetermined threshold can be at least 5, 10, 20, 30, 40, 50, 60, 70, 80, 90, 100 times or more.

In some cases, the concentration can be quantified at an accuracy (i.e., the percentage of the nucleic acid molecule that is correctly detected or identified) of at least about 50%, 60%, 70%, 80%, 90%, 91%, 92%, 93%, 94%, 95%, 96%, 97%, 98%, 99%, or 99.5%. In some cases, the concentration can be quantified at an accuracy between 90% and 100%.

In some cases, the concentration can be quantified at a sensitivity of at least about 50%, 60%, 70%, 80%, 90%, 91%, 92%, 93%, 94%, 95%, 96%, 97%, 98%, 99%, or 99.5%. In some cases, the concentration can be quantified at a sensitivity between 90% and 100%.

In some cases, the predetermined threshold of the net signal or the net signal change can be at least about a 5%, 10%, 15%, 20%, 25%, 30%, 40%, 45%, 50%, 60%, 70%, 80%, 90%, or more decrease relative to a reference. In some cases, the predetermined threshold of the net signal or the net signal change can be at least about a 5%, 10%, 15%, 20%, 25%, 30%, 40%, 45%, 50%, 60%, 70%, 80%, 90% or more increase relative to a reference.

In some cases, the method comprises quantifying a concentration of additional nucleic acid molecules having an additional nucleic acid sequence in the biological sample. In some cases, the method comprises quantifying a concentration of additional nucleic acid molecules having at least about 1, 2, 3, 4, 5, 6, 7, 8, 9, or 10 additional nucleic acid sequences in the biological sample. In some cases, the concentration of the additional nucleic acid molecules having the additional nucleic acid sequence is quantified in parallel with quantifying the concentration of the nucleic acid molecules. In some cases, the additional nucleic acid sequence and an additional set of probes having sequence complementarity to the additional nucleic acid sequence have a hybridization thermodynamic property similar to the nucleic acid sequence and the set of probes having sequence complementarity to the nucleic acid sequence. In some cases, the hybridization thermodynamic property is melting temperature. The melting temperature of the nucleic acid sequence and the set of probes having sequence complementarity to the nucleic acid sequence can be within about ±10° C., 9° C., 8° C., 7° C., 6° C., 5° C., 4° C., 3° C., 2° C., or 1° C. of the melting temperature of the additional nucleic acid sequence and an additional set of probes having sequence complementarity to the additional nucleic acid sequence.

Computer Control Systems

Figure 11:
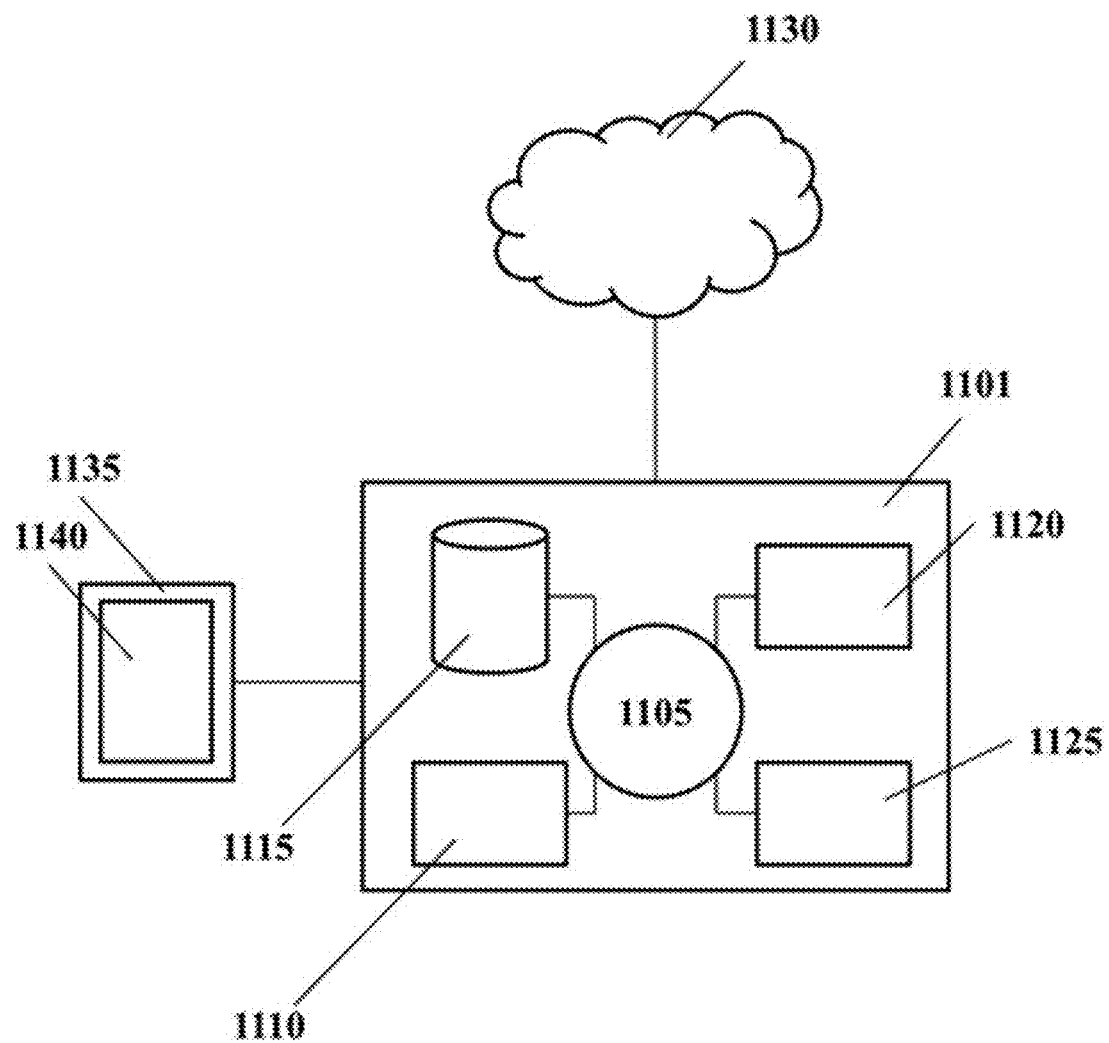
FIG. 11 shows an example schematic of a computer control system that is programmed or otherwise configured to implement methods provided herein.

The present disclosure provides computer control systems that are programmed to implement methods of the disclosure. FIG. 11 shows a computer system 1101 that is programmed or otherwise configured to detect a presence of a nucleic acid molecule having a nucleic acid sequence in a biological sample. The computer system 1101 can regulate various aspects of the present disclosure, such as, for example, temperature cycling and signal detection. The computer system 1101 can be an electronic device of a user or a computer system that is remotely located with respect to the electronic device. The electronic device can be a mobile electronic device.

The computer system 1101 includes a central processing unit (CPU, also "processor" and "computer processor" herein) 1105, which can be a single core or multi core processor, or a plurality of processors for parallel processing. The computer system 1101 also includes memory or memory location 1110 (e.g., random-access memory, read-only memory, flash memory), electronic storage unit 1115 (e.g., hard disk), communication interface 1120 (e.g., network adapter) for communicating with one or more other systems, and peripheral devices 1125, such as cache, other memory, data storage and/or electronic display adapters. The memory 1110, storage unit 1115, interface 1120 and peripheral devices 1125 are in communication with the CPU 1105 through a communication bus (solid lines), such as a motherboard. The storage unit 1115 can be a data storage unit (or data repository) for storing data. The computer system 1101 can be operatively coupled to a computer network ("network") 1130 with the aid of the communication interface 1120. The network 1130 can be the Internet, an internet and/or extranet, or an intranet and/or extranet that is in communication with the Internet. The network 1130 in some cases is a telecommunication and/or data network. The network 1130 can include one or more computer servers, which can enable distributed computing, such as cloud computing. The network 1130, in some cases with the aid of the computer system 1101, can implement a peer-to-peer network, which may enable devices coupled to the computer system 1101 to behave as a client or a server.

The CPU 1105 can execute a sequence of machine-readable instructions, which can be embodied in a program or software. The instructions may be stored in a memory location, such as the memory 1110. The instructions can be directed to the CPU 1105, which can subsequently program or otherwise configure the CPU 1105 to implement methods of the present disclosure. Examples of operations performed by the CPU 1105 can include fetch, decode, execute, and writeback.

The CPU 1105 can be part of a circuit, such as an integrated circuit. One or more other components of the system 1101 can be included in the circuit. In some cases, the circuit is an application specific integrated circuit (ASIC).

The storage unit 1115 can store files, such as drivers, libraries and saved programs. The storage unit 1115 can store user data, e.g., user preferences and user programs. The computer system 1101 in some cases can include one or more additional data storage units that are external to the computer system 1101, such as located on a remote server that is in communication with the computer system 1101 through an intranet or the Internet.

The computer system 1101 can communicate with one or more remote computer systems through the network 1130. For instance, the computer system 1101 can communicate with a remote computer system of a user (e.g., a lab technician). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1101 via the network 1130.

Methods as described herein can be implemented by way of machine (e.g., computer processor) executable code stored on an electronic storage location of the computer system 1101, such as, for example, on the memory 1110 or electronic storage unit 1115. The machine executable or machine readable code can be provided in the form of software. During use, the code can be executed by the processor 1105. In some cases, the code can be retrieved from the storage unit 1115 and stored on the memory 1110 for ready access by the processor 1105. In some situations, the electronic storage unit 1115 can be precluded, and machine-executable instructions are stored on memory 1110.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 1101, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1101 can include or be in communication with an electronic display 1135 that comprises a user interface (UI) 1140 for providing, for example, temperature values, temperature control, detector data, and fluid handling. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1105. The algorithm can, for example, control the temperature of array spots and collect and process data.

EXAMPLES

Example I: Detection of a Mutant Target by Cyclic Single Base Extension

Five mixtures comprising various concentrations of mutant (MT) and wild-type (WT) target sequences are subject to single base extension to detect the mutant and wild-type targets. The mutant sequence, target sequence, mutant probe sequence (fluorescein, FAM) and wild type probe sequence (fluorescein, FAM) are shown in the table presented in FIG. 4. The mutant probes have at the 3' end 5'-TC-3' which is complementary to the bold and underlined sequence of 5'-GA-3' in the mutant target sequence. The wild type probes have at the 3' end 5'-AA-3' which is complementary to the bold and underlined sequence of 5'-TT-3' in the wild type sequence.

Five mixtures containing different amounts of mutant and wild-type target sequences are tested—(Exp001) 0% wild type (WT) and 100% mutant (Mut); (Exp002) 50% WT and 50% Mut; (Exp003) 100% WT and 0% Mut; (Exp004) 10% WT and 90% Mut; and (Exp005) 0% WT and 100% Mut (control without enzyme). Each reaction is prepared by the addition of 10 µl of 10× ThermoPoi® Reaction Buffer (NEB), 10 µl of 1 mM BHQ10-dCTP (Biosearch), 1 µl of 2,000 U/ml Vent (exo-) DNA Polymerase (NEB), and 5 µl of a total 0.5 µM of the WT and/or Mut targets into a total volume of 100 µl reactions.

The 0.5 µM target mixtures are prepared as follows: (Exp001, Exp005) 0% WT and 100% Mut sample is prepared by adding 5 µl of 10 µM of Mut target to the reaction; (Exp002) 50% WT and 50% Mut sample is prepared by mixing 2.5 µl of 10 µM of WT target with 2.5 µl of 10 µM of Mut target; (Exp003) 100% WT and 0% Mut sample is prepared by adding 5 µl of 10 µM WT to the reaction; and (Exp004) 10% WT and 90% Mut sample is prepared by mixing 2.5 µl of 10 µM WT target with 2.5 µl of 10 µM of Mut target.

Figure 5A:
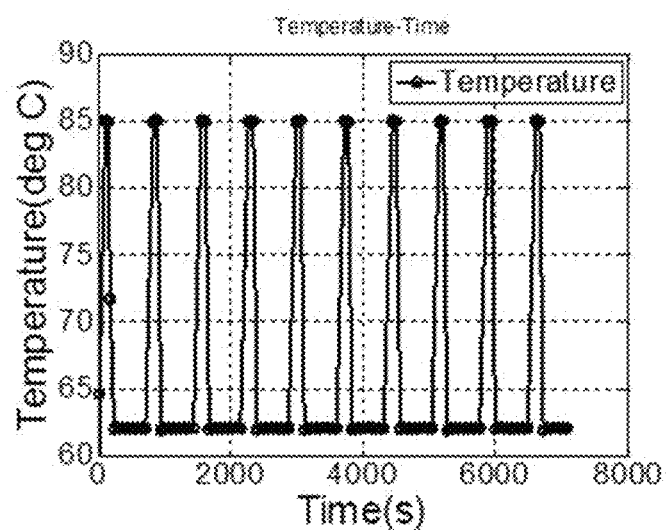
FIG. 5A shows a temperature profile of ten cycles of hybridization, probe elongation, and denaturation.
Figure 5B:
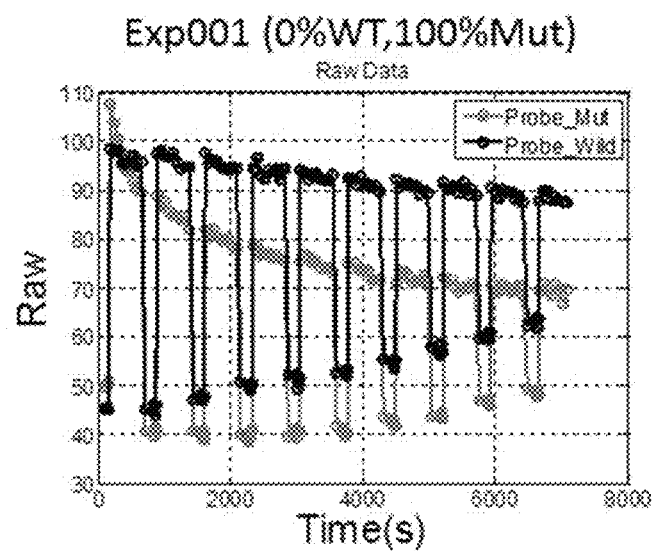
FIG. 5B shows raw fluorescence signal from wild-type and mutant probes over 10 cycles of hybridization, probe elongation, and denaturation for a sample comprising 100% mutant target and 0% wild-type target.
Figures 6A, 6B:
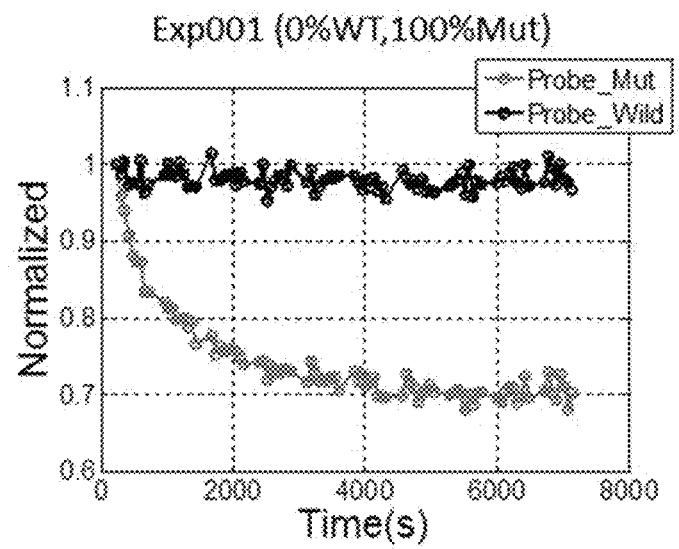
FIG. 6A shows normalized fluorescence signal from wild-type and mutant probes over 10 cycles of hybridization, probe elongation, and denaturation for a sample comprising 100% mutant target and 0% wild-type target.
FIG. 6B shows cycle by cycle ratios of normalized fluorescence signal from wild-type and mutant probes over 10 cycles of hybridization, probe elongation, and denaturation for a sample comprising 100% mutant target and 0% wild-type target.

Ten cycles of single base extension (hybridization and probe elongation following by denaturing) are performed. The temperature is cycled through 10 cycles of 62° C. and 85° C. as illustrated in FIG. 5A. As shown in FIG. 5B, raw fluorescence signal from probes decreases over time for Mut probes as quencher labeled nucleotides are incorporated into the probes for 100% Mut and 0% WT. As evident, when the temperature increases, the fluorescence signal for both probes decrease. This is due to the temperature-dependency of FAM quantum yield and can be calibrated easily by using a control probe discussed before. The raw data can be normalized as shown in FIG. 6A to show the signal decrease relative to the starting probe signal as a reference. FIG. 6B presents a table showing the cycle by cycle ratios corresponding to the normalized data.

Figures 7A, 7B:
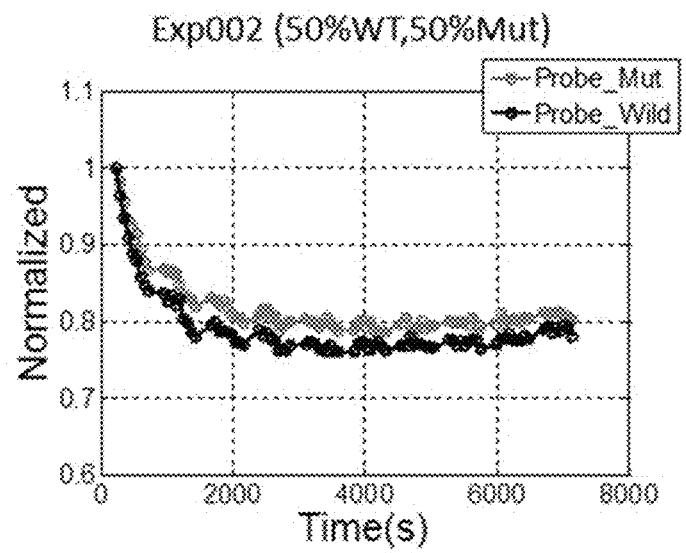
FIG. 7A shows normalized fluorescence signal from wild-type and mutant probes over 10 cycles of hybridization, probe elongation, and denaturation for a sample comprising 50% mutant target and 50% wild-type target.
FIG. 7B shows cycle by cycle ratios of normalized fluorescence signal from wild-type and mutant probes over 10 cycles of hybridization, probe elongation, and denaturation for a sample comprising 50% mutant target and 50% wild-type target.
Figures 8A, 8B:
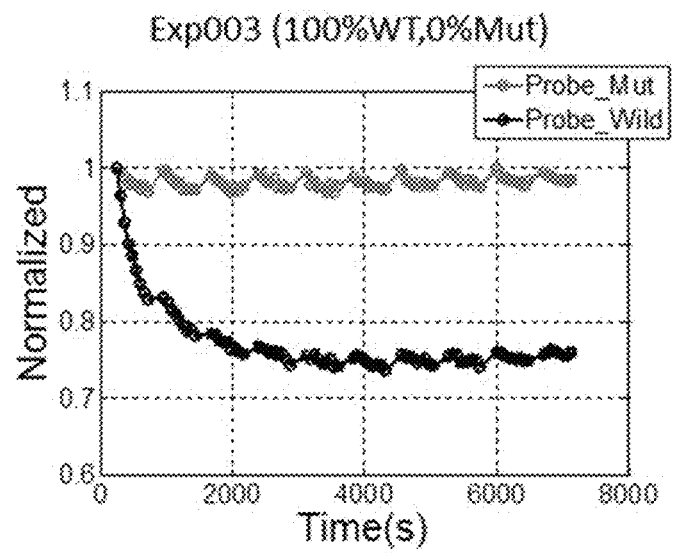
FIG. 8A shows normalized fluorescence signal from wild-type and mutant probes over 10 cycles of hybridization, probe elongation, and denaturation for a sample comprising 0% mutant target and 100% wild-type target.
FIG. 8B shows cycle by cycle ratios of normalized fluorescence signal from wild-type and mutant probes over 10 cycles of hybridization, probe elongation, and denaturation for a sample comprising 0% mutant target and 100% wild-type target.
Figures 9A, 9B:
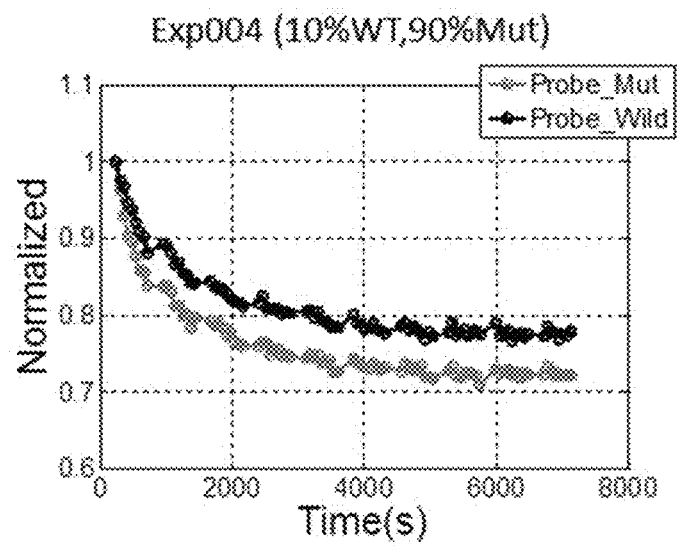
FIG. 9A shows normalized fluorescence signal from wild-type and mutant probes over 10 cycles of hybridization, probe elongation, and denaturation for a sample comprising 90% mutant target and 10% wild-type target.
FIG. 9B shows cycle by cycle ratios of normalized fluorescence signal from wild-type and mutant probes over 10 cycles of hybridization, probe elongation, and denaturation for a sample comprising 90% mutant target and 10% wild-type target.
Figure 10:
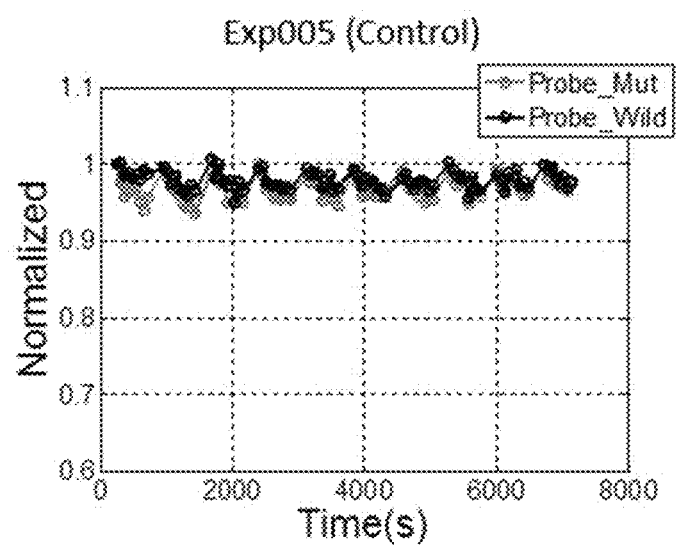
FIG. 10 shows normalized fluorescence signal from wild-type and mutant probes over 10 cycles of hybridization, probe elongation, and denaturation for a sample comprising 100% mutant target and 0% wild-type target in the absence of a polymerase.

Normalized curves of probe signal for 50% WT and 50% Mut and cycle by cycle ratios corresponding to the normalized data presented in FIG. 7A and FIG. 7B show similar decreases in signals for both wild-type and mutant probes. Normalized curves of probe signal for 100% WT and 0% Mut and cycle by cycle ratios corresponding to the normalized data presented in FIG. 8A and FIG. 8B show a decrease in signal for wild-type probes. Normalized curves of probe signal for 10% WT and 90% Mut and cycle by cycle ratios corresponding to the normalized data presented in FIG. 9A and FIG. 9B show decreases in signals for both wild-type and mutant probes, but larger decrease for Mut which represents a larger percentage of the mixture. In the control case without use of an enzyme, no signal change is observed as illustrated in FIG. 10.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for quantifying a concentration of a nucleic acid molecule having a nucleic acid sequence in a biological sample of a subject, comprising:
 (a) bringing a solution comprising said biological sample in contact with an array of probes on a solid support, wherein said array of probes has sequence complementarity to said nucleic acid sequence, and wherein at most a subset of said array of probes hybridizes to said nucleic acid molecule if said nucleic acid molecule is present in said biological sample;
 (b) subjecting said array of probes to a singe base elongation reaction in the presence of dideoxynucleotides (ddNTPs) under conditions that are sufficient to elongate said subset of said array of probes hybridized to said nucleic acid molecule having said nucleic acid sequence, to yield elongation product(s) coupled to said solid support;
 (c) detecting a signal or a signal change indicative of a presence of said elongation product(s);
 (d) subjecting said array of probes to denaturing conditions that are sufficient to denature said elongation product(s) to yield said nucleic acid molecule in said solution, wherein subsequent to subjecting said array of probes to denaturing conditions, said subset of said array of probes is unavailable for subsequent elongation; and
 (e) repeating (b)-(d), thereby quantifying said concentration of said nucleic acid molecule having said nucleic acid sequence in said biological sample of said subject.

2. The method of claim 1, wherein said nucleic acid sequence is present in said nucleic acid molecule, and wherein in (a), a subset but not all of said array of probes hybridizes to said nucleic acid molecule having said nucleic acid sequence.

3. The method of claim 1, wherein said elongation product(s) includes said subset of said array of probes and at least one nucleotide coupled thereto, wherein said at least one nucleotide is complementary to a base of said nucleic acid molecule.

4. The method of claim 1, wherein said array of probes is immobilized to said solid support at individually addressable locations.

5. The method of claim 1, wherein said nucleic acid sequence comprises a genomic variant.

6. The method of claim 1, wherein said solid support comprises a sensor array, which sensor array comprises a sensor that detects said signal or said signal change indicative of said presence of said elongation product(s).

7. The method of claim 1, wherein said single base elongation reaction comprises i) bringing said array of probes in contact with a polymerizing enzyme and nucleotides, and ii) using said polymerizing enzyme to incorporate at least one of said nucleotides in a given one of said array of probes to yield said elongation product(s).

8. The method of claim 7, wherein said nucleotides comprise tags.

9. The method of claim 8, wherein said tags are quenchers.

10. The method of claim 7, wherein said nucleotides are inhibitors of said polymerizing enzyme.

11. The method of claim 7, wherein said at least one of said nucleotides terminates said elongation reaction.

12. The method of claim 7, wherein said polymerizing enzyme lacks 3'-5' exonuclease activity.

13. The method of claim 7, wherein said array of probes comprises a fluorophore and said nucleotides comprise quenchers, and wherein said signal or said signal change includes a decrease in fluorescence from said array of probes resulting from the incorporation of said nucleotides comprising quenchers.

14. The method of claim 1, wherein said detecting is in the absence of Förster resonance energy transfer (FRET).

15. The method of claim 1, wherein said detecting said signal or said signal change comprises detecting a presence or absence of, or an increase or decrease in a signal relative to a reference.

16. The method of claim 1, wherein said detecting said signal or said signal change occurs in real-time.

17. The method of claim 1, wherein said nucleic acid sequence is detected at a sensitivity of at least 90% upon repeating (b)-(d) at least 5 times.

18. The method of claim 1, wherein said ddNTPs comprise dideoxyguanosine triphosphate (ddGTP), dideoxyadenosine triphosphate (ddATP), dideoxythymidine triphosphate (ddTTP), and dideoxycytidine triphosphate (ddCTP).

19. The method of claim 1, wherein (e) comprises repeating (b)-(d) until said signal or signal change reaches a predetermined signal threshold.

20. The method of claim 19, wherein (e) comprises repeating (b)-(d) until said signal or signal change is at or below said predetermined signal threshold.

* * * * *

```
                           SEQUENCE LISTING

<160> NUMBER OF SEQ ID NOS: 6

<210> SEQ ID NO 1
  <211> LENGTH: 12
  <212> TYPE: DNA
  <213> ORGANISM: Unknown
  <220> FEATURE:
  <223> OTHER INFORMATION: Description of Unknown:
        wild-type target sequence

<400> SEQUENCE: 1
tcttacaatt ga                                                          12

<210> SEQ ID NO 2
  <211> LENGTH: 12
  <212> TYPE: DNA
  <213> ORGANISM: Artificial Sequence
  <220> FEATURE:
  <223> OTHER INFORMATION: Description of Artificial Sequence: Synthetic
        oligonucleotide

<400> SEQUENCE: 2
tcttactatt ga                                                          12

<210> SEQ ID NO 3
  <211> LENGTH: 84
  <212> TYPE: DNA
  <213> ORGANISM: Unknown
  <220> FEATURE:
  <223> OTHER INFORMATION: Description of Unknown:
        wild-type target sequence

<400> SEQUENCE: 3
agccagccga gccaattcat gttccagaac aacccgctgt cggggttgac ctacaagcgc      60
cgactgtcgg cgctggggcc cggc                                             84

<210> SEQ ID NO 4
  <211> LENGTH: 84
  <212> TYPE: DNA
  <213> ORGANISM: Artificial Sequence
  <220> FEATURE:
  <223> OTHER INFORMATION: Description of Artificial Sequence: Synthetic
        oligonucleotide

<400> SEQUENCE: 4
agccagctga gccaattcat ggaccagaac aacccgctgt cggggttgac ccacaagcgc      60
cgactgtcgg cgctggggcc cggc                                             84

<210> SEQ ID NO 5
  <211> LENGTH: 22
  <212> TYPE: DNA
  <213> ORGANISM: Artificial Sequence
  <220> FEATURE:
  <223> OTHER INFORMATION: Description of Artificial Sequence: Synthetic
        probe

<400> SEQUENCE: 5
ccgacagcgg gttgttctgg aa                                               22

<210> SEQ ID NO 6
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
ccgacagcgg gttgttctgg tc                                              22
```